US012036023B2

(12) United States Patent
Herrera et al.

(10) Patent No.: US 12,036,023 B2
(45) Date of Patent: Jul. 16, 2024

(54) SYSTEMS AND METHODS FOR UROLOGICAL SENSING

(71) Applicant: Bright Uro, Inc., Irvine, CA (US)

(72) Inventors: Derek Herrera, San Clemente, CA (US); Bryan Nowroozi, Aliso Viejo, CA (US); Peman Montazemi, Aliso Viejo, CA (US); Hamed Shamkhalichenar, Aliso Viejo, CA (US); Kevin Arnal, Aliso Viejo, CA (US); Morgan Wendl, Aliso Viejo, CA (US); Jordan Burich, Aliso Viejo, CA (US)

(73) Assignee: Bright Uro, Inc., Irvine, CA (US)

( * ) Notice: Subject to any disclaimer, the term of this patent is extended or adjusted under 35 U.S.C. 154(b) by 0 days.

(21) Appl. No.: 18/476,963

(22) Filed: Sep. 28, 2023

(65) Prior Publication Data

US 2024/0090811 A1 Mar. 21, 2024

Related U.S. Application Data

(63) Continuation of application No. PCT/US2023/024881, filed on Jun. 8, 2023.
(Continued)

(51) Int. Cl.
*A61B 5/20* (2006.01)
*A61B 5/00* (2006.01)
(Continued)

(52) U.S. Cl.
CPC .............. *A61B 5/205* (2013.01); *A61B 5/07* (2013.01); *A61B 5/168* (2013.01); *A61B 5/6852* (2013.01);
(Continued)

(58) Field of Classification Search
CPC ........... A61B 5/205; A61B 5/07; A61B 5/168; A61B 5/6852; A61B 5/7275; A61B 5/16;
(Continued)

(56) References Cited

U.S. PATENT DOCUMENTS 10,143,391 B2 12/2018 Damaser et al.
10,478,113 B2 11/2019 Damaser et al.
(Continued)

FOREIGN PATENT DOCUMENTS

CN 110215310 B 7/2021
GB 2413769 * 11/2005 .............. A61B 5/20
(Continued)

OTHER PUBLICATIONS

Clark et al., "Effect of transducer diaphragm movement on pressure probe measurements", Chemical Engineering Science, 52, 1301-1306, 1997 (Year: 1997).*
(Continued)

*Primary Examiner* — Matthew Kremer
*Assistant Examiner* — Jonathan Drew Moroneso
(74) *Attorney, Agent, or Firm* — Knobbe, Martens, Olson & Bear, LLP

(57) ABSTRACT

A flexible sensor configured for use in a bladder is flexible and moveable from a first position in which it is configured to not be discharged from the bladder to a second position in which it is configured to be inserted into the bladder. A sensor insertion tool includes an over sheath, a push rod configured to be inserted into a first lumen of the over sheath. The flexible sensor is positioned in the first lumen of the over sheath, the push rod is then inserted partially into the over sheath behind the flexible sensor. The sensor insertion tool is then positioned at a location, such as the opening to the bladder, in which the sensor is to be deployed.

16 Claims, 85 Drawing Sheets

Related U.S. Application Data

(60) Provisional application No. 63/447,765, filed on Feb. 23, 2023, provisional application No. 63/350,305, filed on Jun. 8, 2022.

(51) Int. Cl.
  *A61B 5/07* (2006.01)
  *A61B 5/16* (2006.01)
  *A61L 29/02* (2006.01)

(52) U.S. Cl.
  CPC ............ *A61B 5/7275* (2013.01); *A61L 29/02* (2013.01); *A61B 5/16* (2013.01); *A61B 5/20* (2013.01); *A61B 5/202* (2013.01); *A61B 5/6846* (2013.01); *A61B 5/6847* (2013.01); *A61B 5/72* (2013.01); *A61B 5/7271* (2013.01); *A61B 2560/0214* (2013.01); *A61B 2562/0247* (2013.01); *A61B 2562/164* (2013.01); *A61B 2562/166* (2013.01)

(58) Field of Classification Search
  CPC ......... A61B 5/20; A61B 5/202; A61B 5/6846; A61B 5/6847; A61B 5/72; A61B 5/7271; A61B 2560/0214; A61B 2562/0247; A61B 2562/164; A61B 2562/166; A61L 29/02
  See application file for complete search history.

(56) References Cited

U.S. PATENT DOCUMENTS

| | | | |
|---|---|---|---|
| 11,207,013 | B2 | 12/2021 | Damaser et al. |
| 11,419,533 | B2 | 8/2022 | Damaser et al. |
| 2003/0100839 | A1 | 5/2003 | Cohen et al. |
| 2003/0229263 | A1 | 12/2003 | Conners et al. |
| 2005/0177067 | A1 | 8/2005 | Tracey et al. |
| 2006/0095079 | A1 | 5/2006 | Gerber |
| 2006/0247723 | A1 | 11/2006 | Gerber et al. |
| 2009/0149833 | A1 | 6/2009 | Cima et al. |
| 2010/0331770 | A1 | 12/2010 | Lee et al. |
| 2011/0152839 | A1 | 6/2011 | Cima et al. |
| 2012/0089121 | A1 | 4/2012 | Lee et al. |
| 2014/0303551 | A1* | 10/2014 | Germain .......... A61B 17/32002 606/115 |
| 2015/0164401 | A1 | 6/2015 | Toth et al. |
| 2015/0223745 | A1 | 8/2015 | Wille et al. |
| 2015/0305671 | A1 | 10/2015 | Yoon et al. |
| 2016/0374576 | A1 | 12/2016 | Ziaie et al. |
| 2018/0199816 | A1 | 7/2018 | Kalt et al. |
| 2021/0196203 | A1 | 7/2021 | Damaser et al. |
| 2023/0041528 | A1 | 2/2023 | Damaser et al. |
| 2023/0121584 | A1 | 4/2023 | Damaser et al. |

FOREIGN PATENT DOCUMENTS

| | | | |
|---|---|---|---|
| JP | 2002369810 A | 12/2002 | |
| KR | 20120016442 A | 2/2012 | |
| WO | WO-9964099 A1 * | 12/1999 | ........... A61B 5/0084 |
| WO | WO 2005115245 A1 | 12/2005 | |
| WO | WO 2016176590 A1 | 11/2016 | |
| WO | WO 2016191479 A1 | 12/2016 | |
| WO | WO 2017136212 A1 | 8/2017 | |
| WO | WO 2023014785 A1 | 2/2023 | |

OTHER PUBLICATIONS

Coleman et al., "A Gel filled intravaginal transducer for extended measurements of intra-abdominal pressure," 2010 Annual International Conference of the IEEE Engineering in Medicine and Biology, Buenos Aires, Argentina, 2010, pp. 1852-1855, doi: 10.1109/IEMBS,2010.5625987. (Year: 2010).

Kim et al., "A Generic packaging technique using fluidic isolation or low-drift implantable pressure sensors" 2015 Transducers, 2015 18th International Conference on Solid State Sensors, Actuators and Microsystems, IEEE, 21, pp. 476-479.

PCT International Search Report and Written Opinion for International Application No. PCT/US2023/024881, mailed Jan. 18, 2024, in 13 pages.

* cited by examiner

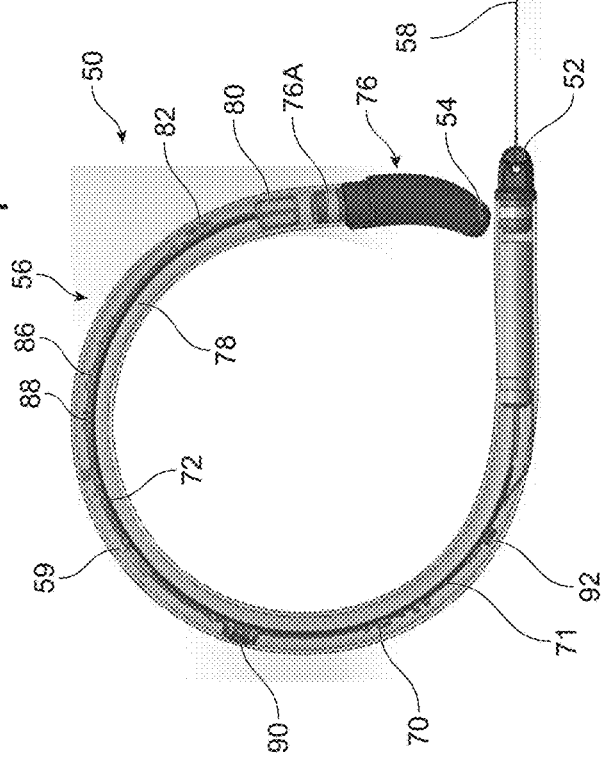
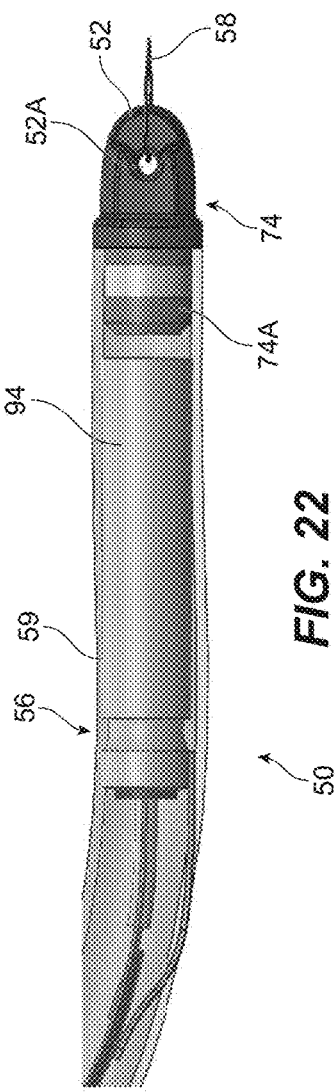
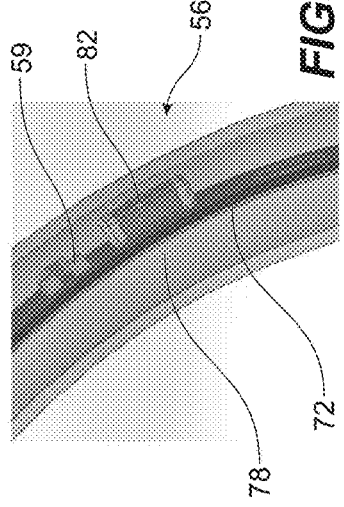
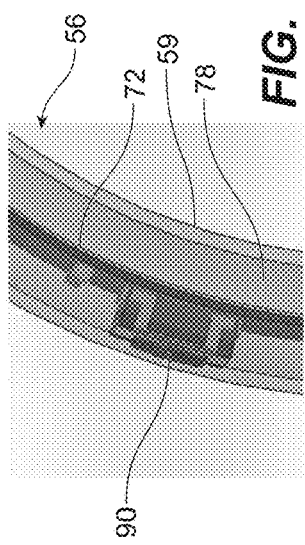
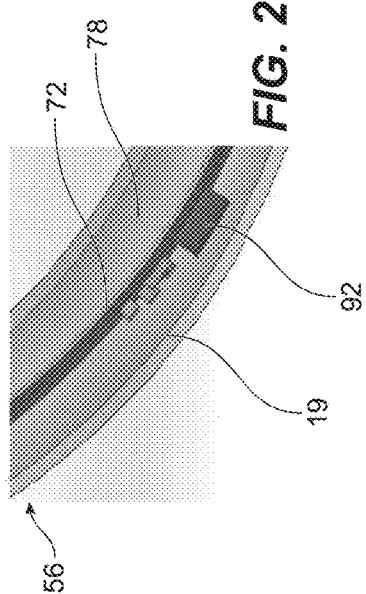

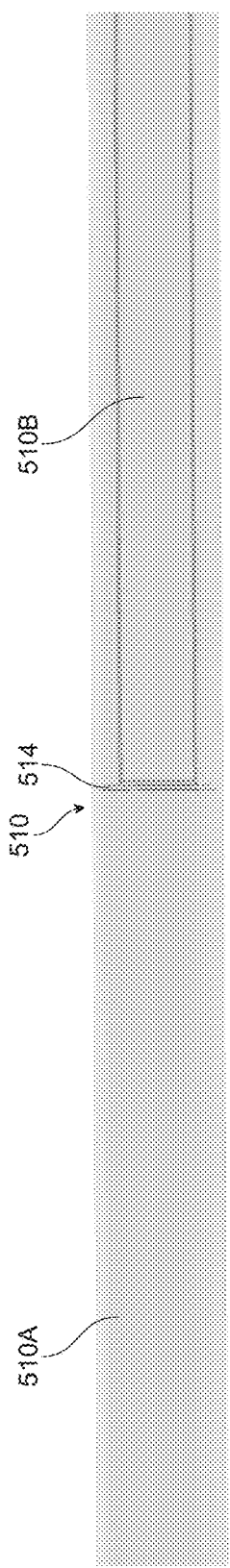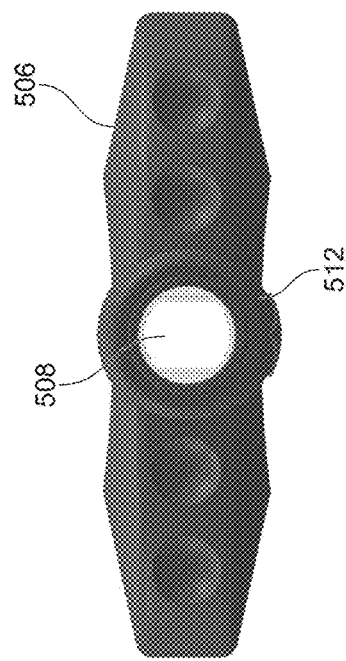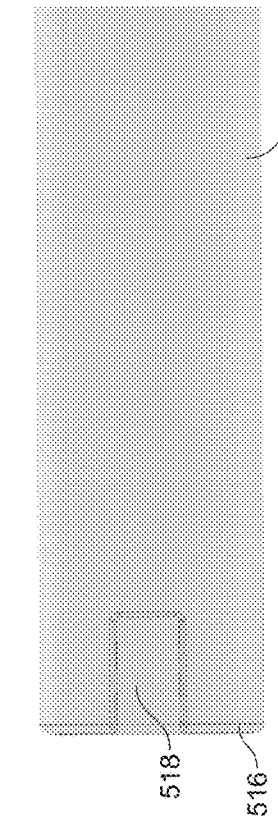
*FIG. 30*
*FIG. 29*
*FIG. 28*

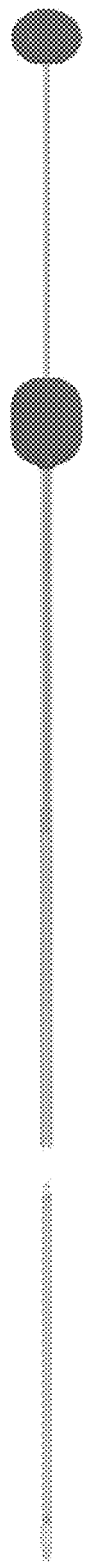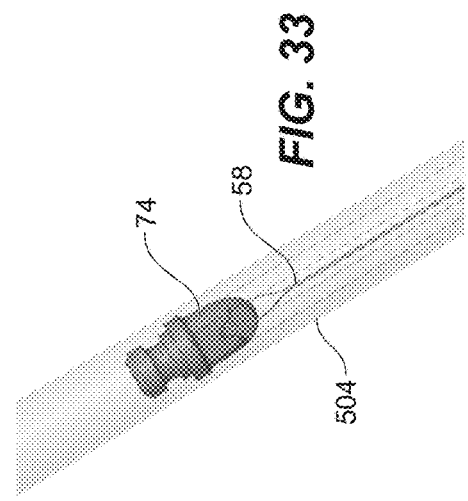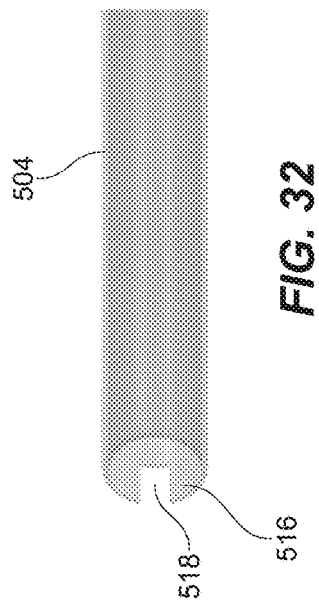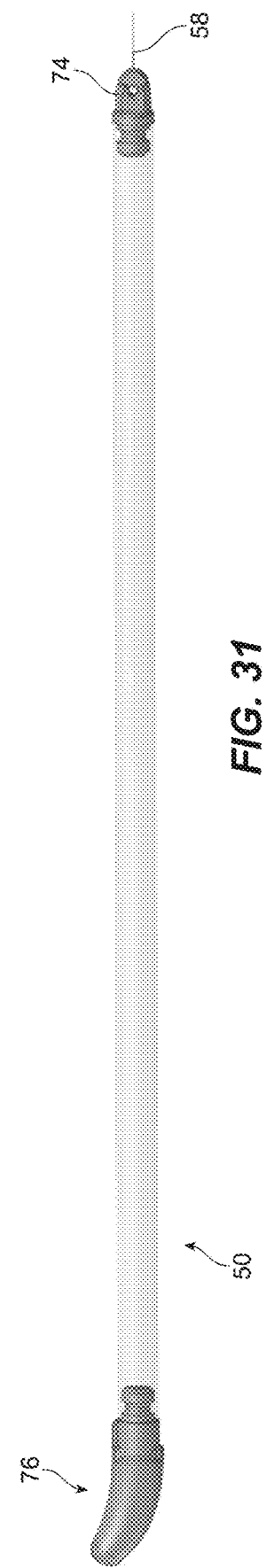

Test Protocol

- Three BU sensors was fabricated using the following:
  - Flex PCB Rev 2, Firmware V3.0.2
  - Silicone end caps and septa
  - RTV adhesive
  - Curved Spine not welded to the battery and no spacer.
  - Double lumen tubes and Silicone Oil
- During injection of silicone oil, the pressure was adjusted to the following
  - Sensor 1: 1142 cmH2O
  - Sensor 2: 918 cmH2O
  - Sensor 3: 836 cmH2O

- Tested in Human Bladder model
  - Step 0 to 320 and 320 to 0 cmH2O (3 s width)
  - Step 320 to 0 cmH2O 5 cmH2O intervals
  - Sweep 0 – 30 Hz
  - Square 0.1 Hz and amplitude 200 cmH2O

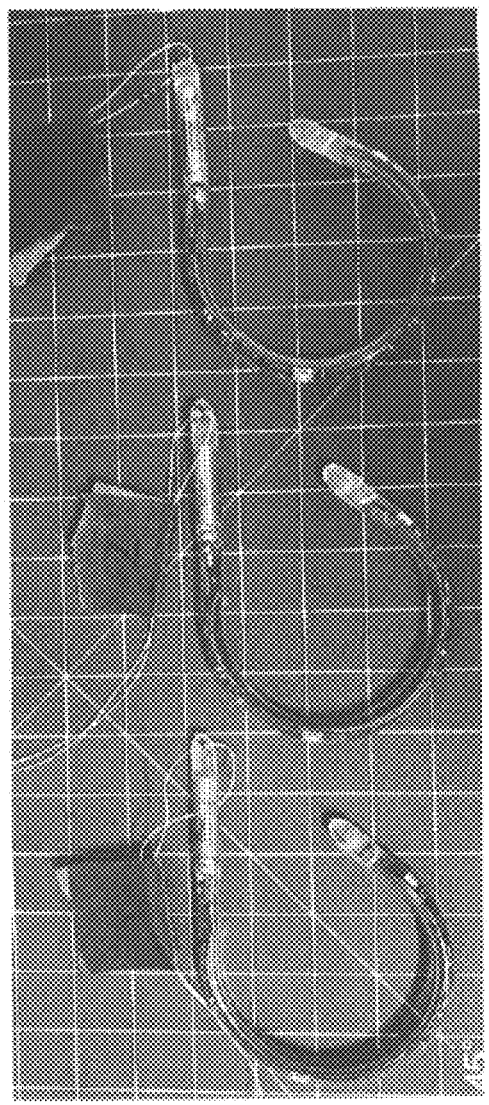

*FIG. 35*

Test Protocol (Air Injection)

- After Testing the sensors as described in the previous section, air was injected to the sensor until the pressure measured by the sensor reaches the following values:

- Sensor 1: 1237 cmH2O
  - Sensor 2: 1223 cmH2O
  - Sensor 3: 1203 cmH2O

- Considering the initial pressure of the sensors, Sensor 1 has the least amount of air bubbles and Sensor 3 has the most.

- Tested in Human Bladder model (Results in Previous section)
  - Step 0 to 320 and 320 to 0 cmH2O (3 s width)
  - Step 320 to 0 cmH2O 5 cmH2O intervals
  - Sweep 0 – 30 Hz
  - Square 0.1 Hz and amplitude 200 cmH2O
  - UDS simulation

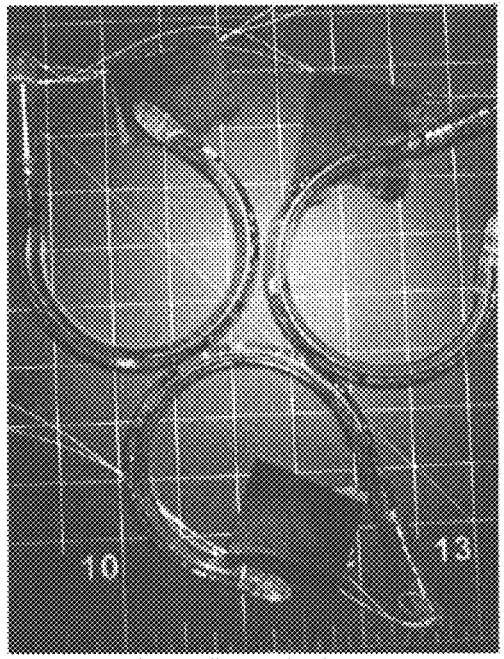

*FIG. 36*

Test Protocol (Pressure Drift After Fabrication)

- After Testing the sensors as described in the previous section, silicone oil was injected to Sensor air was injected to the Sensor 3 until the pressure measured by the sensor reaches the following values:
  - Sensor 1: 1381 cmH2O
  - Sensor 3: 1332 cmH2O
- The sensors was left over night (~16 hrs) at room temperature while recording the pressure.

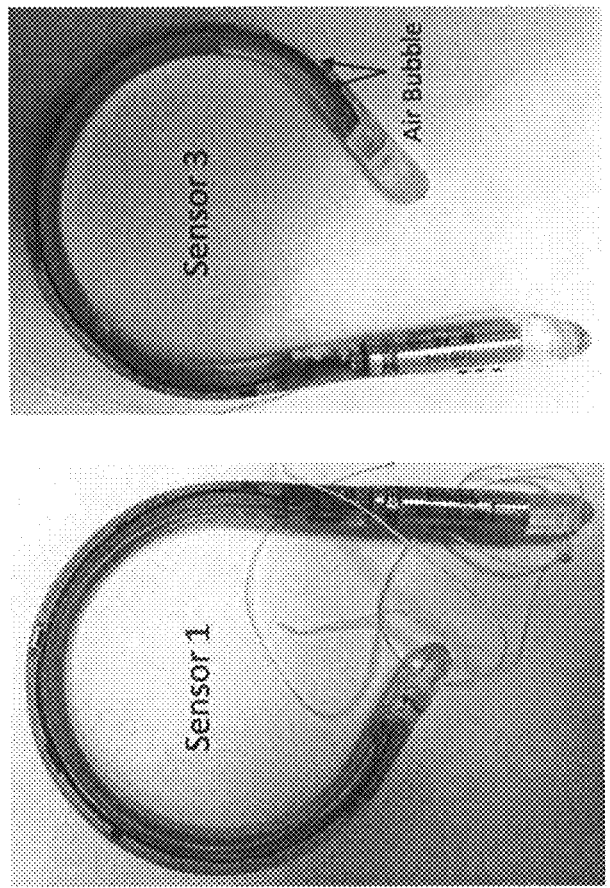

*FIG. 37*

Test Protocol (High Pressure)

- Three BU sensors was fabricated using the following:
  - Flex PCB Rev 2, Firmware V3.0.2
  - Silicone end caps and septa
  - RTV adhesive
  - Curved Spine not welded to the battery and no spacer.
  - Double lumen tubes and Silicone Oil
- During injection of silicone oil, the pressure was adjusted to the following
  - Sensor 4: 1232 cmH2O
  - Sensor 5: 1191 cmH2O
  - Sensor 6: 1129 cmH2O

- Tested in Human Bladder model
  - Step 0 to 320 and 320 to 0 cmH2O (3 s width) (Note: Sensor 5 stopped working after this test)
  - Step 320 to 0 cmH2O 5 cmH2O intervals
  - Sweep 0.1 – 3 Hz
  - Square 0.1 Hz and amplitude 200 cmH2O
  - Simulated UDS

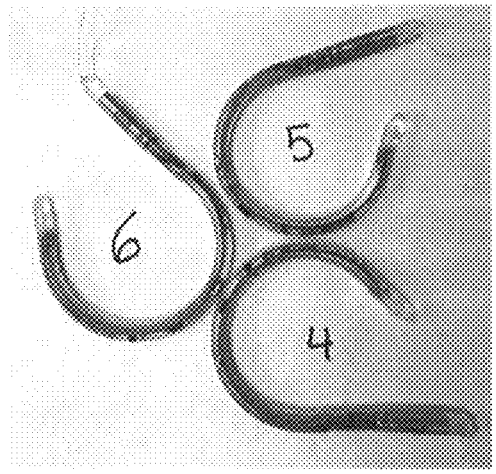

*FIG. 38*

Test Protocol (Temperature Change)

- After the previous test (1 day) sensor 4 and 6 these sensor was used for temperature effect testing.
- The pressure was measured on the bench as:
  - Sensor 4: 1263 cmH2O
  - Sensor 6: 1109 cmH2O
- Needs to be identified why the pressure of the sensors was increased after the previous testing.

- Tested in Human Bladder model
  - @ Room Temperature
    - Step 0 to 320 and 320 to 0 cmH2O (3 s width) (Note: Sensor 5 stopped working after this test)
    - Step 320 to 0 cmH2O 5 cmH2O intervals
    - Sweep 0.1 – 15 Hz
    - Square 0.1 Hz and amplitude 200 cmH2O
  - @ 37 C
    - Step 0 to 320 and 320 to 0 cmH2O (3 s width) (Note: Sensor 5 stopped working after this test)
    - Step 320 to 0 cmH2O 5 cmH2O intervals
    - Sweep 0.1 – 15 Hz
    - Square 0.1 Hz and amplitude 200 cmH2O
  - Temperature ramp from room temperature to 37 C. The HBM valve was left open
    - Constant open HBM pressure (Only Sensor 6)

*FIG. 39*

Test Protocol (Temperature Change, Repeat)

- a BU sensors was fabricated using the following:
  - Flex PCB Rev 2, Firmware V3.0.6
  - Silicone end caps and septa
  - RTV adhesive
  - Curved Spine not welded to the battery and no spacer.
  - Single lumen tubes and Silicone Oil
- During injection of silicone oil, the pressure was adjusted to the following
  - Sensor 8: 1259 cmH2O
- Temperature ramp from room temperature to 37 C. The HBM valve was left open. Next the heater was turned off until HBM cools down to 29 C.

*FIG. 40*

Test Protocol (Temperature Change, Repeat, Cycles)

- a BU sensors was fabricated using the following:
  - Flex PCB Rev 3, Firmware V3.0.7
  - Silicone end caps and septa
  - RTV adhesive
  - Curved Spine not welded to the battery and no spacer.
  - Single lumen NuSil tubes and Silicone Oil Med-460
- During injection of silicone oil, the pressure was adjusted to the following
  - Sensor 10: 1264 cmH2O
- Temperature ramp from room temperature (23 C) to 37 ± 1 C. Stayed at 37 ± 1 C for 20 minutes. Next the heater was turned off until HBM cools down to 27 ± 1 C. Again, the Temperature was turned on to reach 37 ± 1 C, stayed at 37 ± 1 C for 20 minutes, and turned off. The HBM valve was left open through out the experiment.

*FIG. 41*

Test Protocol (Temperature Cycle Hotplate)

- A BU sensors was fabricated using the following:
  - Flex PCB Rev 3, Firmware V3.0.7
  - Silicone end caps and septa
  - RTV adhesive
  - Curved Spine not welded to the battery and no spacer.
  - Single lumen NuSil tubes and Silicone Oil Med-460
- During injection of silicone oil, the pressure was adjusted to the following
  - Sensor 12: 1255 cmH2O
- The sensor was placed inside a beaker filled with water on a hotplate. The temperature raised to ~40 C and brout back to room temperature 3 times.
- Bubbles formed after increasing the temperature.

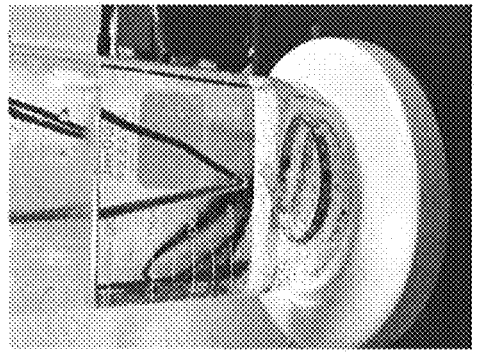

FIG. 42

Test Protocol (24 Hours HBM Test)

- a BU sensors was fabricated using the following:
  - Flex PCB Rev 3, Firmware V3.0.7
  - Silicone end caps and septa
  - RTV adhesive
  - Curved Spine not welded to the battery and no spacer.
  - Single lumen NuSil tubes and Silicone Oil Med-460
- During injection of silicone oil, the pressure was adjusted to the following
  - Sensor 12: 1280 cmH2O
- The following waveform was run on the HBM for 24 Hours and BU and Omega sensor was measured.

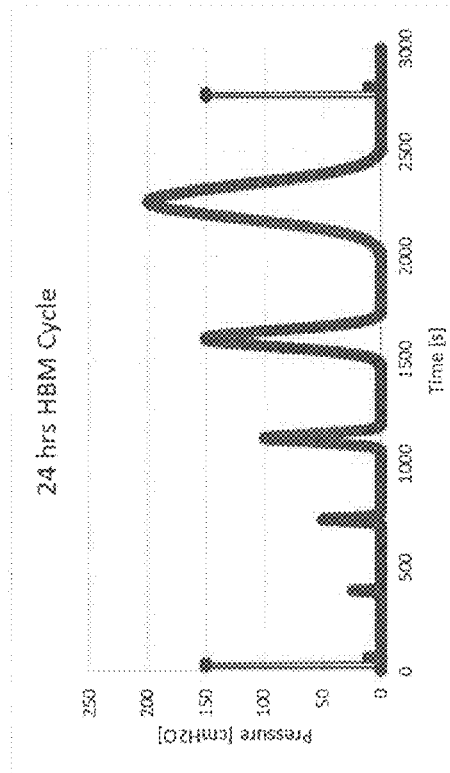

*FIG. 43*

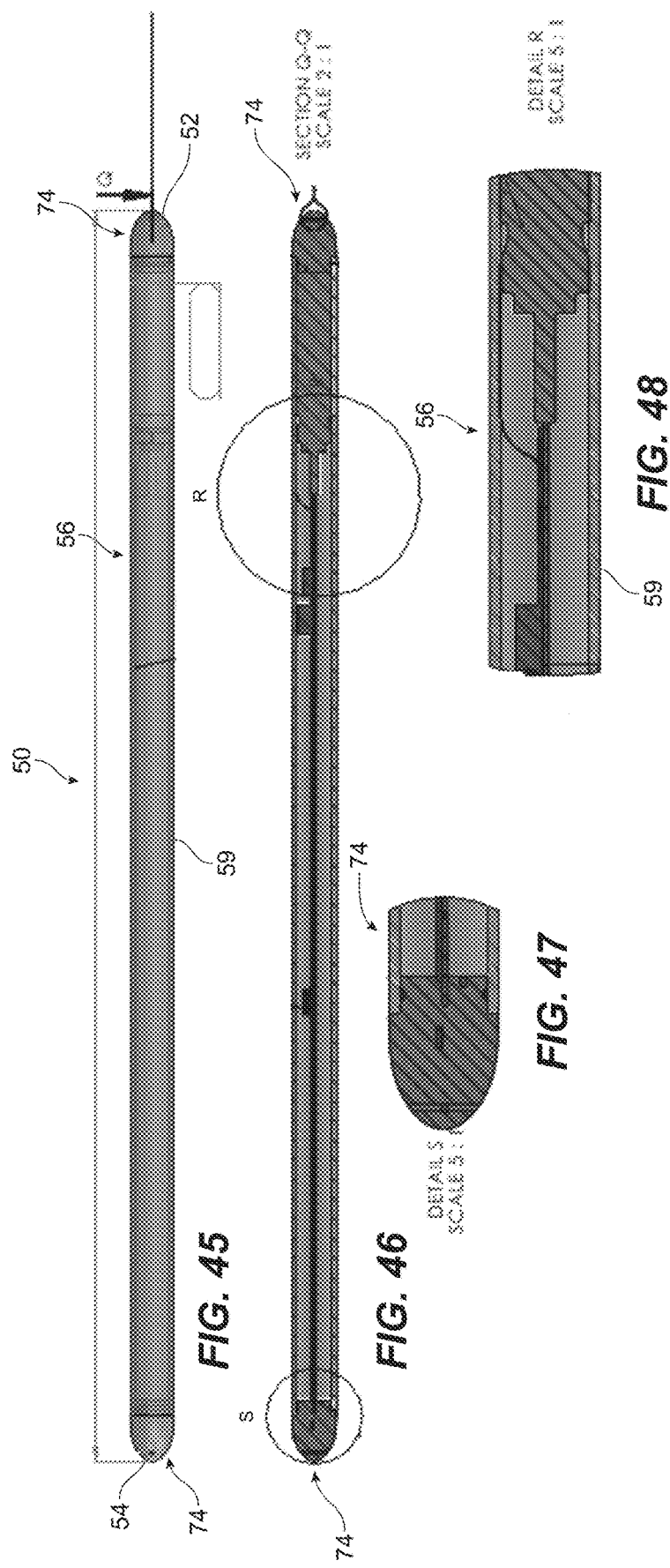

Silicone Extrusions
- Single Lumen
- Dual Lumen
- Pre-cut to length

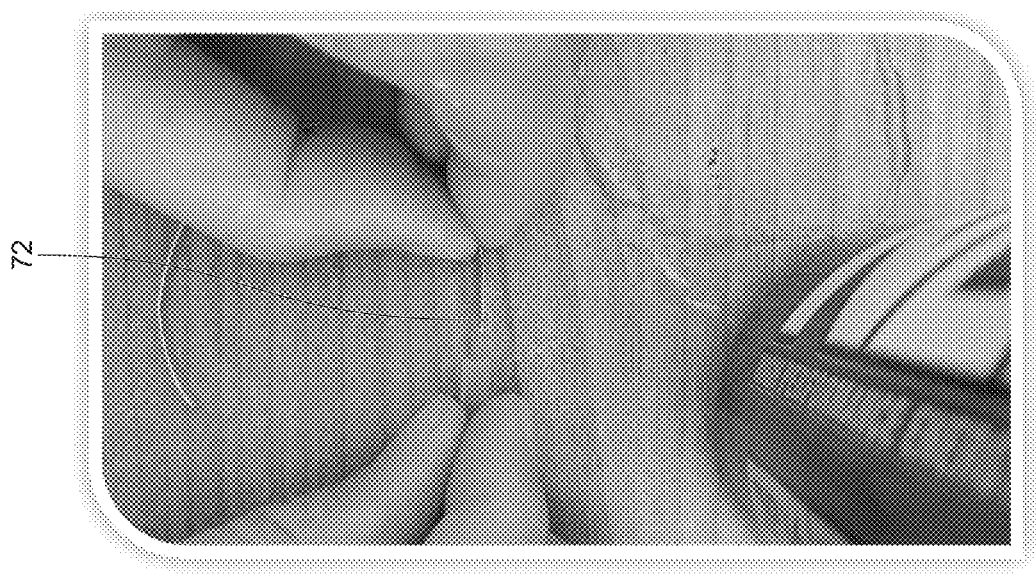
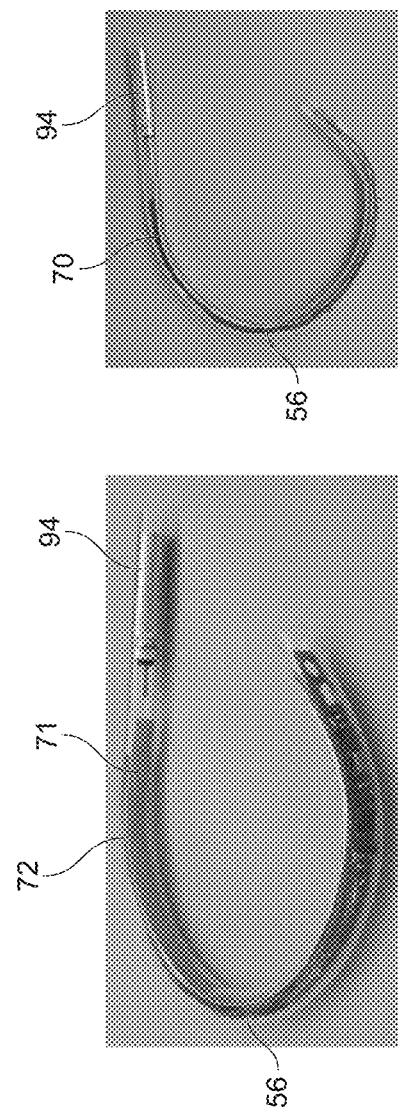
Tubing Prototype
- Both the PC Board and Spine slide easily into the silicone extrusion
- The battery has significantly more resistance and may work as an anchor point for the assembly.
*FIG. 51B*
*FIG. 51A*
*FIG. 50*

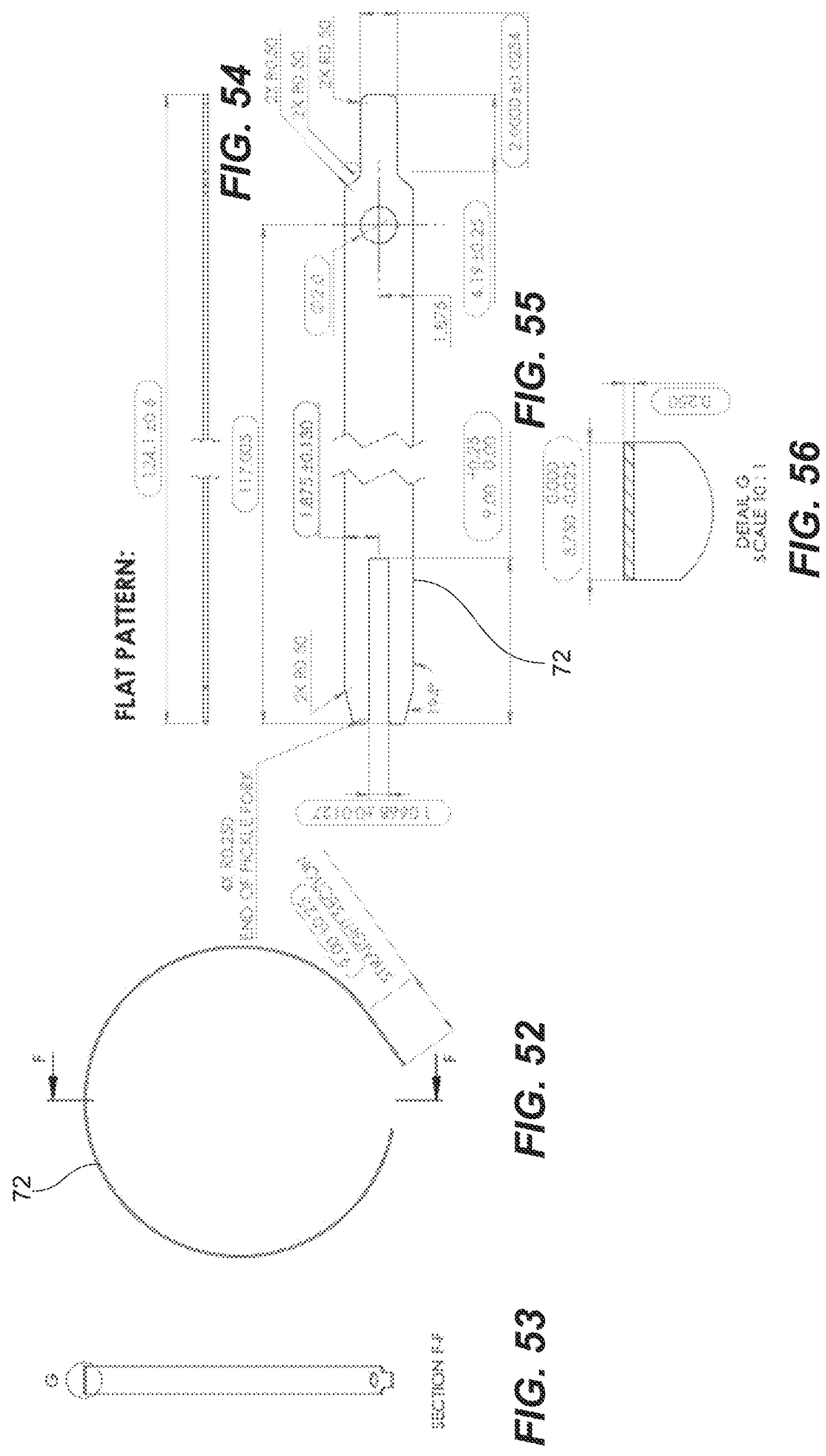

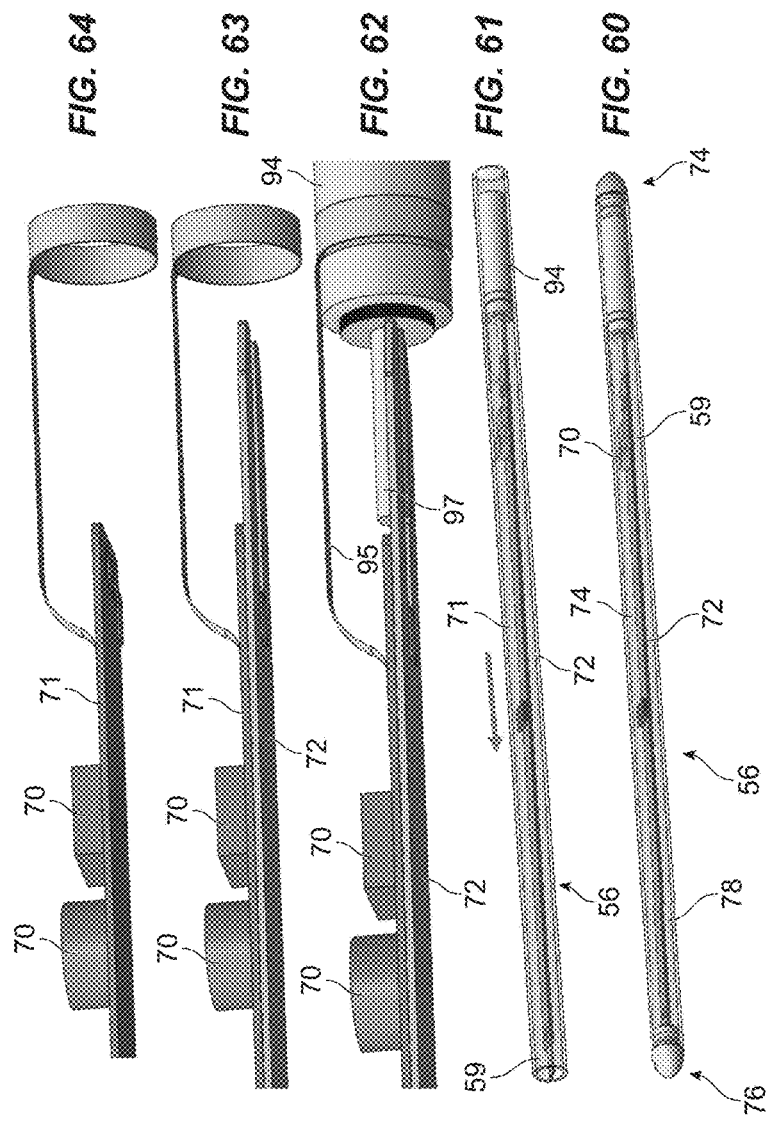

| | Sample 1 | Sample 2 | Sample 3 |
|---|---|---|---|
| Needle to inject mineral oil | 25 Ga | 22 Ga | 22 Ga |
| Needle to let air escape | 30 Ga | 25 Ga | 25 Ga |
| Pressure Change? | No pressure change | Pressure change | N/A (did not sit overnight) |
| Leak? | No leak | Leak | Leak |
| Pictures | 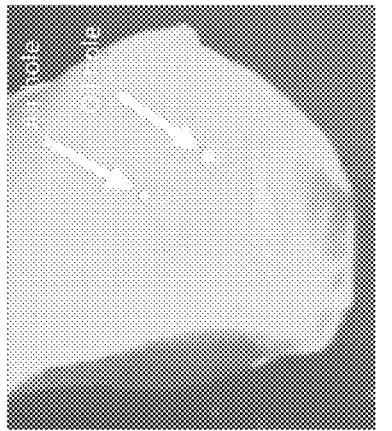 End 1 End 2 | 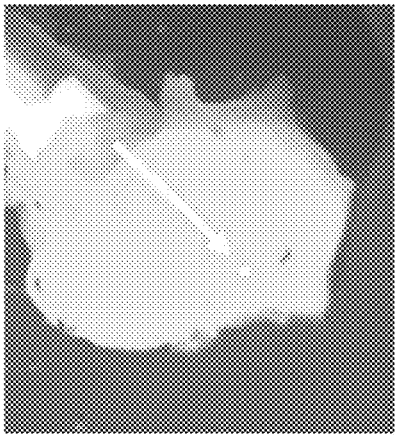 Leak one end only | 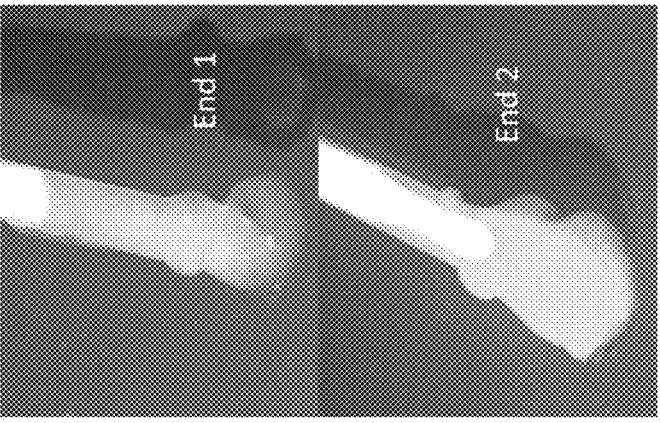 Leak one end only |
FIG. 69

Catheter Flexibility

Tipping

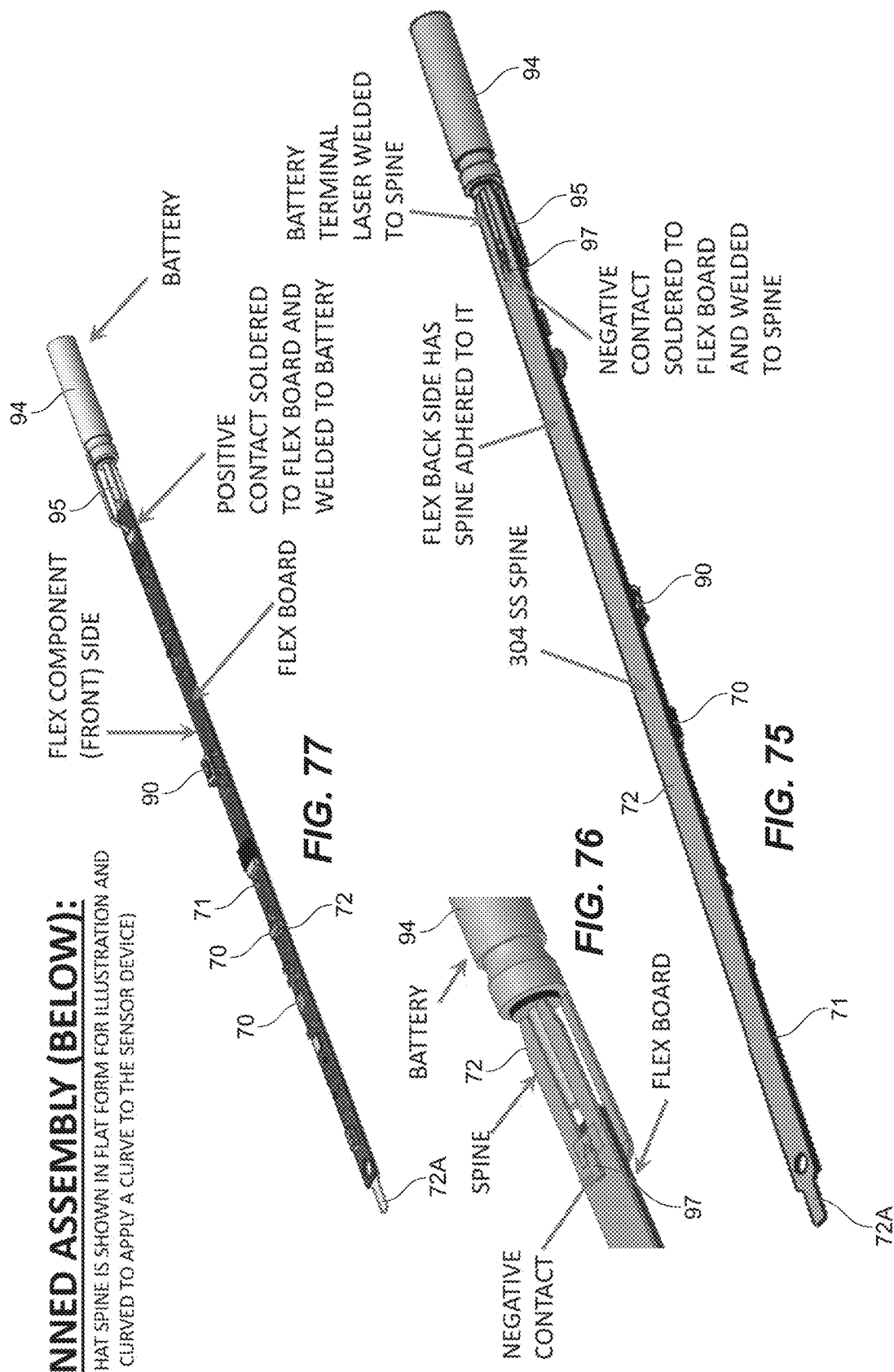

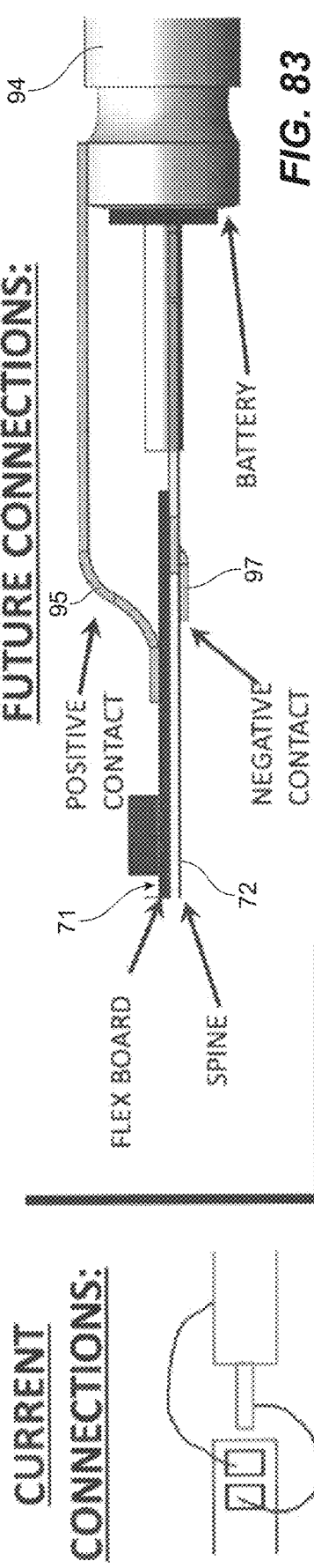
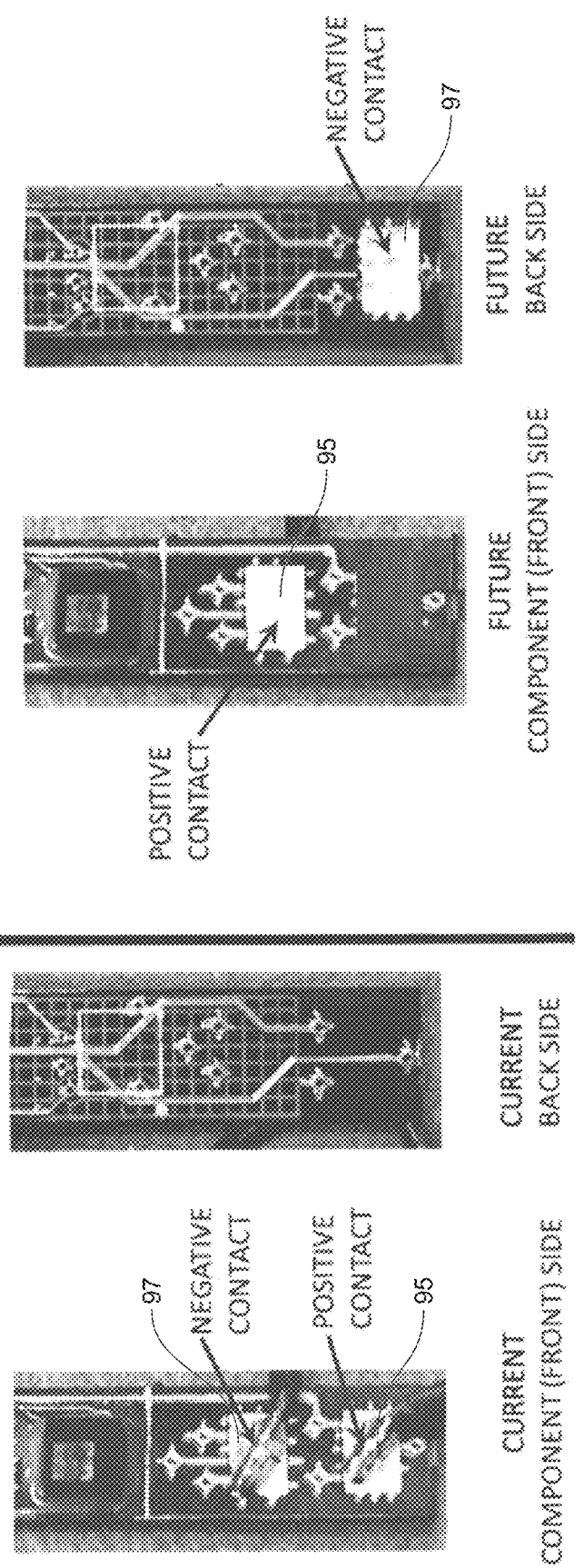
FIG. 79
FIG. 80
FIG. 81
FIG. 82
FIG. 83

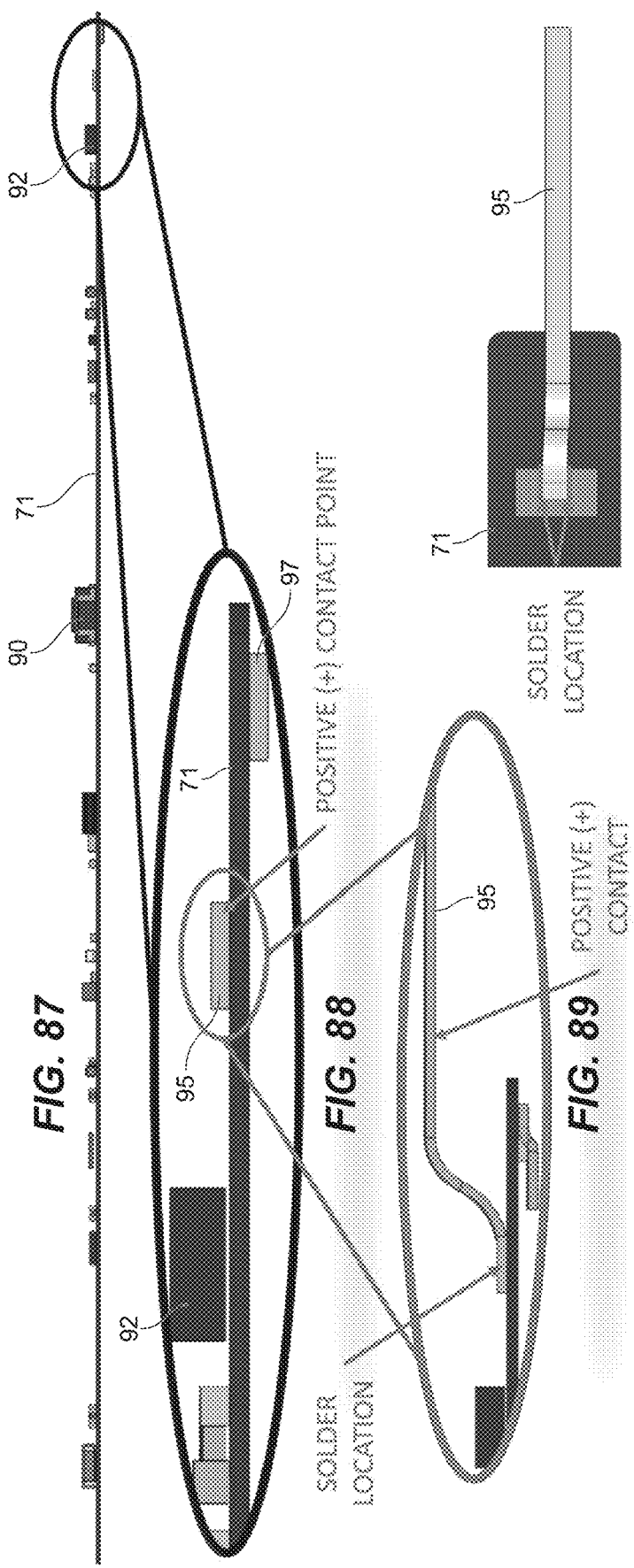

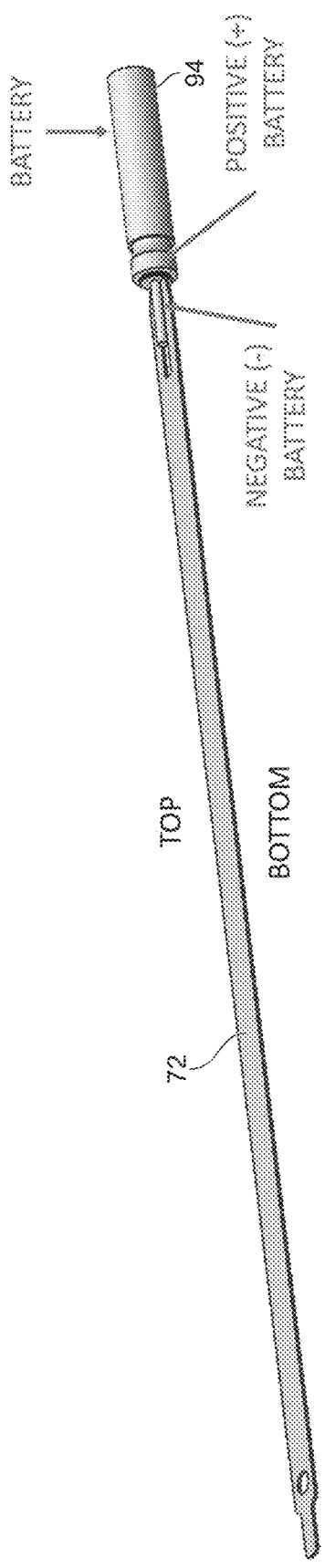
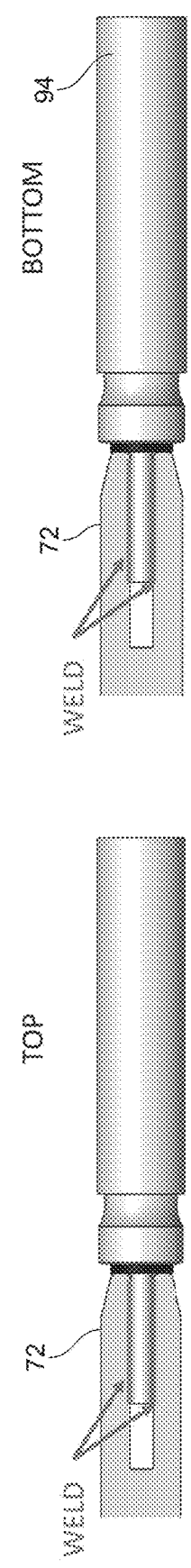
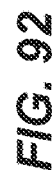
WELDING BATTERY AND SPINE
FIG. 90
FIG. 91
FIG. 92

PLACE DISTAL ENDCAP PARTIALLY ONTO THE SILICONE EXTRUSION

APPLY SILICONE ADHESIVE COMPLETELY AROUND THE ENDCAP VALLEY

PUSH ON DISTAL ENDCAP UNTIL IT HITS A HARD STOP AND LEAVE TO DRY FOR 24H OR PLACE IN OVEN AT 150°F FOR 2 HOURS

Septas

- Fill in mineral oil most of the way with large needle (curved configuration)
- Glue in bottom piece of endcap
- Let dry (fully sealed)
- Glue in septa
- Glue in top piece of endcap
- Fill the rest of the way with smaller needle

*FIG. 101*
*FIG. 100*
Fluid Testing
- Mineral Oil:
  - Citation 200
    - Viscosity: 207.4
- Silicone Oil
  - MED-460
    - Viscosity: 350

Spine & Endcap Interaction

- Inserting the Spine into the distal endcap provided a significant amount of stiffness for the distal end of the sensor
- This is nice to have for insertion of the sensor

SPINE SUPPORTED IN DISTAL ENDCAP

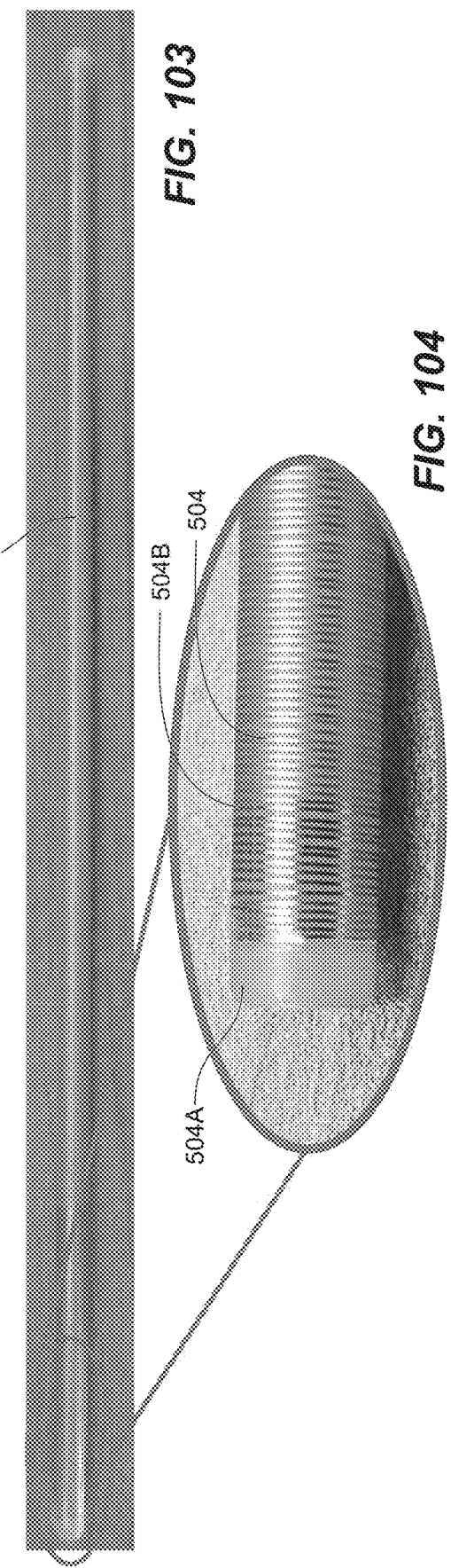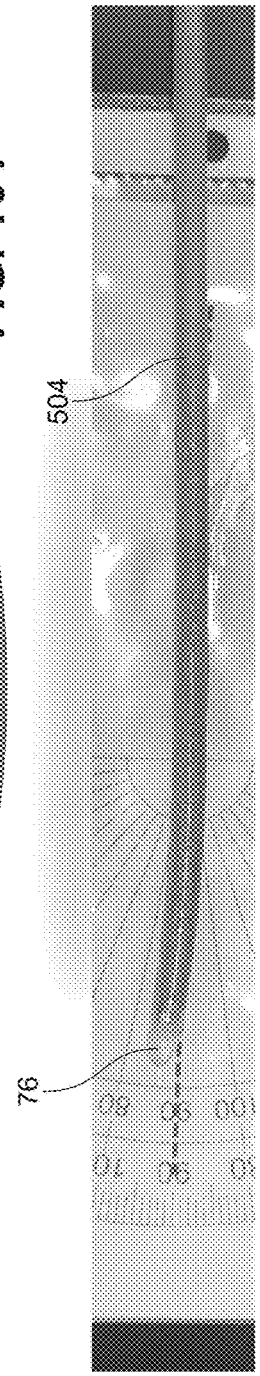
FIG. 103
FIG. 104
FIG. 105

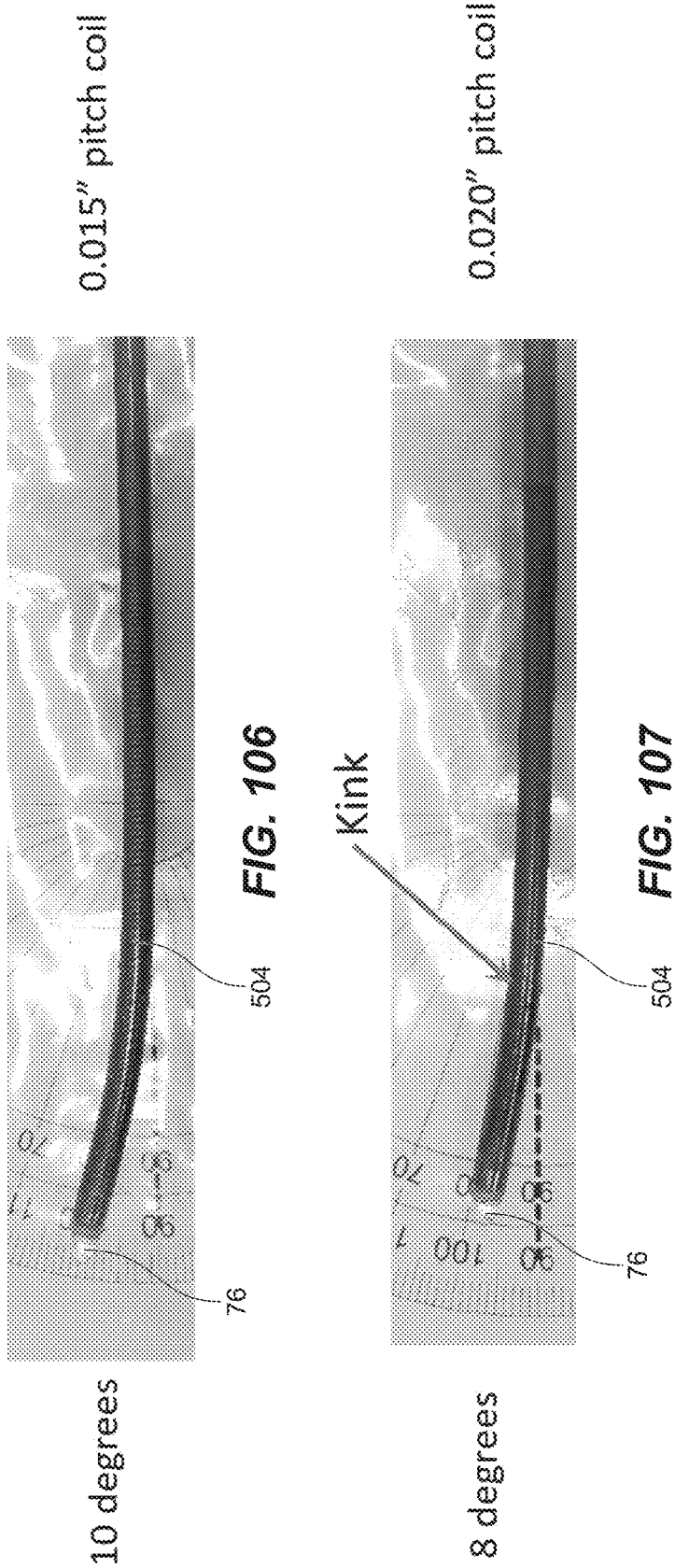

Procedure Forces

- Force to pull Sensor into the Insertion Tool (Using KY Jelly Lubricant)
  - Average Force: 1.18 lbf
- Force to push Sensor out of the Insertion Tool
  - Average Force: 0.83 lbf
- Force to Pull Sensor out of the bladder model
  - Average Force: 0.36 lbf

Spine Flexion Analysis
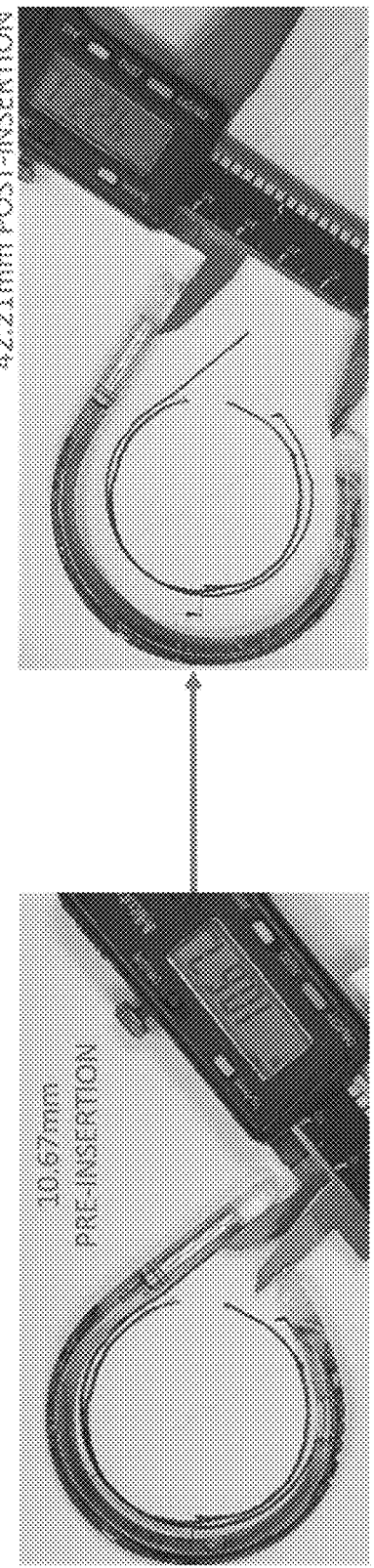
FIG. 109 Sample #2 (0.010" Thick) @ 5min in Insertion Tool
FIG. 110
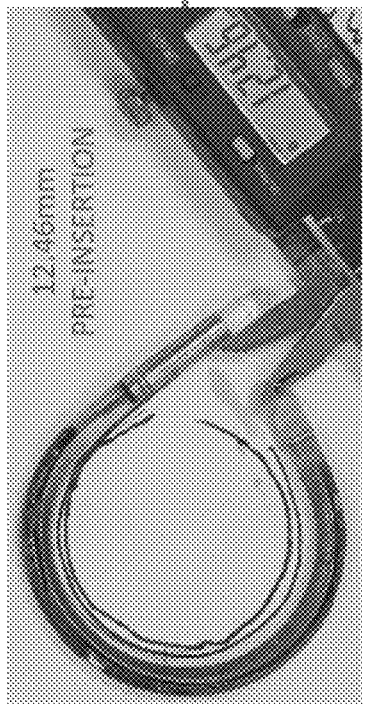
FIG. 111 Sample #1 (0.010" Thick) @ 20 min in Insertion Tool
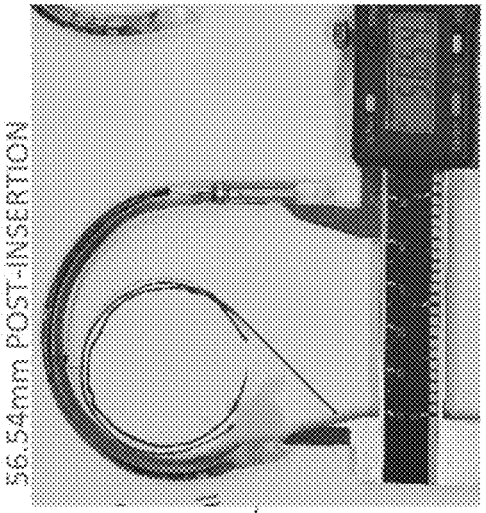
FIG. 112

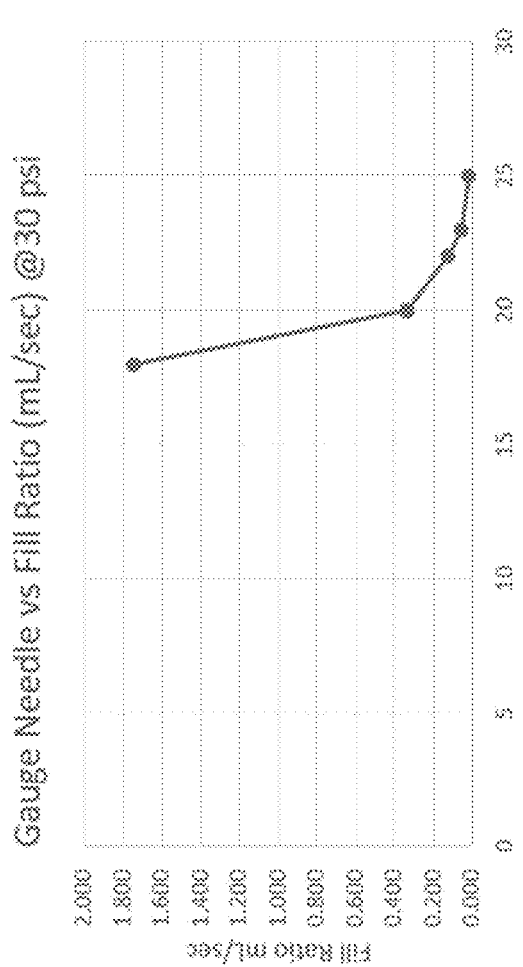
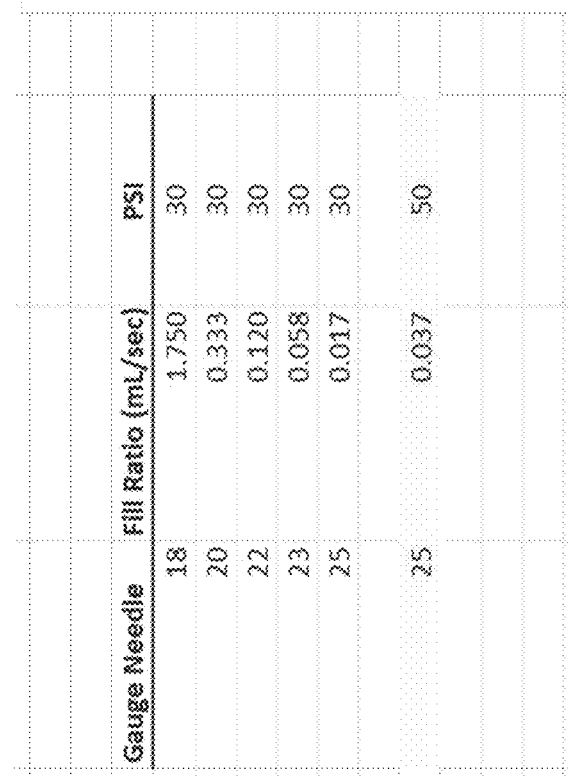
FIG. 118

BRAIDED INSERTION TOOL

20 PPI Braid Wire

35 PPI Braid Wire

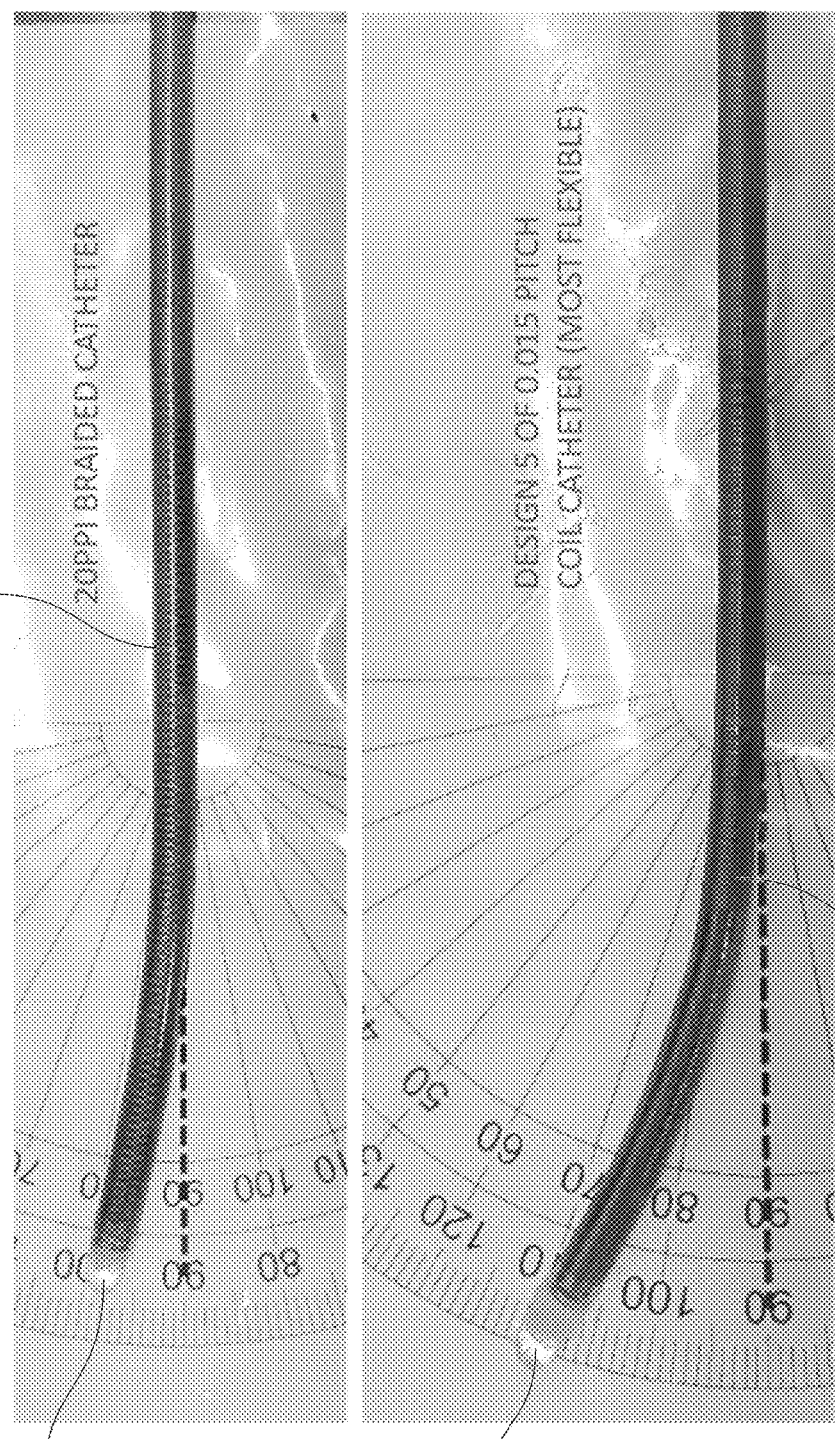

Tip Design

- Spiked tip on the distal end of the spine
- Heat-stake spine into the Distal Tip Spacer

Material/Oil Testing (in mm)

| Sample # | Material | Soaking Media (14 hours @ 37 C) | Before Immersion OD | Before Immersion Length | After Immersion OD | After Immersion Length | Delta OD | Delta Length |
|---|---|---|---|---|---|---|---|---|
| 1 | 80A Pellethane | Mineral Oil | 2.78 | 150.75 | 2.81 | 151.5 | 0.91% | 0.50% |
| 2 | 70A Pellethane Thin Wall | Mineral Oil | 2.45 | 150.5 | 2.48 | 152 | 1.04% | 1.00% |
| 3 | 90A Pellethane (Fluid Tubing) | Mineral Oil | 3.59 | 150.5 | 3.59 | 151 | 0.14% | 0.33% |
| 4 | 55D Pellethane (Blue) | Mineral Oil | 4.06 | 150.5 | 4.06 | 151 | 0.00% | 0.33% |
| 5 | Qflex (Hard) | Mineral Oil | 4.74 | 151 | 4.74 | 151.5 | 0.00% | 0.33% |
| 6 | Dual Lumen Silicone Tube | Mineral Oil | 4.97 | 150.25 | 5.06 | 155.75 | 1.74% | 3.66% |
| 7 | 35D Pebax | Mineral Oil | 6.10 | 150.25 | 6.08 | 155.25 | N/A* | 3.33% |
| 8 | Nylon 12 | Mineral Oil | 6.05 | 150 | 5.86 | 150.5 | N/A* | 0.33% |
| 9 | Silicone Tube | MED-400 | 4.99 | 150.5 | 5.01 | 150.5 | 0.31% | 0.00% |

*FIG. 129*

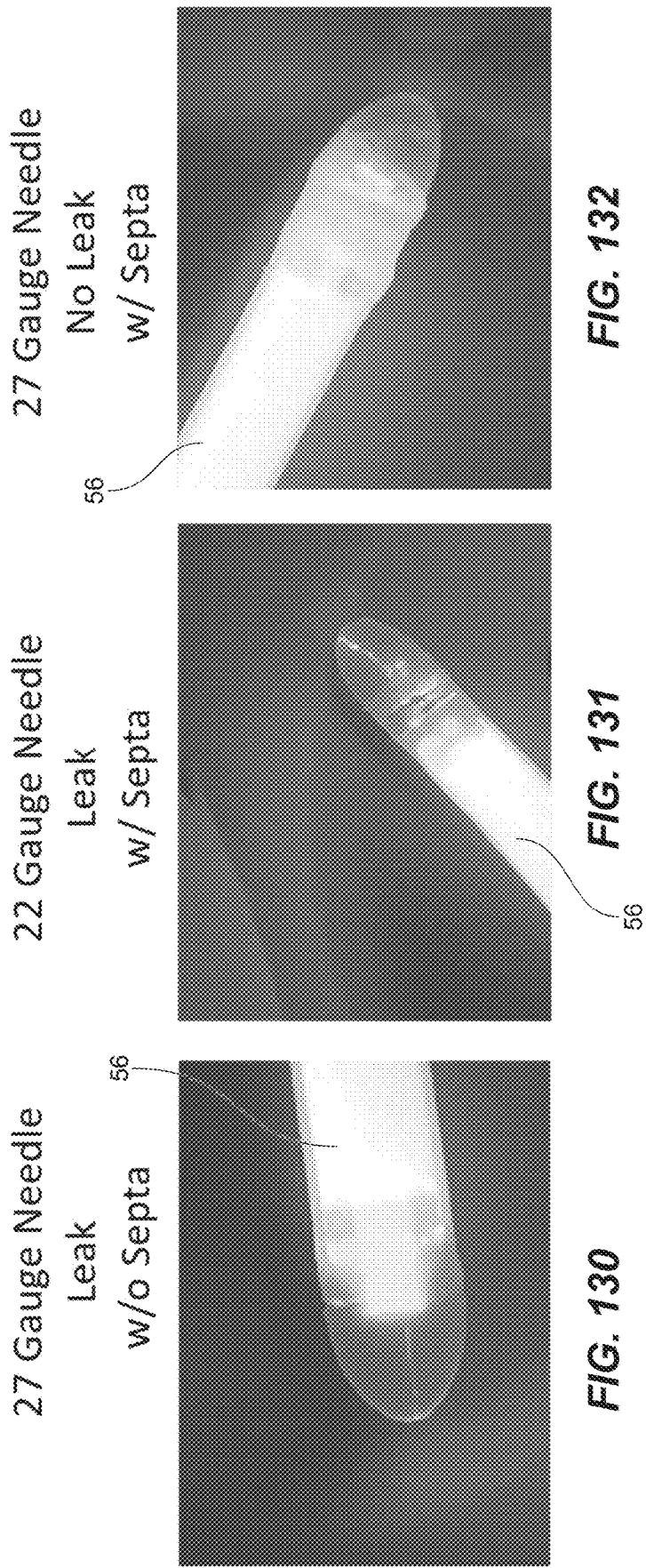

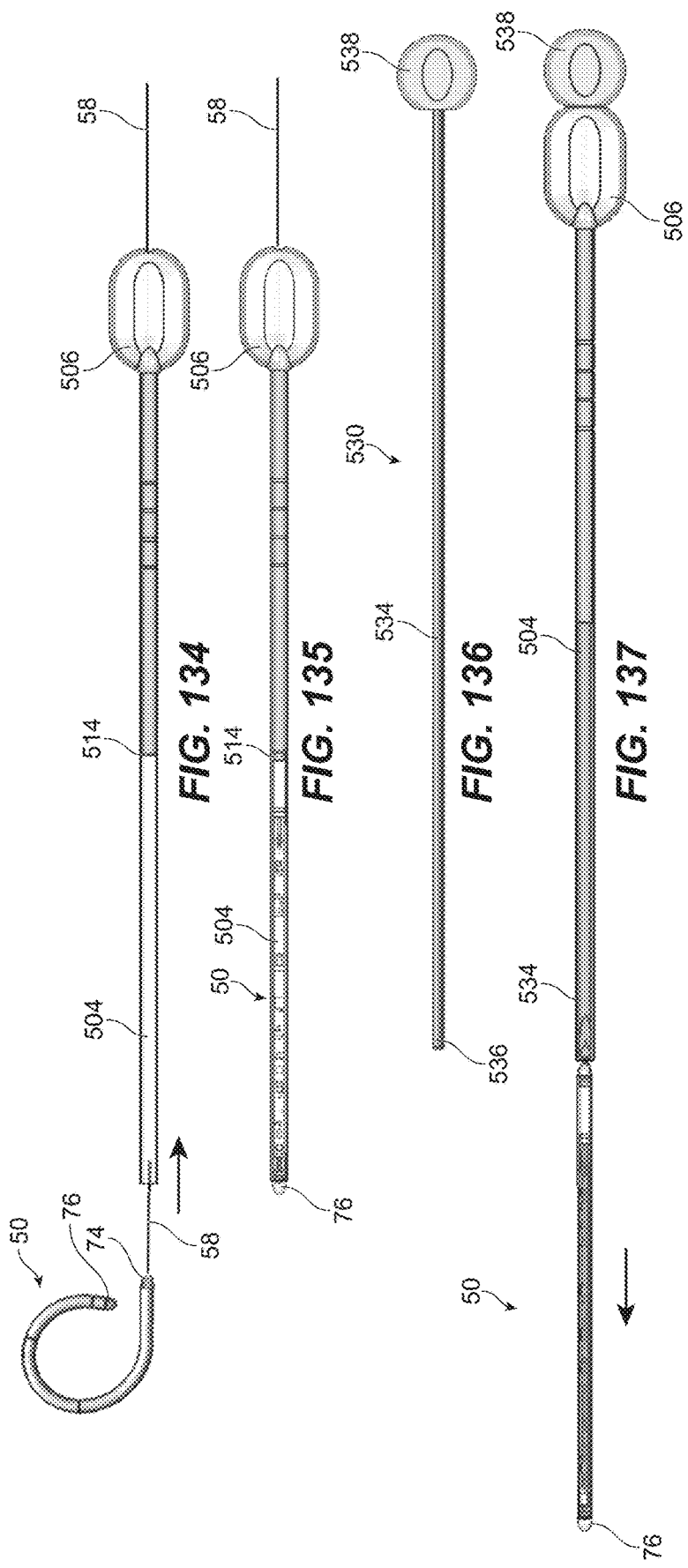

Distal Spacer for Spine

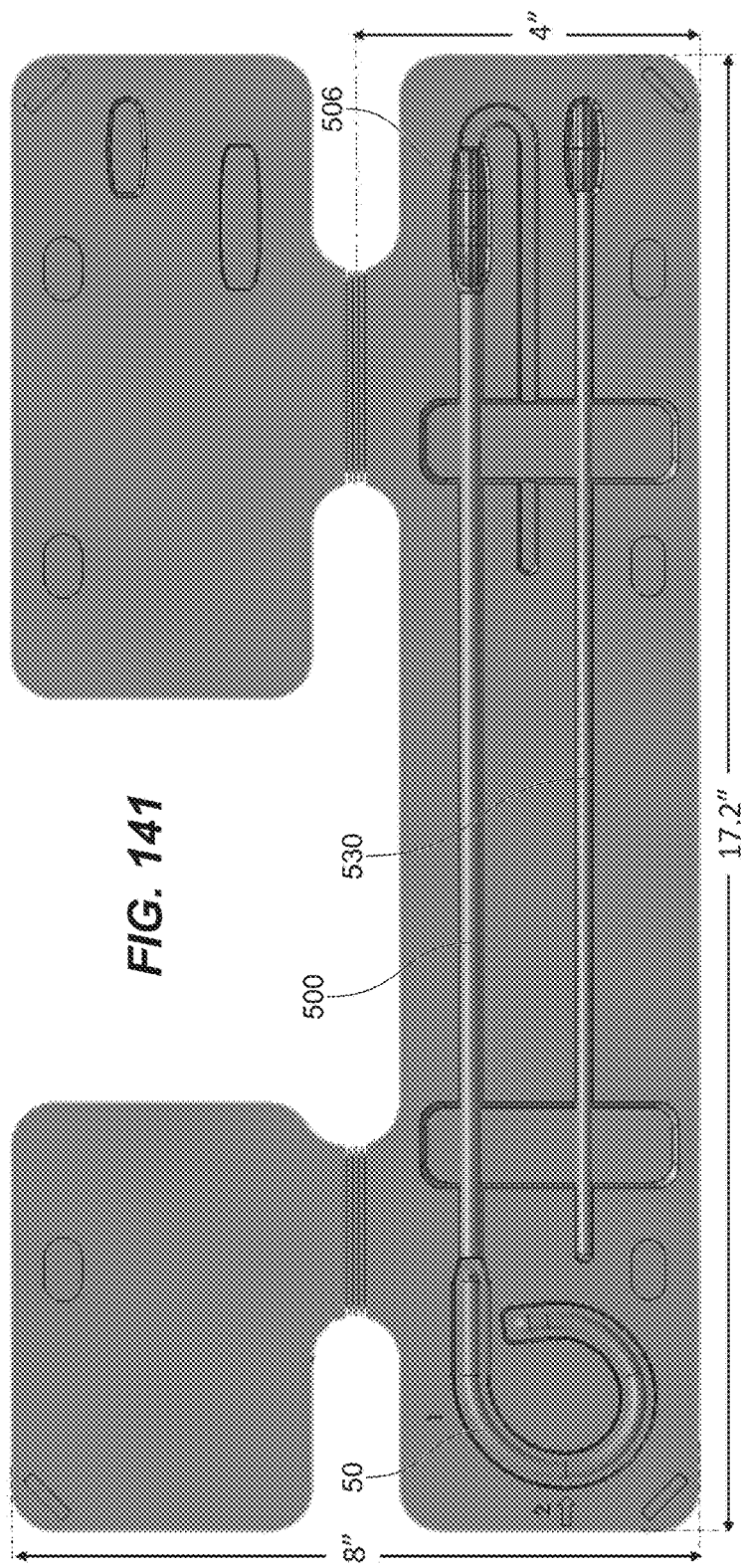
FIG. 141
FIG. 142
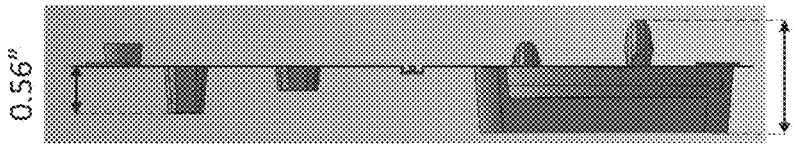
FIG. 143

Updated Proximal Tip Design

Updated to allow cystoscopic forceps to grip onto tip (if necessary)

Software (Phone – Tablet App)

| First | Last | MRN | Status | Last Activity | Time |
|---|---|---|---|---|---|
| James | | 12345678 | Active | Diary Entry | 12:45 |
| Derek | | 12345678 | Active | Uroflowmeter | 11:56 |
| Pemon | | 12345678 | Active | Sensor Insertion | 11:03 |
| Bryan | | 12345678 | Pending Interpretation | UDS | 4/3/2023 |
| Brittany | | 12345678 | Pending Interpretation | UDS | 4/2/2023 |
| Hamed | | 12345678 | Pending Interpretation | UDS | 4/2/2023 |
| Teresa | | 12345678 | Pending Interpretation | UFM | 4/2/2023 |
| Jake | | 12345678 | Pending Interpretation | UDS | 3/11/2023 |

*FIG. 161*

SYSTEMS AND METHODS FOR UROLOGICAL SENSING

CROSS REFERENCE TO RELATED APPLICATIONS

This application is a continuation of PCT/US2023/024881, filed Jun. 8, 2023, titled "SYSTEMS AND METHODS FOR UROLOGICAL SENSING", which claims priority to U.S. Provisional Patent Application Ser. No. 63/350,305, entitled "SYSTEMS AND METHODS FOR UROLOGICAL SENSING," filed Jun. 8, 2022, and also claims priority to U.S. Provisional Patent Application Ser. No. 63/447,765, entitled "SENSORS AND SOFTWARE FOR URODYNAMICS," filed Feb. 23, 2023. Each of the foregoing applications is incorporated herein by reference in their entirety.

BACKGROUND

Sensors for urological sensing that are positioned in the bladder are known. Yet there are areas in which these can be improved.

SUMMARY

A flexible sensor configured for use in a bladder is moveable from a first position in which it is configured to not be discharged or dislodged from the bladder to a second position in which it is configured to be inserted into the bladder. The sensor is preferably biased to the first position in which it is preferably circular or curved, but can also be in any geometric position that would inhibit discharge from the bladder, and it is physically moved to the second position in which it is preferably straight and cylindrical to enable passage through the urethra and into the bladder. The sensor is moved to the second position to be inserted into the bladder and after insertion the biasing of the sensor causes it to move back to its first position.

A sensor insertion tool may include an over sheath (or "sheath") and a push rod that fits inside of a lumen (or "first lumen") of the over sheath. The over sheath includes an outer wall and a lumen configured to receive the sensor when the sensor is in its second position. The over sheath lumen may have a first, distal section (or portion) with a distal cross-sectional area and a second, proximal section with a proximal cross-sectional area that is less than the first, distal cross-sectional area. When the sensor is positioned in the over sheath lumen, either by pushing or (preferably pulling it in) the sensor's proximal end is configured to be pulled through the first, distal section of the over sheath lumen but not through the second, proximal section because the second, proximal section is too small to receive the sensor's proximal end. Thus, the sensor's proximal tip butts against the beginning of the second, proximal section of the lumen and cannot advance farther. This stops the sensor from moving into the second, proximal section, which positions the sensor such that its distal end is outside of the distal end of the insertion tool and properly positioned to be rotated (if required), in order to be in the proper position to be pushed through the urethra and into the bladder. An interaction/engagement between the proximal end of the sensor and the edge of the second, proximal section of the sheath may be provided by a variety of symmetric or asymmetric shapes that engage and can enable translation of force rotationally whereby rotation of the sheath is translated to the sensor, which rotates the sensor and its distal end.

The distal end of the sensor may have one or more symmetric or asymmetric features designed to interlock with the distal end of the sheath, also to enable rotation of the sensor when the sheath is rotated. In one embodiment this structure, such as a key at the sensor's distal end, which is configured to be received in a structure, such as a keyway, on the distal end of the over sheath, so that the sensor and insertion tool are connected and can rotate in tandem before the sensor is deployed in the bladder. As mentioned, the proximal end of the sensor preferably has a structure or geometry that aligns with a structure or geometry of the second, proximal section of the insertion tool lumen, which assists the sensor and insertion tool to rotate in tandem prior to the sensor being deployed in the bladder.

In one embodiment, engagement features are used at the proximal and distal end of the sensor. In this embodiment the distance from the proximal to distal tip of the sensor may be aligned to the distance between the end of the sheath and the opening of the second lumen in the sheath. This helps to ensure proper translation of force rotationally between the sheath handle to the sensor. This structure also enables force translation linearly such that force can be reliably translated from the sheath handle through the sheath to the sensor.

One or both of the endcaps of the sensor, and preferably the proximal end cap, may be constructed in a manner that facilitates easy retrieval of the sensor using standard cystoscopic tools, such as a flexible cystoscope (endoscope) and flexible grasping forceps. This feature is useful in reducing the time required for clinicians to grasp the end of the sensor in the event the clinician prefers to remove the sensor via cystoscopy and not utilizing the removal string.

A handle may be positioned on the over sheath and a separate handle may be positioned on the push rod. To insert (or deploy) the sensor into the bladder, the sensor is positioned (preferably by pulling it into) into the lumen of the over sheath. The insertion tool is then moved into the urethra and positioned at a location, such as the opening to the bladder, at which the distal end of the sensor, which preferably has a coude shape, can move into the bladder through a male or female urethra. If a user (such as a technician or doctor) feels that the distal end of the sensor is not properly aligned at the bladder opening the insertion tool may be rotated, which in turn rotates the sensor and its distal tip. When the sensor is properly oriented for insertion, the user then pushes the push rod into the over sheath and it pushes the sensor into the bladder. Once free of the sheath and in the bladder the sensor moves back to its first position.

BRIEF DESCRIPTION OF THE DRAWINGS

FIG. 8-8B show side views of the sensors of FIGS. 1-3.

FIGS. 18-20 are close-up, partial top views of the sensor of FIGS. 12-17.

FIG. 21 is an alternate view of the sensor of FIG. 12.

FIG. 22 is a partial, enlarged view of the sensor of FIG. 21.

FIG. 28 is a partial, close-up, side view of the distal end of an insertion tool (or sheath) according to this disclosure showing a keyway configured to receive a key on the distal end of a sensor.

FIG. 29 is a rear view of a handle according to this disclosure, which shows an opening through which the push rod is inserted, wherein the opening leads to a lumen that has a rounded top and rounded bottom and straight sides.

FIG. 30 is a partial, side, cut away view of an insertion tool stem according to this disclosure showing a lumen with a first, distal portion having a first diameter and a second, proximal portion having a second diameter that is less than the first diameter.

FIG. 31 is a side view of the sensor of FIGS. 21-24 showing the proximal tip with removal string attached and the distal tip with coude design and not showing the electronics.

FIG. 32 is a partial, side perspective view of the distal end of an insertion sheath according to this disclosure showing a keyway configured to receive a key on the distal end of a sensor.

FIG. 33 is a partial, side view of an insertion tool with the proximal end of the sensor with a removal string attached positioned therein and extending into the lumen of the insertion tool.

FIG. 34 is a partial, assembled device according to this disclosure with a sensor positioned in an insertion sheath and a push rod extending from a housing.

FIG. 35 shows a test protocol and top views of sensors 1-3 that were used to perform the tests using the protocol.

FIG. 36 shows a test protocol and a top view of sensors 1-3 that were used to perform the tests according to the protocol.

FIG. 37 shows a test protocol and a top view of sensors 1 and 3 that were used to perform the tests according to the protocol.

FIG. 38 shows a test protocol and a top view of sensors 4-6 that were used to perform the tests according to the protocol.

FIG. 39 shows a test protocol run using sensors 4 and 6.

FIG. 40 shows a test protocol run on a sensor 8.

FIG. 41 shows a test protocol run on a sensor 10.

FIG. 42 shows a test protocol run on a sensor 12 and a side view of a beaker with water showing bubbles forming.

FIG. 43 shows a test protocol run on a sensor 12.

FIG. 45 is a side view of a sensor according to this disclosure.

FIG. 46 is a cross-sectional view of the sensor of FIG. 45 taken through lines Q-Q.

FIG. 47 is an enlarged view of the tip shown in detail S of FIG. 46.

FIG. 48 is an enlarged view of the section shown in detail T of FIG. 46.

FIG. 50 shows a top, perspective view of a sensor with an outer sheath including the inner electronics and spine of a sensor according to this disclosure.

FIG. 51A is a top view of the sensor of FIG. 50.

FIG. 51B illustrates a spine being inserted into an outer sheath of a sensor.

FIGS. 52-56 show various views of a sensor spine according to this disclosure.

FIGS. 60-64 show side, perspective views of aspects of the assembly process for a sensor according to this disclosure.

FIG. 69 illustrates three examples of using needles to inject oil, to allow oil to escape, and recording pressure changes and leaks.

FIGS. 75-77 show side, perspective views of the assembly of some internal components of a sensor according to this disclosure.

FIGS. 79-83 show various views of electrical contacts for use in a sensor according to this disclosure.

FIGS. 87-89 show various views of electrical components and soldering locations for a sensor according to this disclosure.

FIGS. 90-92 show side views and a side, perspective view of a battery and spine that indicate where welds are placed.

FIGS. 100-101 show mineral oil and silicone oil used in testing.

FIGS. 103-105 show side views of an insertion tool that can be used to retain and insert a sensor according to this disclosure.

FIGS. 106-107 show side views of a sensor inside of an insertion tool according to this disclosure with an 8° bend and 10° bend.

FIGS. 109-112 show side views of sensors in insertion tools and presenting a sensor spine flexion.

FIG. 118 shows charts of fill analysis of a sensor cavity.

FIGS. 121-122 show side views of a sensor inside of insertion tools with no kinking detected.

FIGS. 124-126 show side, partial perspective views of a sensor with a distal tip, wherein the distal end of the spine is positioned in a soft spacer to avoid damage to the outer sheath.

FIG. 129 is a chart of material/oil testing using the mineral oil and silicone oil of FIGS. 100-101.

FIGS. 130-132 includes side views of distal ends of sensors with a septum and including leakage results.

FIGS. 134-137 show side views of a sensor, an insertion tool, and a push rod.

FIGS. 141-143 show an open, top view (FIG. 141) of a case for retaining a sensor, insertion tool, and push rod according to this disclosure, a side view (FIG. 143) of the case and a bottom view (FIG. 142) of the case.

Figure 152:
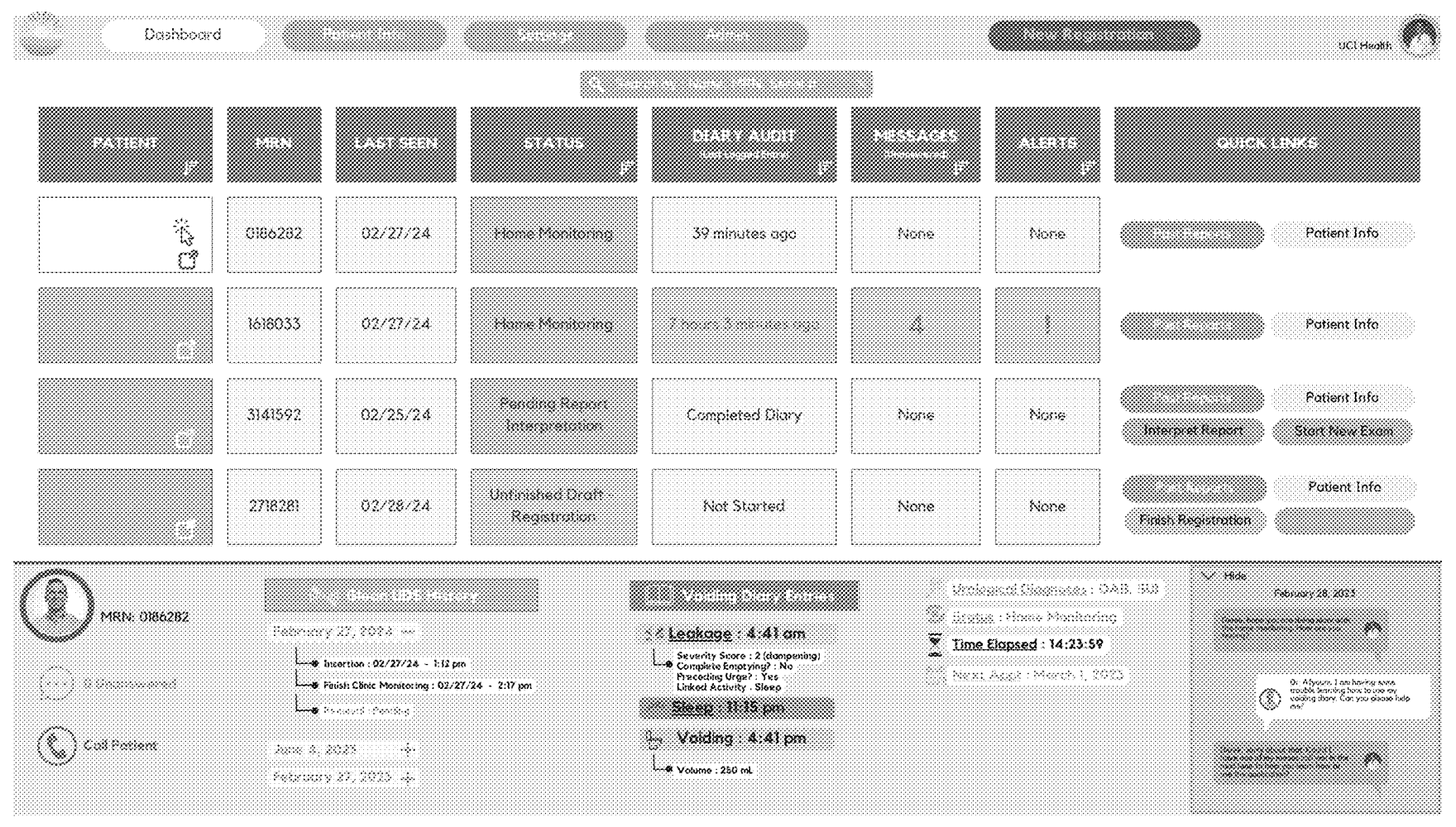

FIG. 152 shows a screen shot generated by a computer system that may be utilized with aspects of this disclosure.

Figure 153:
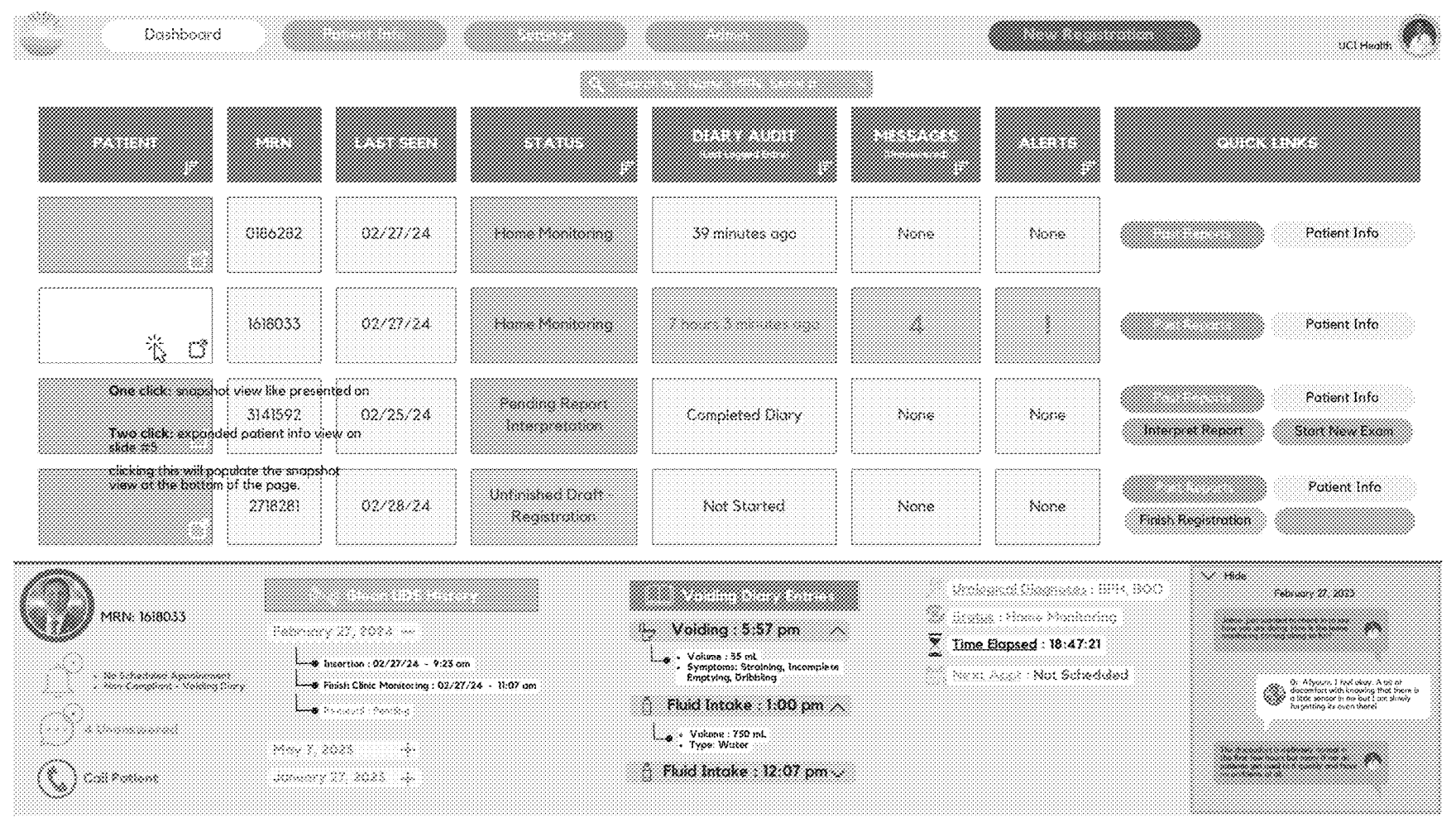

FIG. 153 shows an alternate screen shot generated by a computer system that may be utilized with aspects of this disclosure.

Figure 155:
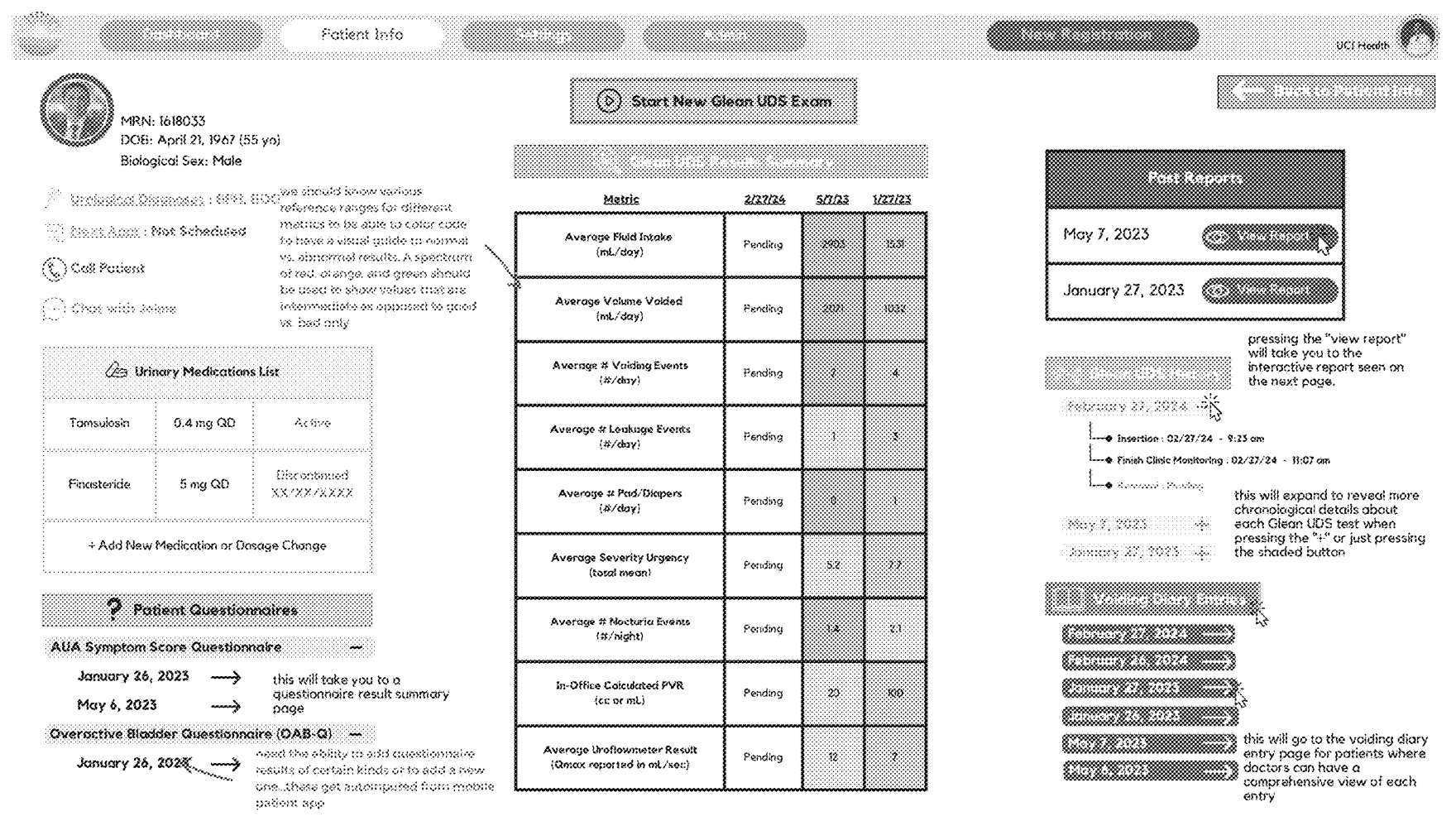

FIG. 155 shows an alternate screen shot generated by a computer system that may be utilized with aspects of this disclosure.

FIG. 161 shows an alternate screen shot generated by a computer system that may be utilized with aspects of this disclosure.

DETAILED DESCRIPTION

Sensor and Insertion Tool Example 1

Figures 1, 2, 3:
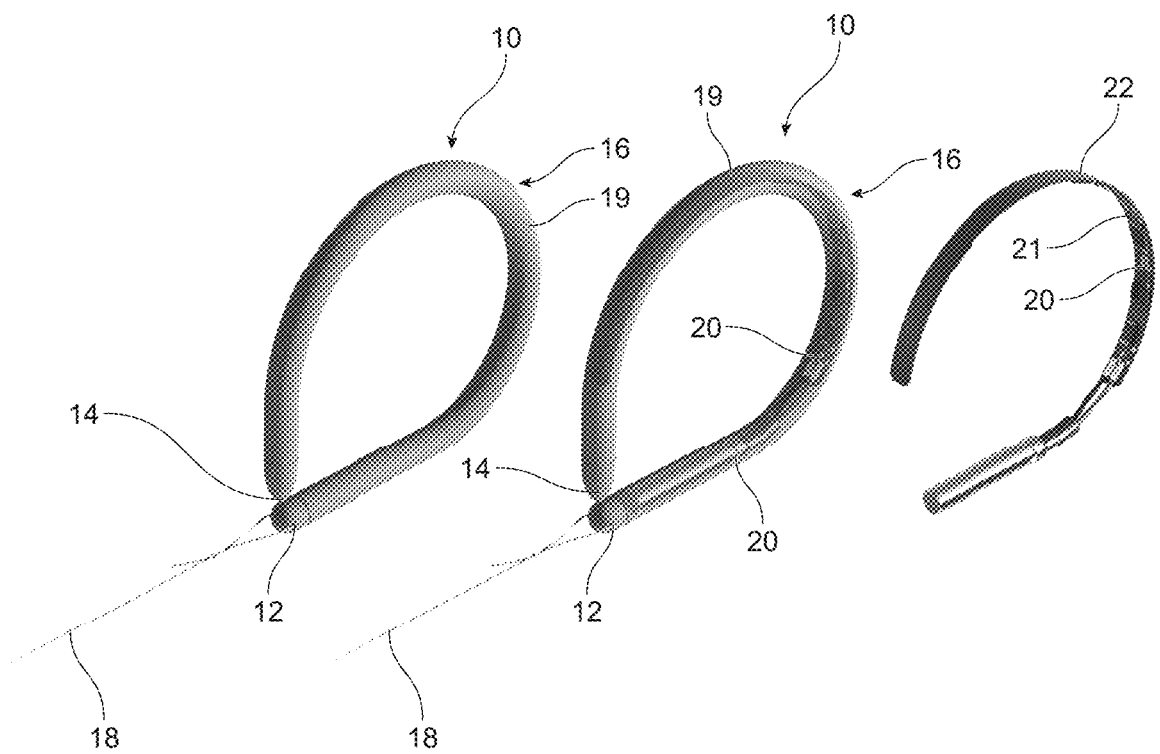
FIG. 1 is a side, perspective view of a sensor device according to this disclosure.
FIG. 2 is a side, perspective view of a sensor device of FIG. 1 with the electronics visible through the outer sheath.
FIG. 3 is a side, perspective view of the sensor device of FIG. 1 with the outer sheath removed and showing the electronics and spine.
Figure 3A:
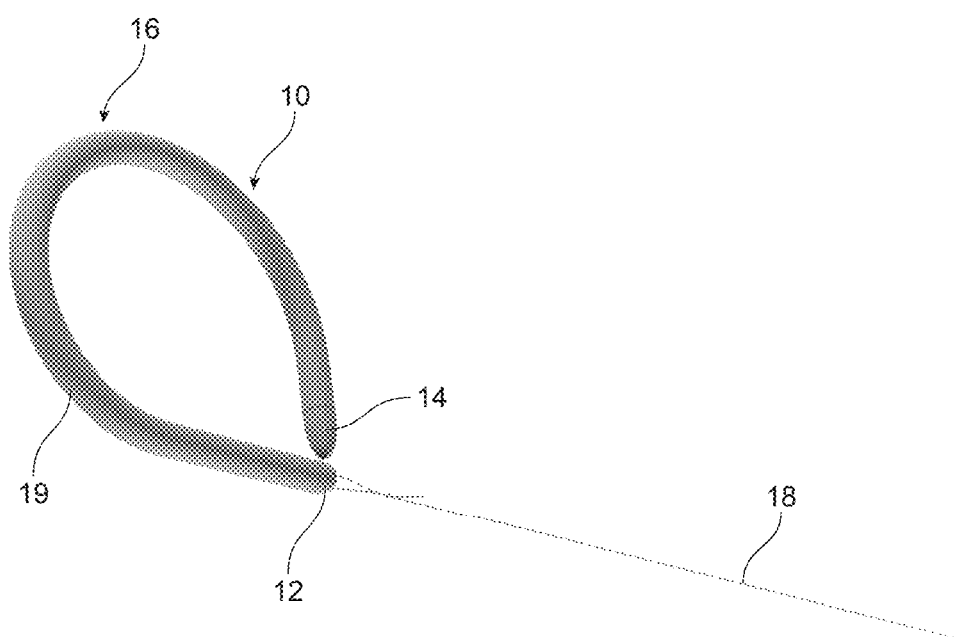
FIG. 3A is an alternate, side perspective view of the sensor of FIG. 1 with a
removal string attached.

Disclosed is a urodynamics system that may include one or more of the following components, as well as additional components: (1) a sensor as shown in FIGS. 1-2, and 9-10, which is in one embodiment a flexible silicone rubber tube with electronics inside, as shown in FIG. 3, to sense pressure and volume, (2) an insertion tool to deliver the sensor through the urethra and into the bladder.

FIGS. 1-3A illustrate a sensor 10 according to this disclosure. Sensor 10 has a proximal end 12, which is closest to the clinician prior to being inserted, a distal end 14, which is farthest from the clinician when inserted into a bladder and is the end of first inserted into the bladder. Sensor 16 has a tubular body 16 that includes tube wall, or over sheath 19. A string 18 is connected to proximal end 12 and configured to (1) be pulled to pull sensor 10 into an insertion tool, and (2) be pulled to pull sensor 10 out of a bladder. When sensor 10 is deployed in a bladder, string 18 preferably remains outside of the patient's body.

Sensor 10 also includes internal electronics 20 positioned on and attached to a flexible circuit board 21 and a spine 22 connected to the back of flexible circuit board 21 (i.e., the side of flexible circuit board 21 opposite electronics 20). Spine 22 is connected to flexible circuit board 21 preferably by welding. Spine (or shape memory spring) 22 is biased to a first, curved position and biases sensor to a first, curved position, as shown in FIGS. 1-3.

Figure 4:
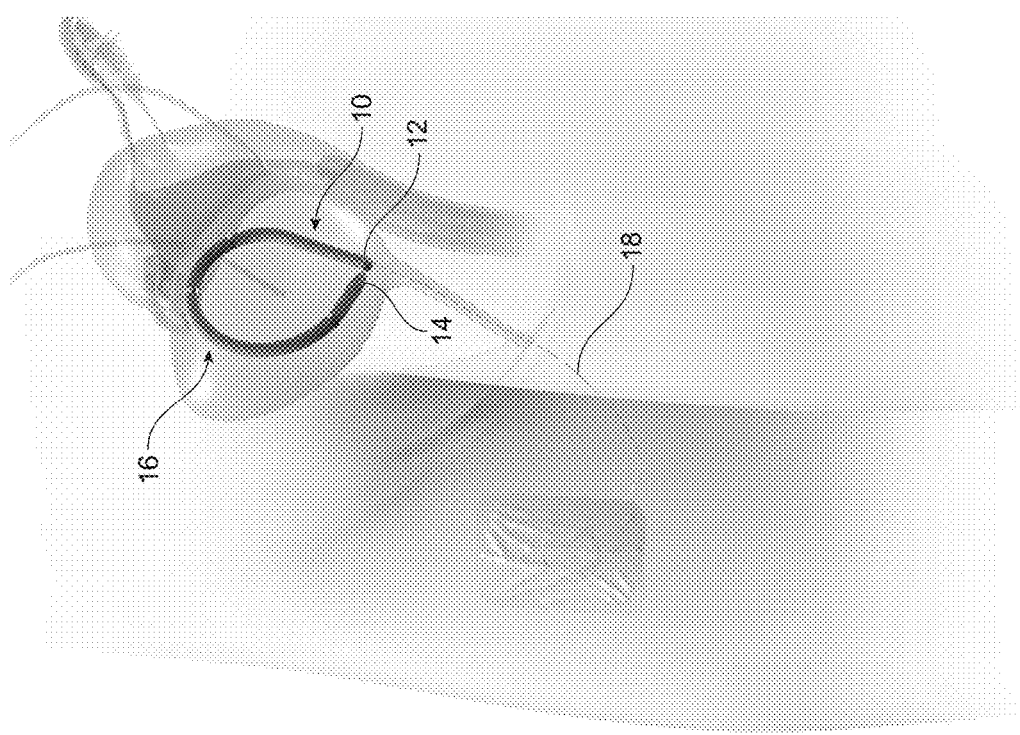
FIG. 4 is a partial side, perspective view of the sensor of FIG. 1 positioned in a human female bladder with the removal string secured to a patient's leg.
Figure 5:
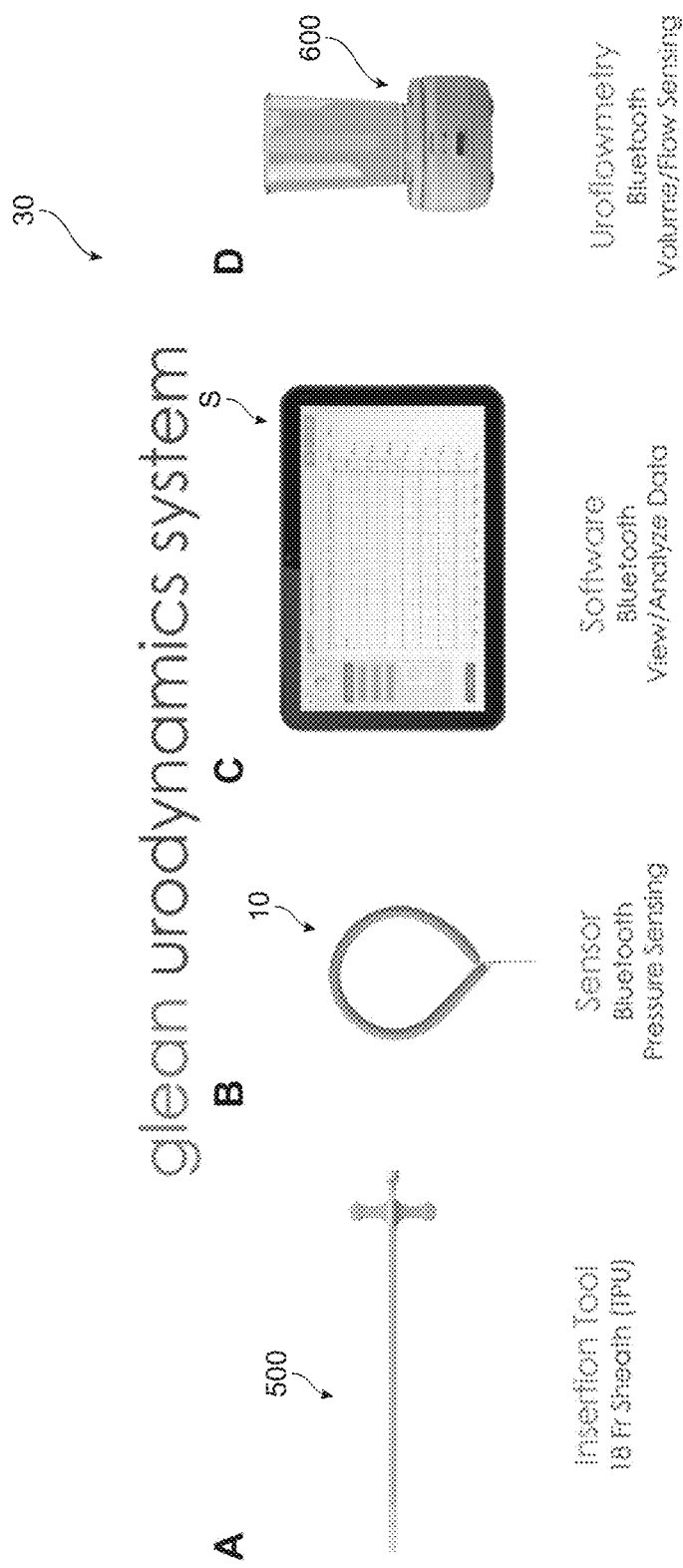
FIG. 5 illustrates a urodynamic sensor system and display according to this disclosure.

FIG. 4 shows sensor 10 in the bladder of a female human. FIG. 5 shows components a system 30 that comprises an insertion tool 500 (discussed herein) for inserting a sensor 10 into a bladder, a screen S to project data using a computer system 1000 (discussed herein) according to this disclosure, and a uroflow device 600 (discussed herein).

Figure 6:
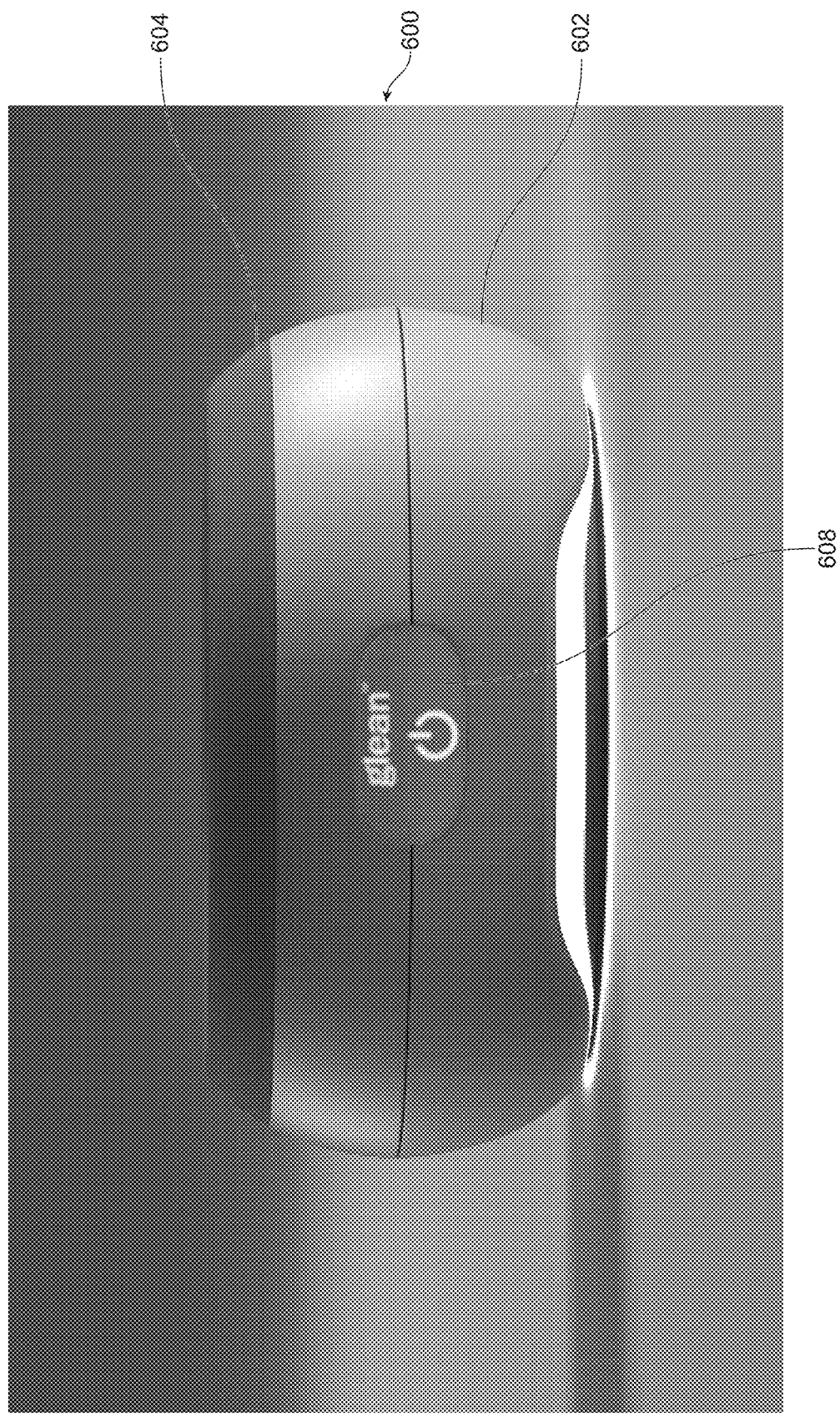
FIG. 6 is a front view of a uroflowmeter according to this disclosure.
Figure 7:
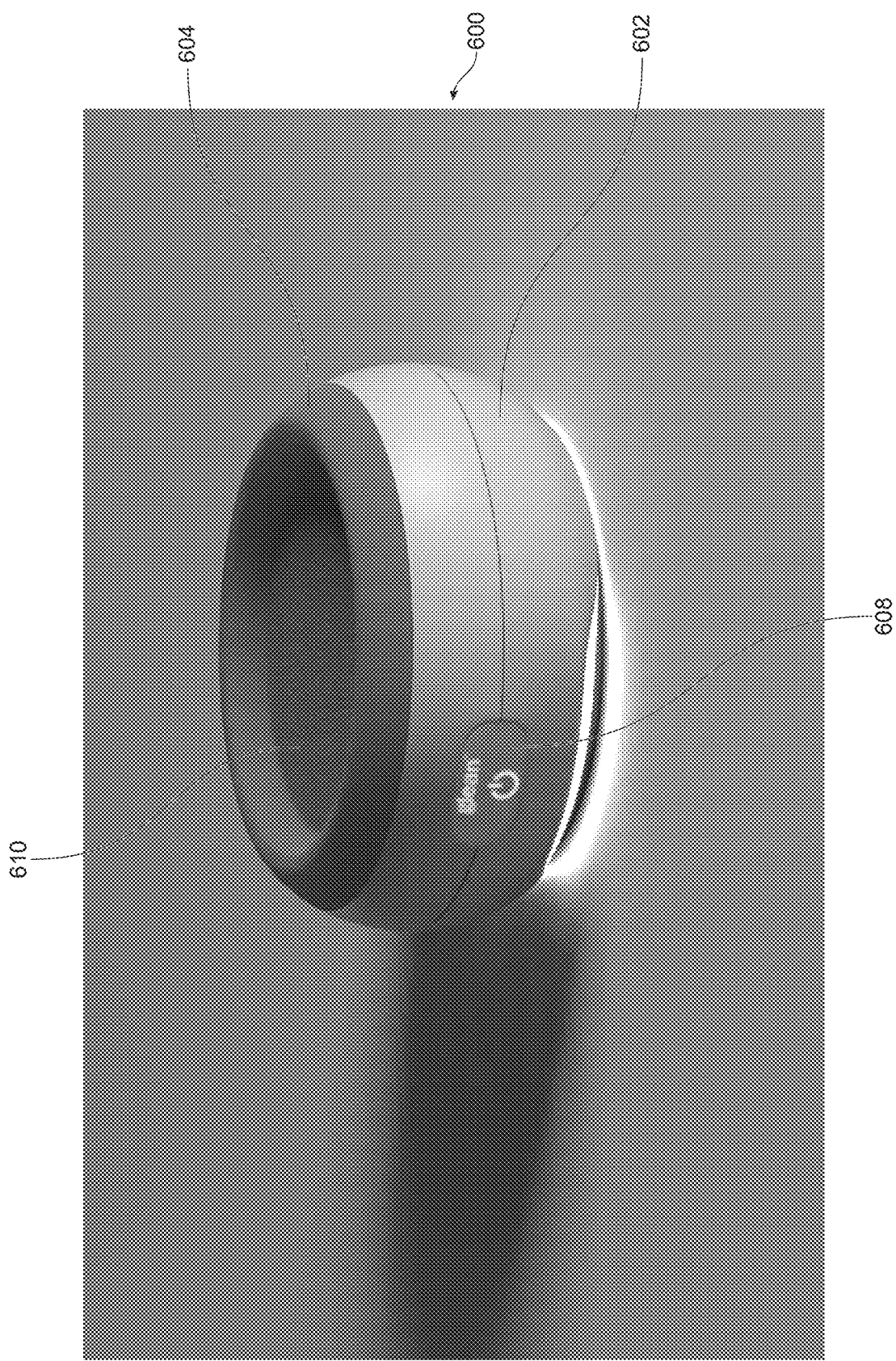
FIG. 7 is a top, perspective view of the uroflowmeter of FIG. 6.

FIGS. 6-7 show, respectively a side view and a top, perspective view of a uroflowmeter 600, which is a scale that has electronics configured to convert weight to volume.

Uroflowmeter 600 has a body 602, a top 604, and an off/on indicator 608. As best seen in FIG. 7, the top 604 has a depression 610 configured to hold a beaker or other container that holds urine. Uroflowmeter 600 weighs the urine, which assists clinicians in analyzing a urine void event.

Figure 8:
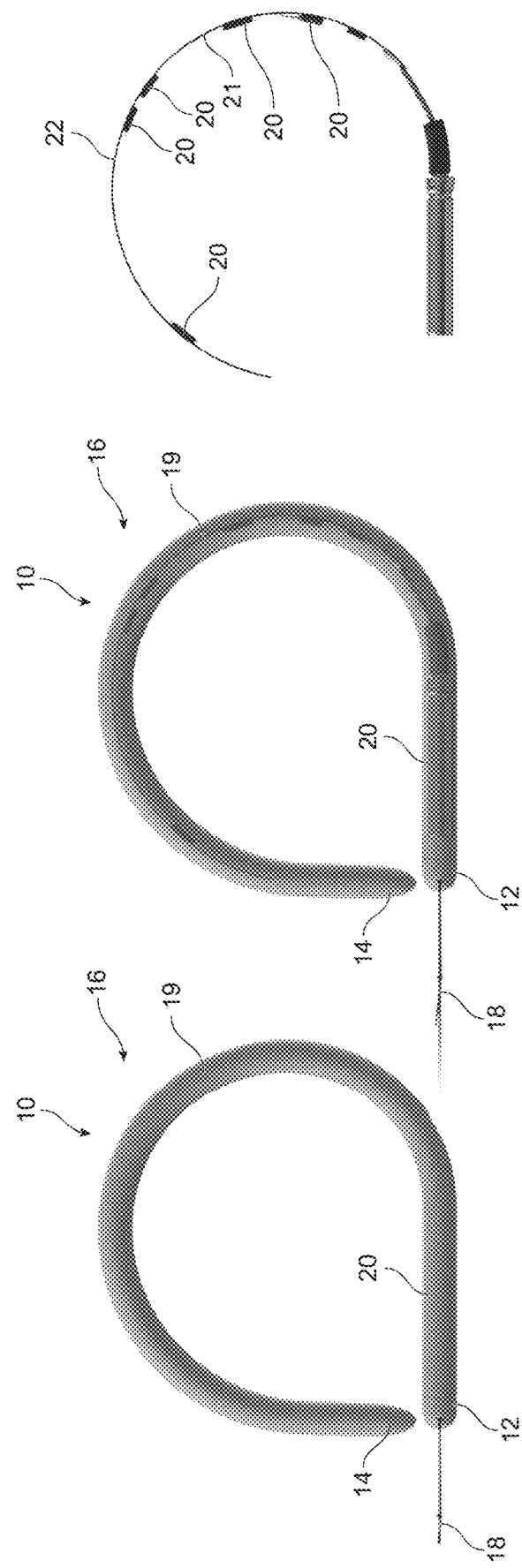
Figures 9, 9A, 9B:
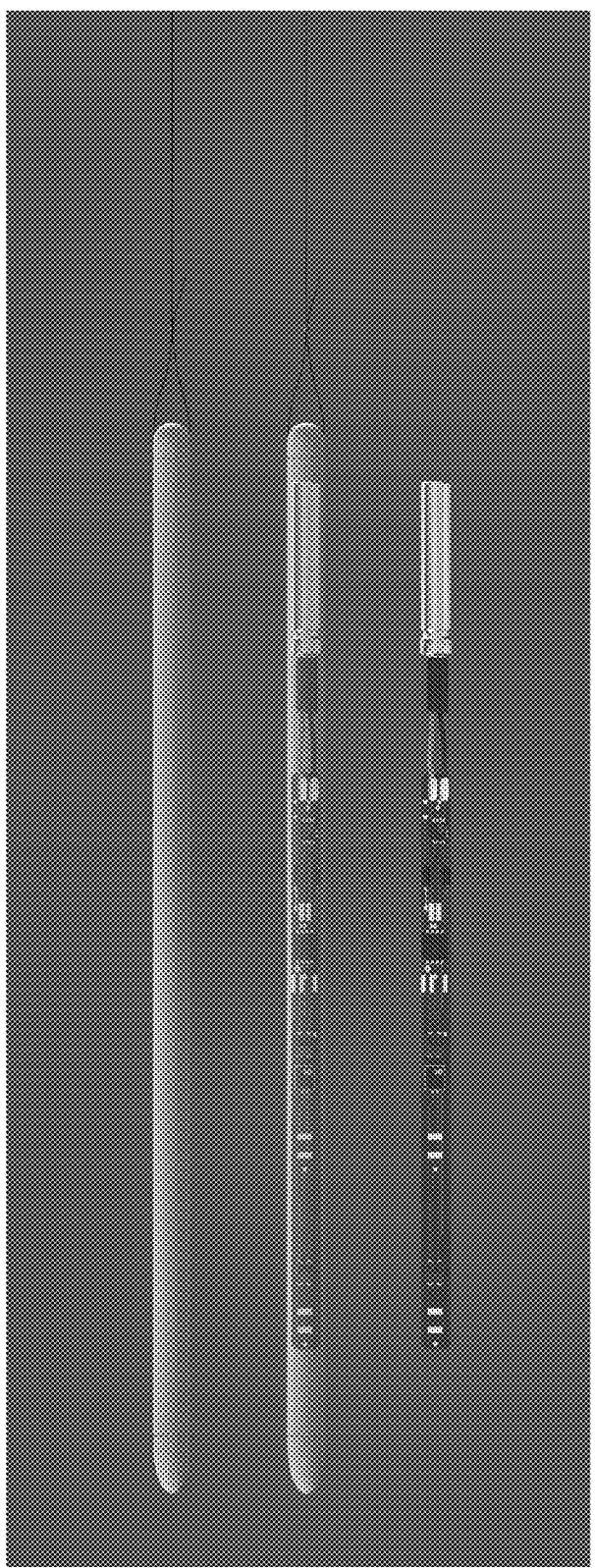
FIGS. 9-9B are top views of the sensors of FIGS. 1-3 in a straight position.

FIGS. 8, 8A, and 8B are side views, respectively, of the sensor of FIGS. 1, 2, and 3. FIGS. 9, 9A, and 9B are side views, respectively of the sensor of FIGS. 1, 2, and 3 moved to its second, straight position.

Figure 11:
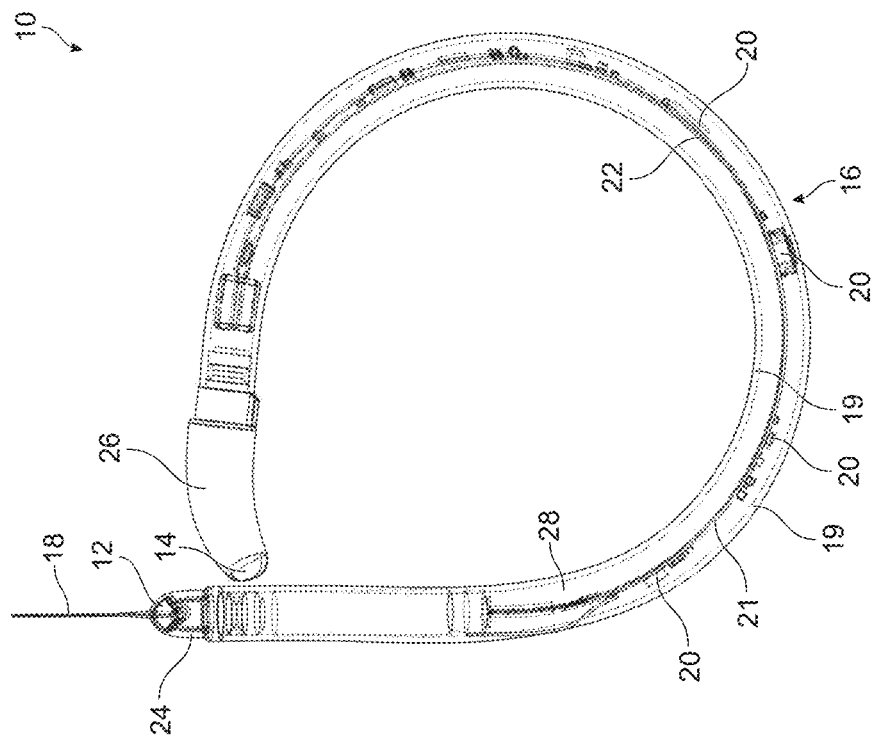
FIG. 11 shows the sensor of FIG. 10 with a clear outer wall so the internal components are visible.
Figure 10:
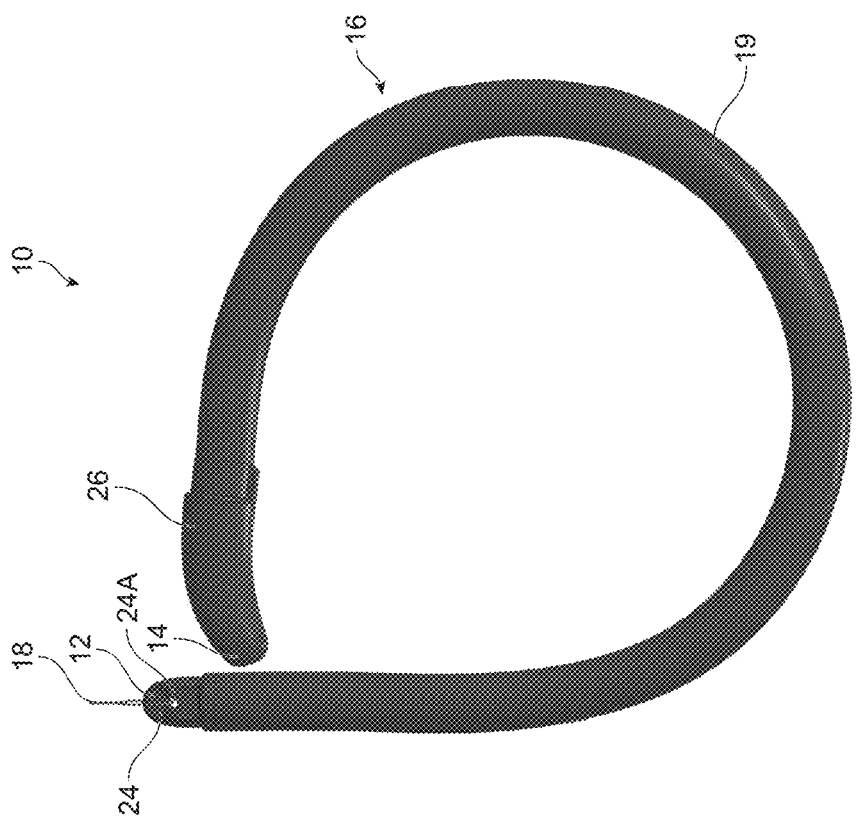
FIG. 10 is a top view of a sensor according to this disclosure with a removal string attached to its proximal end.

FIG. 10 is a top view of the sensor of FIGS. 1, 8, and 9 in its first, curved position. FIG. 11 is also a top view of the sensor of FIGS. 1, 8, and 9 in its first, curved position and depicting the outer sheath as clear so the internal electronics can be seen. In FIGS. 10 and 11 proximal end cap 24 and distal end cap 26 can more readily be seen. Proximal end cap 24 and distal end cap 24 are attached to tube, or outer sheath 19, such as by pressing them into cavity 28 with adhesive to secure them. Proximal end cap 24 has an aperture 24A for attaching to string 18. Distal end cap 26 preferably has a coude shape (e.g., curved) for easier insertion into a bladder.

A uroflowmeter 600 used to measure voided urine volume and changes to volume (flow).

Sensor 10

One embodiment of the sensor 10 may include:

A tubular outer housing (or "tube" or "outer housing" or "outer cover") preferably comprised of silicone elastomer or rubber, although any suitable material may be used, wherein the tube has a lumen (or "cavity") therethrough.

A flexible circuit board 21 with electronic components positioned inside of the tube.

A power source, such as a battery, positioned in the tube and preferably connected to the flexible circuit board.

One or more electronic parameter sensors, such as pressure and/or volume sensors, positioned in the tube and preferably on the circuit board, where they receive power from the power source.

In some embodiments, fluid, such as silicone oil, fills the cavity between the tubular outer housing and internal components. The fluid is preferably incompressible and electrically non-conductive.

A shape memory spring 22 that is positioned on the inside, part of, or outside of the tube and that is comprised of either steel, plastic, or other suitable material or some combination of materials. In one embodiment the shape memory spring 22 is welded to the bottom of the (i.e., the side that does not include circuitry) flexible circuit board 21. So, instead of, for example, using nitinol wire or injection molding to create a shape memory elastic housing, the flexible circuit board with the shape memory spring creates the specific shape for the sensor. In this case, the sensor has a generally circular or curved shape that prevents it from inadvertently being voided or discharged from the bladder. In some embodiments the spring 22 may be rectangular in cross-sectional profile to provide the appropriate profile for pushability and translation of force in a linear manner. This also provides additional support and rigidity for protection of the flexible electronic circuit board.

Endcaps 24, 26 for the tube are comprised of steel, plastic, silicone, or other suitable material. There is a distal end cap 26 and a proximal end cap 24.

A removal string 18 for pulling the sensor 10 and removing it from the bladder. The removal string may or may not be attached to an end cap and is preferably attached to the proximal end cap.

This sensor design enables reliable, low-cost manufacturing because the extruded sensor tubing is simple and inexpensive to make as compared to injection molding or nitinol hand assemblies. This sensor design also provides reliability and strength because the shape memory spring 22 is designed to provide sufficient torsional rigidity and hence increases the durability of the flexible circuit board (FCB) 21 and any electronic components attached to the FCB via soldering or other means.

The shape memory of the sensor 10 should preferably be sufficient to enable the sensor to be straightened for delivery through the urethra. Once delivered inside of the bladder, the sensor 10 springs back, or returns, to its original circular or curved shape. To achieve this a combination of manufacturing methods may be utilized including heat-treating, forming, and/or cold-rolling of the spring.

An additional benefit of the sensor 10 design is that the shape memory spring 22 may be flat and designed to mate with one or both endcaps and with the tube by creating the desired geometric configuration in each part. For example, the endcap mating could be used to provide additional stability and pushability in support of delivery. Side cutouts in the sensor housing would be used to provide reliable manufacturing and stability of the circuit as well.

This technique may be used with both endcaps whereby the spring is able to travel the entire length of the sensor housing, or from one endcap to a rigid or semi-rigid battery which is mechanically coupled to the battery. In this embodiment, the force may be transferred from one endcap to the battery to the spring to the other endcap.

In one embodiment, the shape memory spring 22 could translate force between each of the endcaps 24, 26 and act as a backbone or spine for the sensor 10. In another embodiment, the shape memory spring 22 could translate force from one endcap 24 or 26 to one or multiple components in the lumen of the tube. These embodiments are unique because they enable pushability and enable safe passage of the catheter through the urethra of the patient. Additionally, the rigidity of the spring 22 enables optimal mechanical properties that would otherwise be impossible to accomplish without drastically increasing the overall outer diameter of the sensor. By using the spring 22 the outer housing 16 of the sensor 10 can be reduced in overall outer diameter and also maintain flexibility. Ultimately, this design provides the optimal combination of soft material on the exterior coupled with mechanical strength for pushability which results in the best performance for any sensor insertion through the urethra of a patient.

The shape memory spring 22 could either be made using a manufacturing process to create a "flat spring," such as a leaf spring. Such a process could use either heat treating of the spring 22 to form, or use work hardening, each of which is known in the art. Work hardening of the shape memory spring is less likely to induce magnetic properties to the spring, and is most preferred in this disclosure.

In some embodiments, the shape memory spring (or simply "spring") 22 may be totally or partially coated with a material that prevents electrical contact with other components and prevents interaction with the circuit board. The coating material may also enable the shape memory spring to resist corrosion to increase the spring's reliability. This coating may be a material that is resistant to oils such as mineral oil. The coating may be applied using any suitable method, including spray or dip coating.

In another embodiment, shape memory may be obtained by using nitinol to provide the optimal mechanical properties for reliable configuration of the sensor.

Another option is to create the tube 16 using injection molding. To accomplish this, the mechanical properties and geometries of the materials used in the injection molding should be selected such that they can provide the proper amount of rigidity and flexibility while withstanding the tube's requirements for repeated actuation, i.e., repeated straightening and springing back to a circular or curved shape. This may be similar to a "living hinge" method of manufacturing. The endcaps 24, 26 could be made from either a metal, rigid plastic, semi-rigid plastic, elastomer, soft rubber, silicone, or any suitable material. The endcaps may also be comprised of some combination of these materials. The endcaps could be of various shapes as long as they support insertion of the sensor using the insertion tool as described herein.

In some embodiments, the spring may be covered using a sheet of adhesive. The adhesive sheet may be comprised of a non-conductive material to prevent electrical interaction with the circuit board. This adhesive sheet may be cut in any suitable manner, such as by using laser cutting or a punch method. This is beneficial because it is desirable to leave some portion of the flexible circuit board free from attachment to the spring to ensure reliability and protection of the circuit. If the circuit board is fully attached to the spring with adhesive when in a circular configuration, when the sensor is straightened the circuit board would be compressed, which would create interference with the adhesive. This could result in either delamination of the circuit from the spring 22, damage to the electrical components on the circuit board 21, or other undesirable reactions.

In addition to the coating, a double-sided adhesive sheet made of electrically non-conductive material may also prevent electrical interference between the spring and the FCB 21.

In some cases this may be manufactured in a method to streamline assembly including partial scoring which could enable select portions of the sheet to be prepared for adhesion while other parts remain non-adherent.

The adhesive may comprise materials that are resistant to solvents, oils, or other harmful fluids. For example, mineral or silicone oil may be used as lubrication because of its biocompatibility, but mineral oil and silicone oil can dissolve certain latex, plastics, and other rubber substances.

Attachment of the spring 22 to the flexible circuit 21 may also be accomplished using a mechanical process. In such an embodiment, the spring 22 may contain features designed to interact with the circuit board to provide a mechanical integration and enable reliable attachment with or without adhesive. This may improve flexibility of the sensor 10 and reduce bunching (or compressing) of the circuit board when attached to the spring and straightened. These mechanical features may be vias or other holes that are designed and created as part of the electronic circuit board and pegs that may be molded into the spring.

Insertion Tool

The insertion tool (or "tool" or "insertion device") 500, discussed in more detail below, delivers the sensor 10 to the bladder through the urethra and is generally comprised of the following components: an outer housing 504 with a handle 506; and a pushrod 530 with a handle.

The outer housing includes a channel or lumen through which the sensor can be delivered to the bladder. The outer housing also includes a tip 516, which could be of any suitable design including: a straight tip; a coude tip; a sheath tip; or a sheath tip with sensor endcap interaction.

In addition to the sensor endcap interaction at the distal end of the sheath, the proximal sensor endcap may be designed in a symmetric or asymmetric pattern to enable locking and translation of force rotationally through an interaction with a second lumen inside the sheath of the insertion tool. This would provide two methods of interaction to translate force rotationally and enable successful insertion of the sensor.

Both the straight and coude tip are similar to urological catheter tips, but include an angled tip with a key near the tip of the outer housing to enable the sensor to be delivered into the bladder. The angled tip design for the coude tip may offer greater advantage through column strength and mechanical rigidity or pushability when inserting into the urethra of a patient. This is because an angled tip that is on the top of the outer housing is directly on plane and may buckle from any force associated with the coude or straight tip during insertion. In this manner there could be advantages to the side port for certain patient anatomies such as a tight sphincter.

The sheath tip leverages the sensor endcap to perform the function of the tool tip. In this manner, the sensor endcap may also be designed as a straight or coude tip and constructed in a manner to simplify the insertion process. This could integrate two separate components designed to provide the optimal properties for insertion in the urethra such as pushability or navigation through challenging anatomies, such as bladder outlet obstruction and may be valuable for both female and male anatomies.

The sheath tip could also provide an added benefit because if the sensor is deployed before the tool is positioned properly in the bladder, then it would be unlikely to cause trauma to the tissue of the urethra. In this case, the sensor would essentially function as a urological catheter and be pushed through the urethra and into the bladder.

Regardless of the tip design, the material properties are selected to enable proper performance characteristics of the tool. This includes pushability, rigidity, trackability, and flexibility. The outer housing of the tool may be extruded from TPU, TPE, other similar materials, or any suitable material. To reinforce the pushability of the tube the tool may be reinforced with braided or coiled wire using stainless steel or similar materials.

The outer housing of the tool may also be marked with one or more markings to aid clinicians in understanding placement of the device using depth of the insertion. The markings could correspond to different sizes to incorporate either the anatomical requirements of that patient or using an average of multiple patients to determine the ideal depth of insertion for the device.

In some embodiments this may include a lower bound and upper bound based on the reported urethral lengths and statistical analysis from published literature. This would aid the clinician in understanding proper positioning of the sensor in the bladder.

The outer housing of the insertion tool may be optimized with the dimensions and mechanical properties of the sensor housing and pushrod to obtain optimal device performance.

This allows for simple and easy insertion while reducing the outer diameter of the outer housing. This could also enable the outer housing to be extruded and maintain kinkability and pushability with very small tubing dimensions. This greatly reduces cost and complexity for the device because extrusion is much cheaper than braided or coiled tubing and requires less money and time to manufacture.

In some embodiments the sheath may be designed with a total length and flexibility such that the tool may be inserted completely until the handle of the tool reaches the urethral opening. With the optimal flexibility the sheath and sensor are unlikely to injure the patient's bladder. This is optimal to simplify the training for the clinician and ensure they are in the bladder when the sensor is deployed.

In some embodiments, the pushrod may be injection molded from a semi-rigid plastic or elastomer. This could also be molded in an asymmetric or non-uniform shape to obtain the optimal mechanical properties of the device.

Deployment of the Sensor

To prepare the tool and sensor for insertion, the sensor is inserted into a first lumen of the outer housing (or "over sheath") of the tool. In some embodiments, the removal string may be pre-positioned such that the clinician only needs to lubricate the sensor and pull the string until it locks in the insertion tool.

Once the sensor is in place, the sheath and sensor are prepared for insertion into the urethra of the patient. The sheath and sensor will be inserted until the sensor tip reaches the bladder. The clinician will then use the pushrod to deploy the sensor into the bladder. In some embodiments urine may flow around the pushrod and out of the sheath. The pushrod may also contain a lumen to enable flow of urine through the pushrod. This is particularly helpful for the clinician to confirm proper placement of the sensor in the bladder.

Depth markings or length measurements may be (such as by being pad printed) on the outer housing tubing to help clinicians confirm proper placement of the sensor in the bladder.

In another embodiment, the outer housing may incorporate a second lumen configured for urine to flow therethrough once a certain portion of the tool has reached the bladder. This could aid in proper placement of the sensor because a user would know the tool is in proper position for insertion into the bladder. The second lumen could also be temporarily filled by a wire or other structure to ensure reliable flow of urine by preventing lubricant from clogging the second lumen. The wire or other structure would be removed when the user felt the tool was in the bladder to permit the passage of urine through the second lumen.

One embodiment of the insertion tool may be designed in a manner to further improve the pushability of the sensor and insertion tool. This embodiment is similar to the sheath design but by using an expanded sensor endcap that overlaps the sheath inner diameter (ID) the design transfers force directly from the sheath to the endcap, whereas the sensor in the sheath design previously described has no such ability and relies on the transfer of force from the pushrod to the sensor. In this embodiment, it may be possible to decrease the outer diameter (OD) of the sheath by leveraging this interaction between the sensor endcap and the sheath of the insertion tool.

In another embodiment of the over sheath with endcap interaction, the endcap may be designed in a manner to provide accurate rotational positioning of the sensor endcap and the sheath. One manner to accomplish this is to provide one or more keys and keyways in the end of the sheath and one or more corresponding, mating features on the sensor endcap that would enable precise rotational positioning of the sensor and the tool. This would enable the translation of rotational force between the handle of the insertion tool sheath to the sensor endcap. This could be valuable because in some instances, the patient anatomy may be challenging for insertion and require a coude or rounded tip. This version of our device would allow clinicians to control the rotational orientation of the sensor endcap (i.e., the tip) as it advances through the urethra.

The rotational positioning may be indicated to the clinician through one or more markings, such as one or more features molded into the handle of the sheath or lines or other markings on the insertion tool sheath, which can be added in any suitable manner, such as by co-extrusion or pad printing.

This embodiment would also enable the sensor to be loaded into the insertion tool by the string pulling it through instead of the sensor being pushed into the sheath by the pushrod. The string may also be secured to the proximal end of the pushrod to prevent any movement or premature deployment of the sensor.

Sensor and Insertion Tool Example 2

Sensor Endcap (or Tip) Integration with the Insertion Tool

The sensor and insertion tool of this Example 2 is the same as the sensor and insertion tool of Example 1 except as noted herein. Sensor distal tip (or insert, or end cap) integration with the insertion tool sheath allows for rotational orientation of the sensor using the handle or sheath of the insertion tool by gripping and rotating the insertion tool handle, which in turn rotates the sensor including its distal tip. In this manner a user can rotate the sensor by the same amount as the insertion tool is rotated and locate the distal tip of the sensor at the proper position for insertion into the bladder. Then the sensor is pushed, using a push rod out of the insertion tool and into the bladder without (or with minimal) trauma to the patient.

Figure 12:
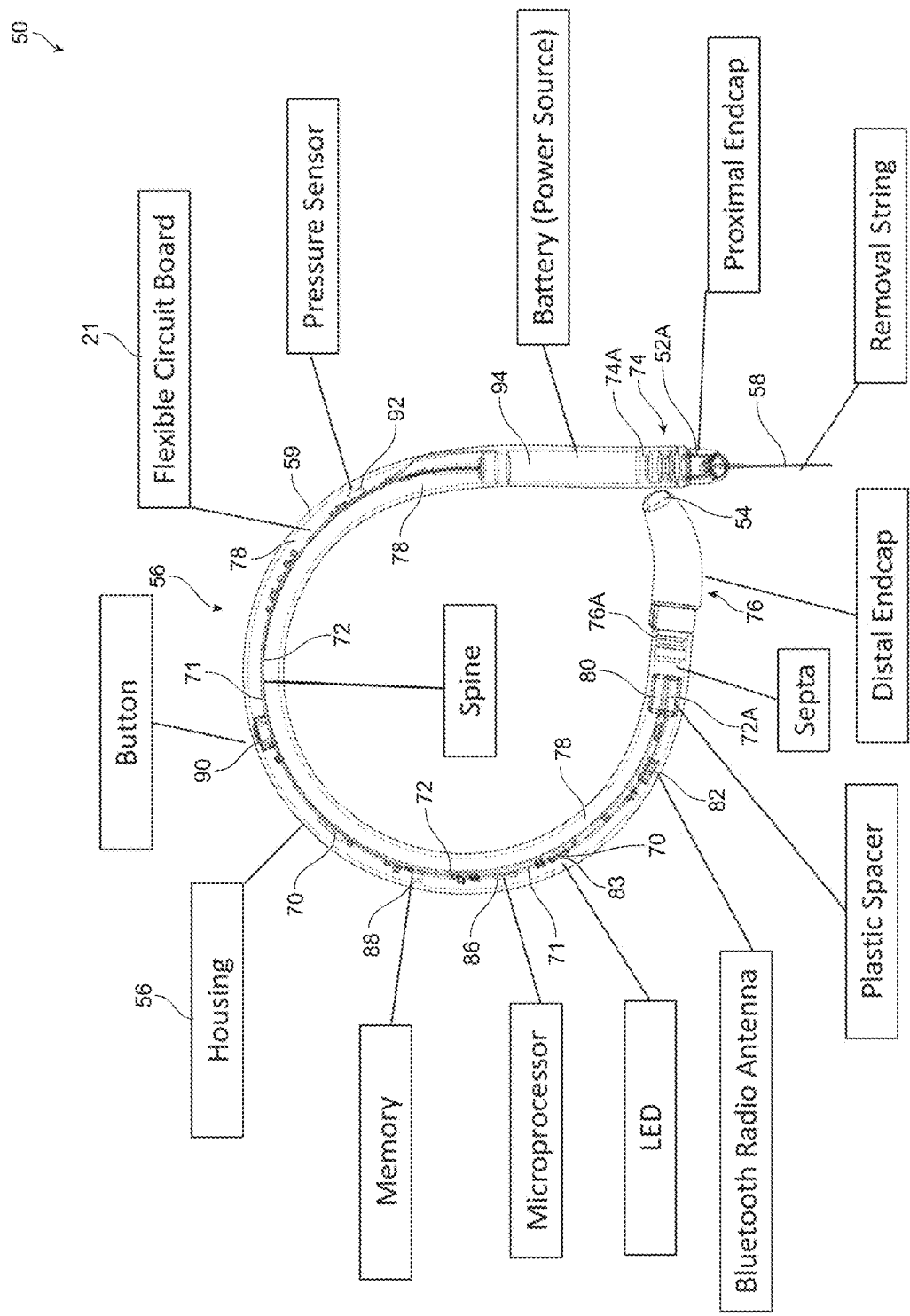
FIG. 12 shows a side view of an alternate sensor with various components labeled.

FIG. 12 shows an alternate embodiment of a sensor 50 according to this disclosure. Sensor 50 has a proximal end 52, a distal end 54, a body 56 with an outer wall (or tube or outer sheath) 59 that is comprised of silicone rubber (or elastomer). Proximal end cap 74 has an aperture 52A that attaches to removal string 58. Removal string 58 is used in the same manner as previously described string 18. Proximal end cap 74 and distal end cap 76 are attached to tube 56 in the same manner as previously described end caps 24, 26 and tube 16. As shown, proximal end cap 74 has a narrow section 74A that fits in the cavity 78 of tube 56 and distal end cap 76 has a narrow section 76A that fits inside the cavity 78 of tube 56.

A flexible circuit 71 retains electronics 70 and a spine 72 is attached to flexible circuit board 71 on the side opposite electronics 70, preferably by welding spine 72 to flexible circuit board 71. Spine 72 is biased to a first, curved position, which biases sensor 50 to its first, curved position.

A spacer 80 is preferably comprised of plastic or other soft material and covers end 72A of spine 72. This protects the inner wall of tube 56 from being torn by end 72A.

The electronics on this version of sensor 50 include a Bluetooth radio antenna 82, and LED 83, a microprocessor 86, a memory 88, a button 90 configured to turn sensor 50 off and on, and a pressure sensor 92, which measures the pressure of urine in the bladder when sensor 50 is positioned in a bladder. A power source 94, such as a buttery, is positioned in tube (or housing) 56 and supplies power to the electronic components 70 through flexible circuit board 71.

Figures 13, 14:
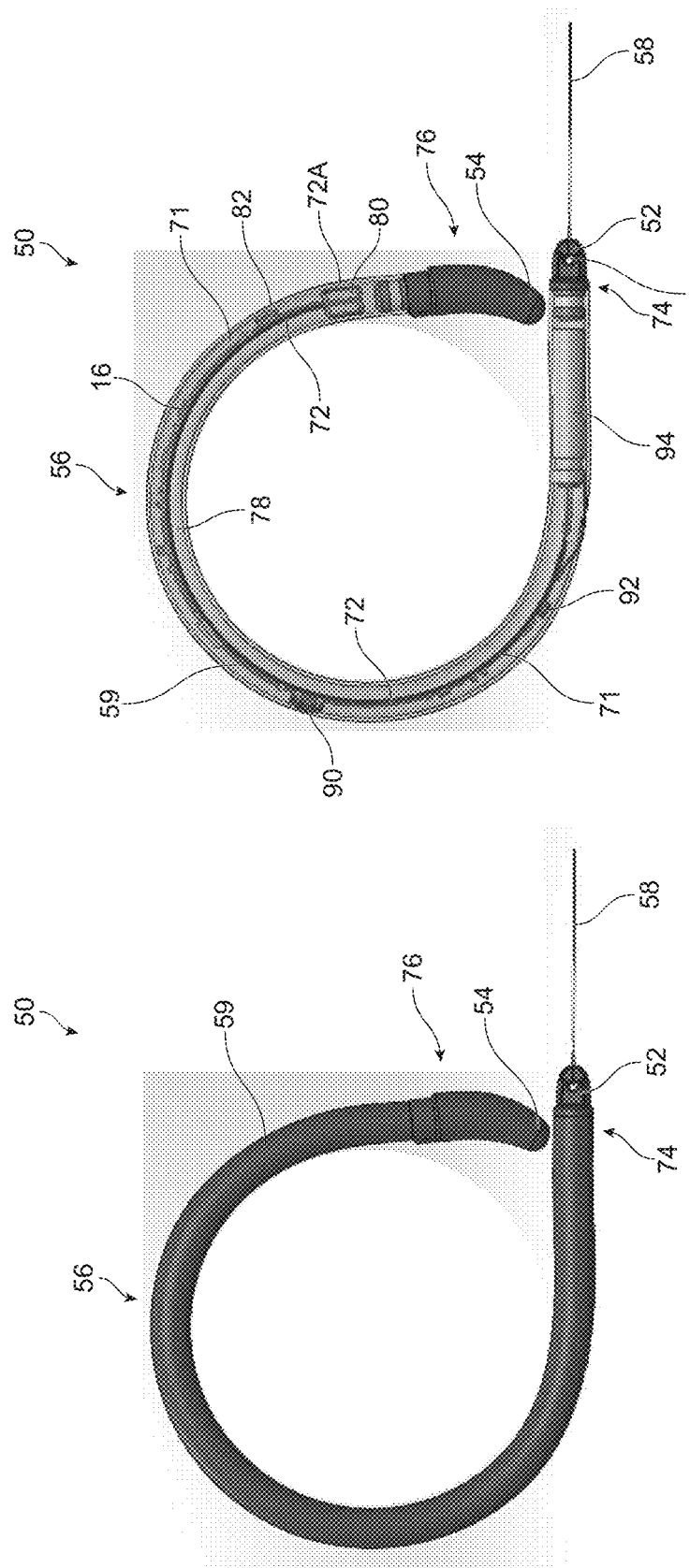
FIGS. 13-14 are alternate, top views of the sensor of FIG. 12.
Figure 17:
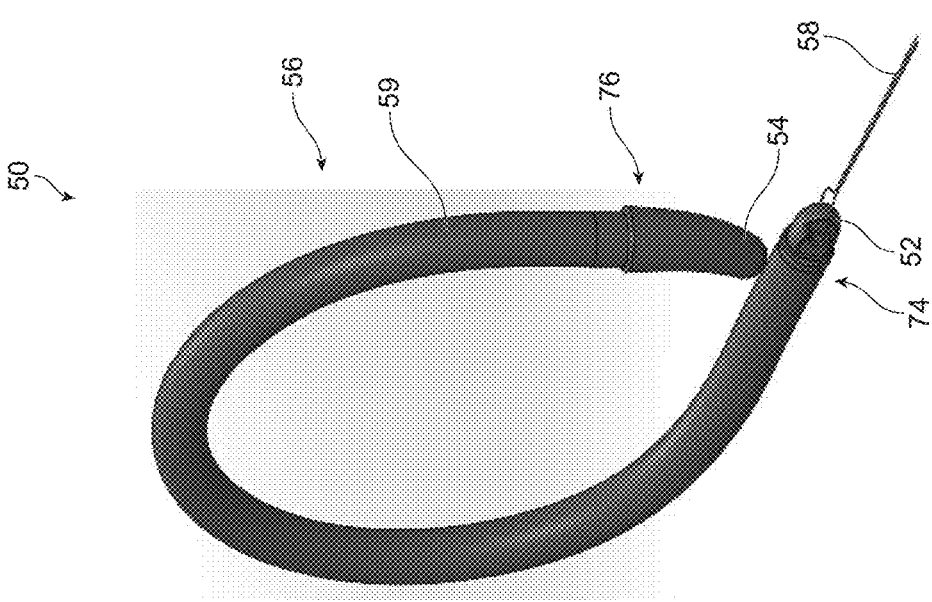
FIGS. 15-17 are side, isometric views of the sensor of FIGS. 12-14.
Figure 16:
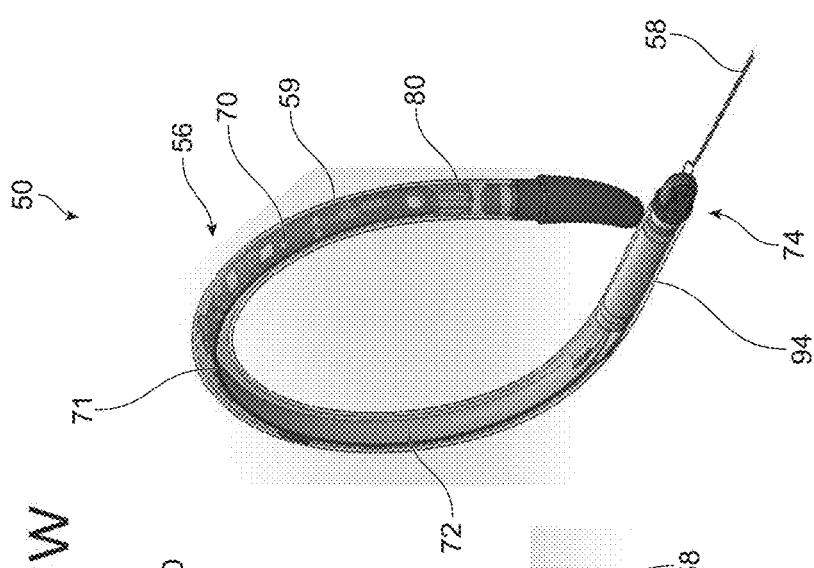
Figure 15:
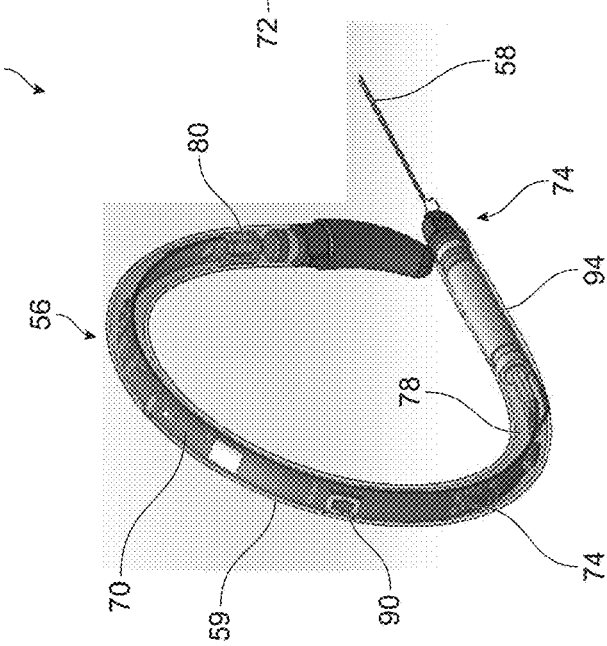

FIGS. 13 and 14 are top views of sensor 50. FIGS. 15-17 are isometric views of sensor 50 with FIGS. 15-16 showing the tube as clear so the internal components of sensor 50 can be better seen.

FIGS. 18-22 show close-up views of some internal components of sensor 50 with tube 56 being shown as clear.

Figures 23, 24:
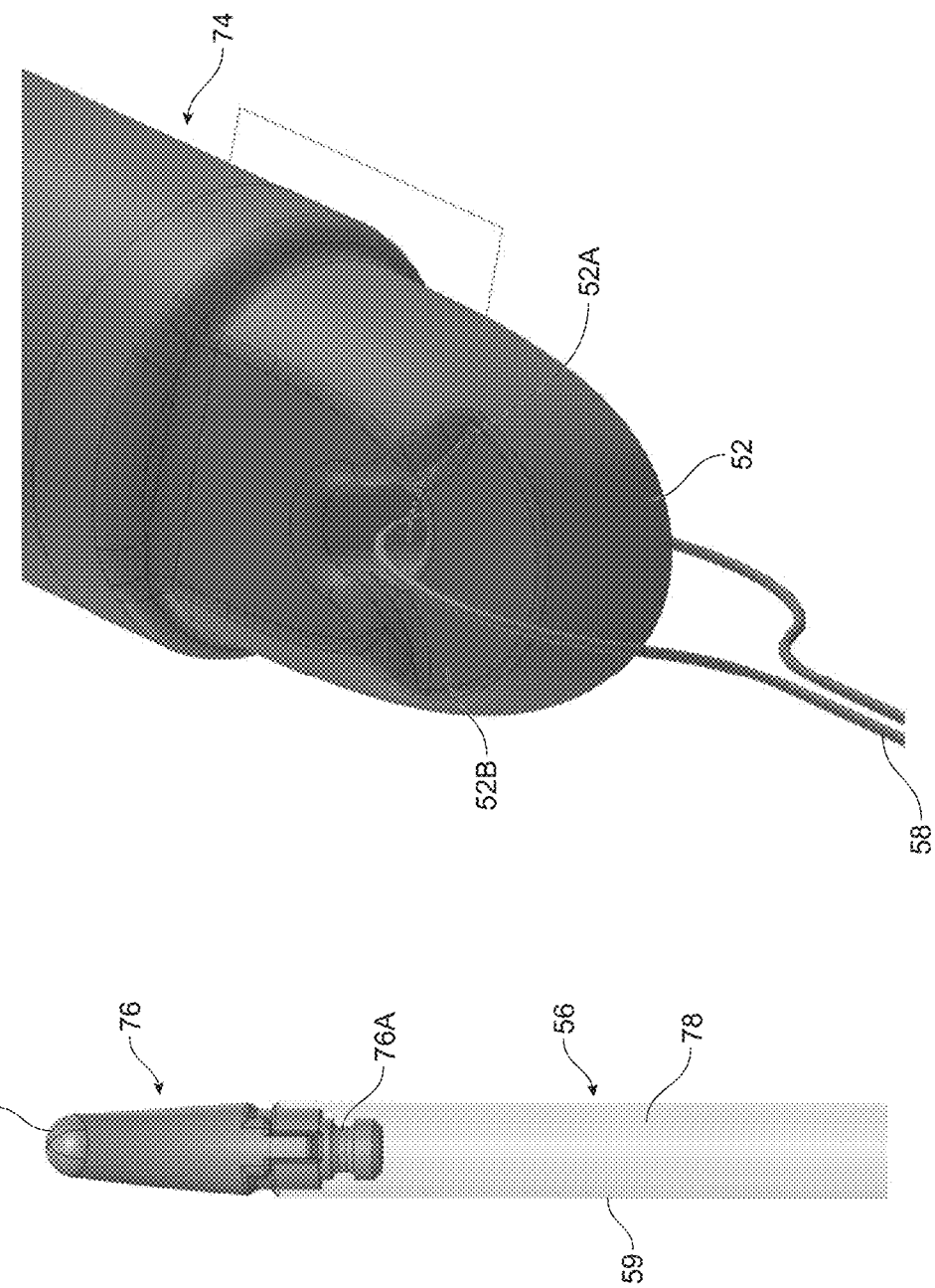
FIG. 23 is a partial, top view of the distal end of the sensor of FIG. 21 showing the distal tip.
FIG. 24 is a close-up, partial view of the proximal tip of the sensor of FIG. 21 with the removal string attached.

FIG. 23 shows a front view of a distal end cap of sensor 50 with the curve, or coude tip, facing forwards with narrow portion 76A inside of cavity 78 of tube 56. FIG. 24 is a close-up view of proximal end cap 74. Opening 52A, which connects to removal string 58 can be seen as can dual-flat connective portion 52B. Dual-flat connective portion 52B is on each side of proximal end cap 74 and is configured so a clinician can grasp proximal end cap 74 with a tool, such as forceps, and pull it out of a bladder.

Figure 26:
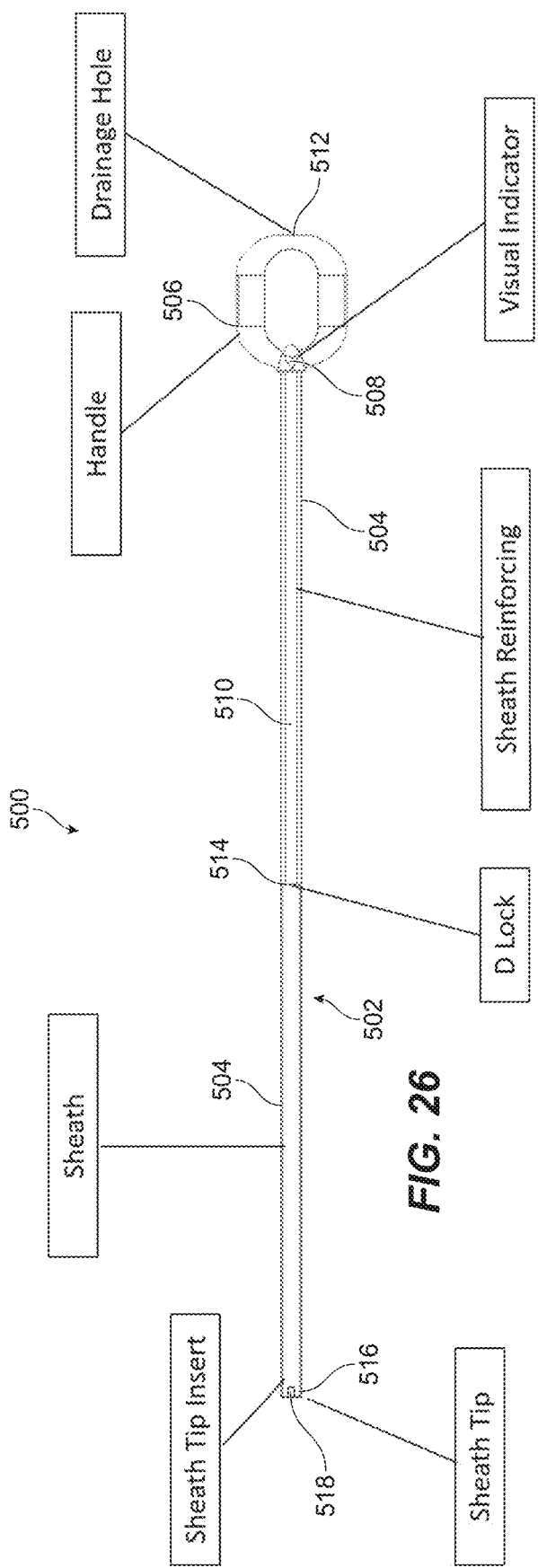
FIG. 26 is a side view of a push rod with various components labeled.
Figure 25:
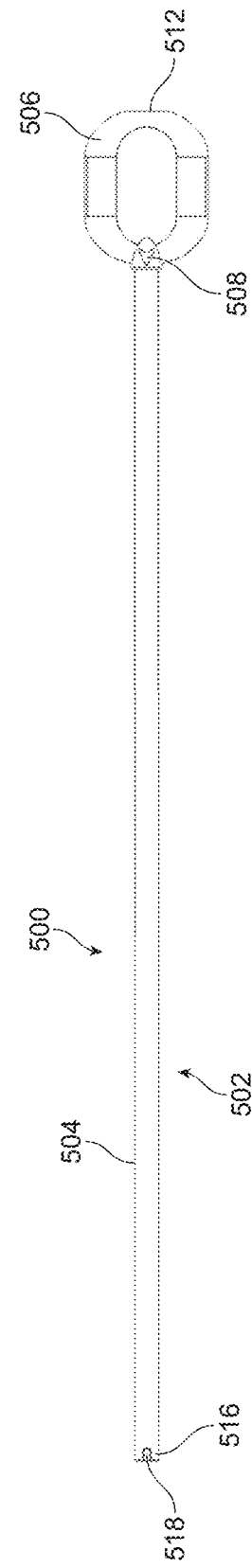
FIG. 25 is a side view of an insertion sheath and handle used to implant a sensor of this disclosure into a bladder.

FIGS. 25 and 26 show an insertion tool 500 according to this disclosure. Insertion tool 500 has an elongated body or sheath 502 with an outer wall 504, a sheath reinforcement 504 at its proximal portion, which is the portion of sheath 502 nearest the handle 506. A visual indication 508 that enables a clinician to see inside of lumen 510, a drainage hole 512 through with a push rod will pass and permits drainage of urine from the bladder through drainage hole 512 when a sensor, such as sensor 50, is properly positioned in a bladder.

AD-lock 514 is a structure of, or in, lumen 510 that mates with or otherwise connects to the proximal end cap, such as proximal end cap 74, to prevent sensor 50 from advancing any farther into lumen 510 and to engage proximal end cap 74 in order to translate rotational force to sensor 50 when handle 506 and insertion tool 500 are rotated. Insertion tool 500 further has a distal end (or sheath tip) 516 having a sheath tip insert 518. Sheath tip insert 518 is where a sensor, such as sensor 50, is inserted into sheath 500 prior to insertion into a bladder. When sensor 50 is inserted its proximal end cap 74 is blocked from advancing by D-lock 514. Distal end cap 76 has a protruding structure, such as a key or other projection, that is received in sheath key insert 518, which as shown is a slot or keyway. Distal end cap 76 extends outward from sheath tip 516 and rotational force is transmitted to it by sheath tip insert 518 when handle 506 and insertion tool 500 are rotated. In this manner, a clinician can rotate the distal end cap 76 until it is aligned with the bladder opening.

Figure 27:
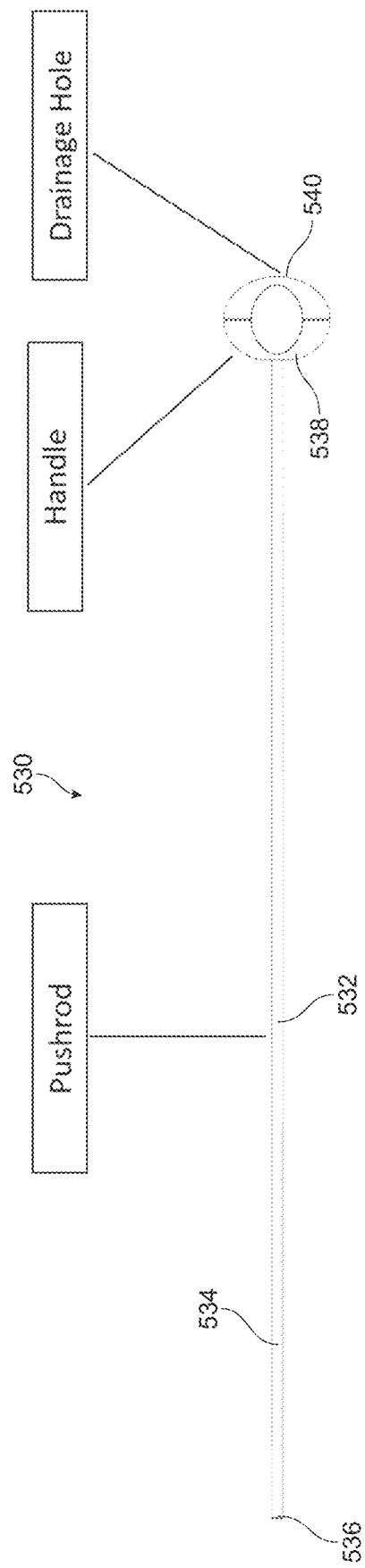
FIG. 27 is a side view of the handle with push rod to be used with the sheath of FIGS. 25-26.

FIG. 27 shows a push rod 530 that is used with insertion tool 500. Push rod 530 pushes a sensor, such as sensor 50, out of lumen 510 and into a bladder. Push rod 530 has a stem 532 with a tip 536 and preferably a lumen 534 through which urine can pass. Stem 532 is connected to a handle 538 that preferably has a drainage hole 540.

When a sensor, such as sensor 50, is in insertion tool 500 and properly positioned to be deployed, tip 536 and stem 532 of push rod 530 are pushed by a clinician through drainage hole 532 and into lumen 510 of insertion tool 500. This pushes sensor 50 out of lumen 510 and into the bladder. Urine moving through lumen 534 (if utilized) indicates that sensor 50 is fully positioned in a bladder.

FIG. 30 is a close-up view showing the lumen 510 and D-lock 514. As shown, lumen 510 has a large-diameter section 510A and a narrower-diameter section 510B through which the proximal end cap 74 of sensor 50 cannot pass. FIG. 28 is a close-up view showing sheath tip insert 518.

FIG. 29 is an end view of handle 506 in which drainage hole 512 and visual indicator 508 are visible. As can be seen, portion 510B of lumen 510 has a curved top, curved bottom, and flat sides.

FIG. 31 shows a side view of sensor 50 in its straight position when moved into insertion tool 500. FIG. 32 is a close up view of sheath tip 516 of insertion device 500 showing sheath tip insert 518. FIG. 33 is a close-up view showing the proximal end cap 74 and retrieval string 58 of sensor 50 positioned in the sheath of insertion tool 500.

FIG. 35 is a test protocol on identified sensors 1, 2, and 3. FIG. 36 shows a test protocol used on identified sensors 1, 2, and 3. FIG. 37 shows a test protocol on identified sensors 1 and 3 FIG. 38 shows a test protocol run on identified sensors 4, 5, and 6.

FIG. 39 shows a test protocol run on identified sensors 4 and 6. FIG. 40 shows a test protocol run on a sensor designated as sensor 8. FIG. 41 shows a test protocol run on a sensor identified as sensor 10. FIG. 42 shows a test protocol run on a sensor identified as sensor 12.

Figures 44, 44A, 44B:
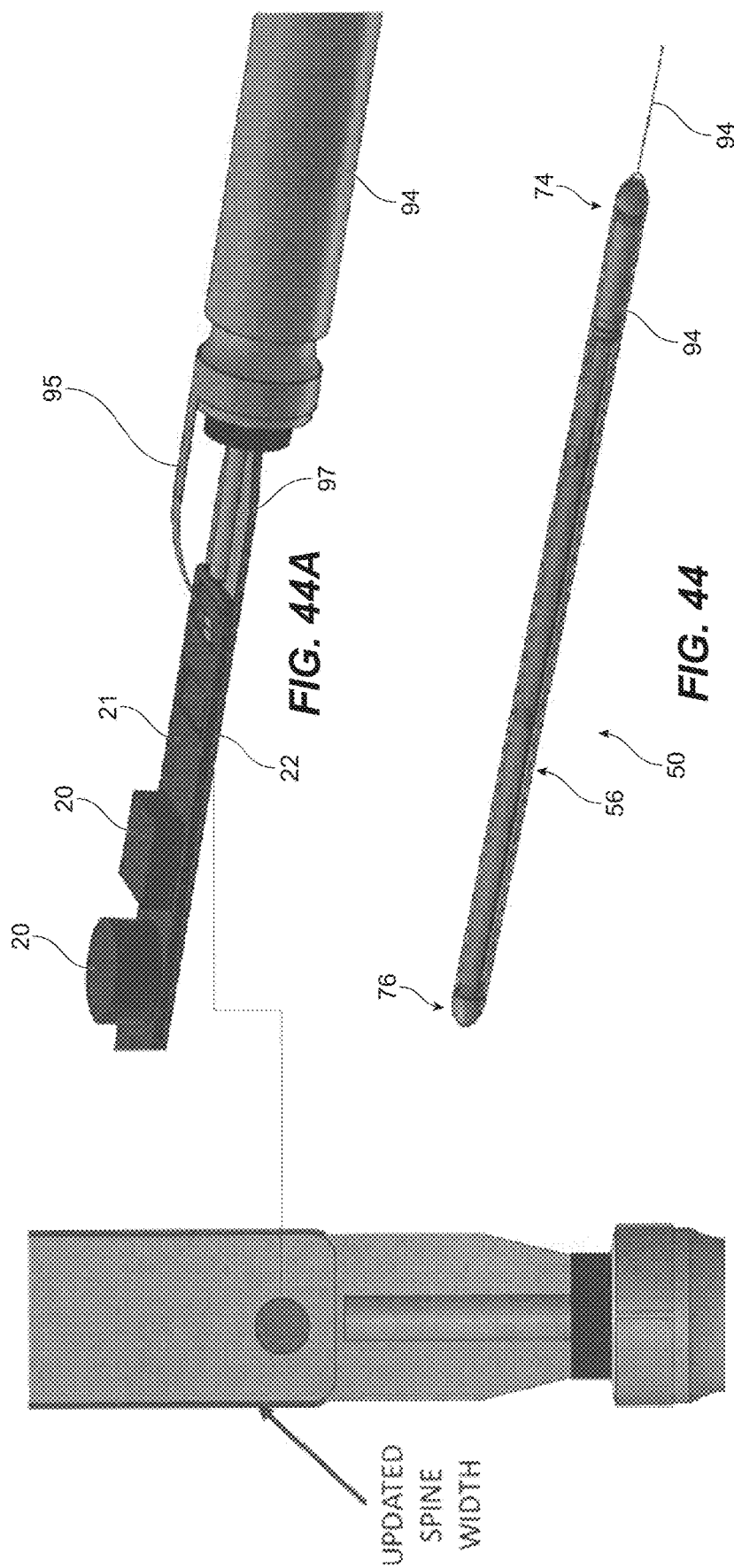
FIGS. 44-44B show internal components of a sensor according to this disclosure.

FIGS. 44-44B show a sensor 50 and a battery 94 with its positive and negative connections, 95 and 97, respectively.

Figure 49:
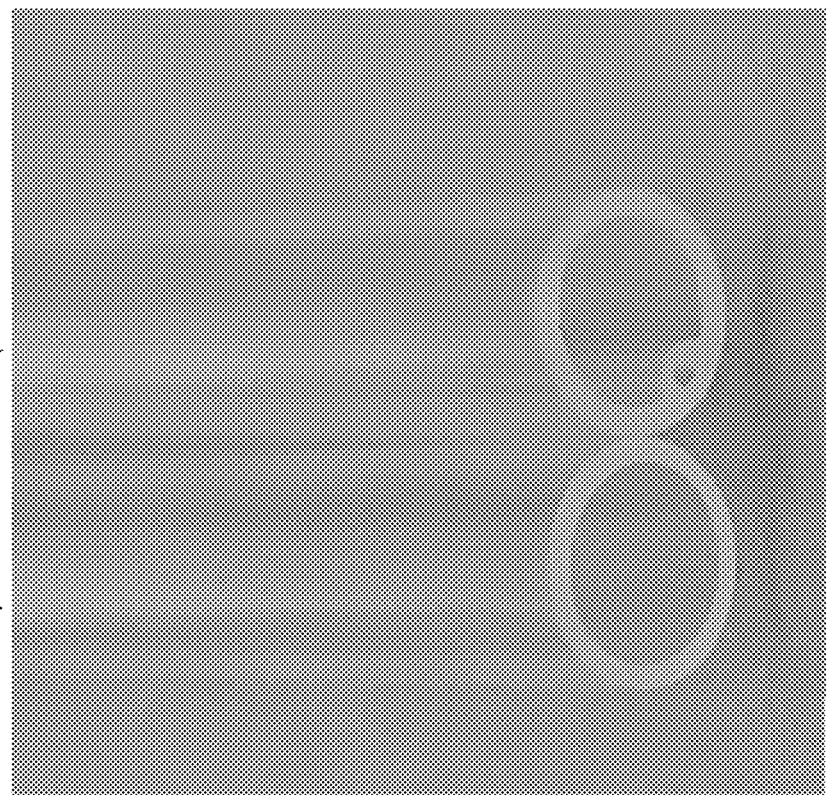
FIG. 49 shows silicone rubber extrusions that can be used to make the outer sheath (or "outer wall," "outer housing," "tube," or "outer tube") of a sensor according to this disclosure.
Figure 59:
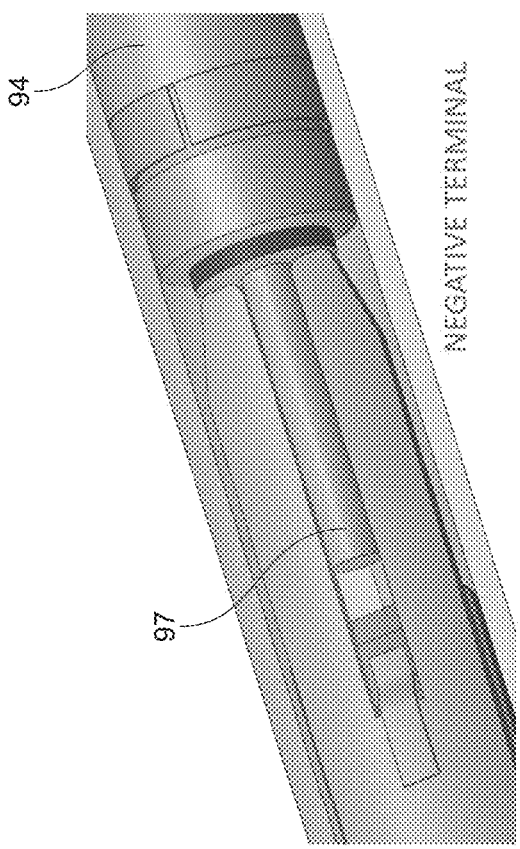
FIGS. 57-59 show cut-away images of a sensor positive electrical contact and negative electrical contact structure to provide power to the internal sensor components.
Figure 58:
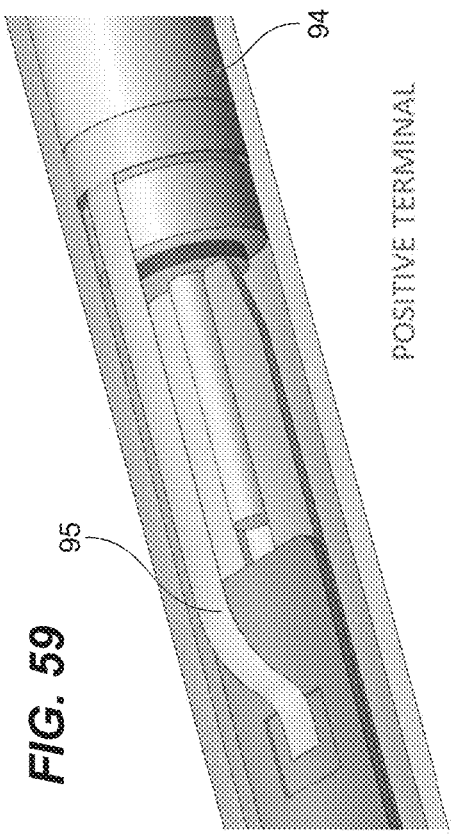
Figure 57:
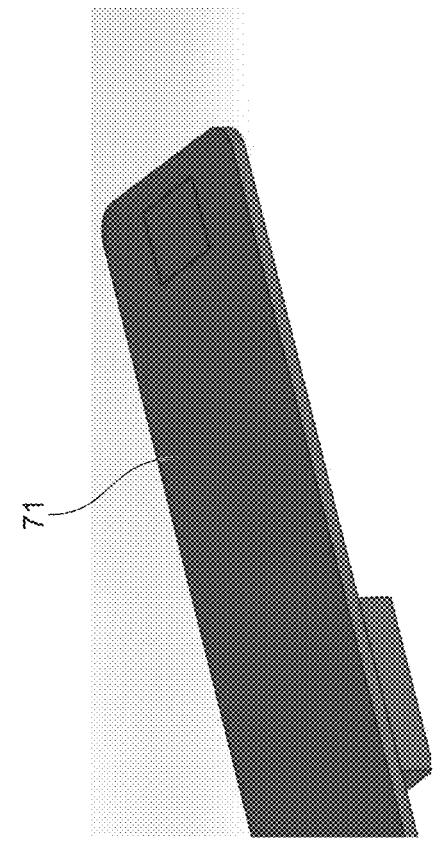
Figure 65:
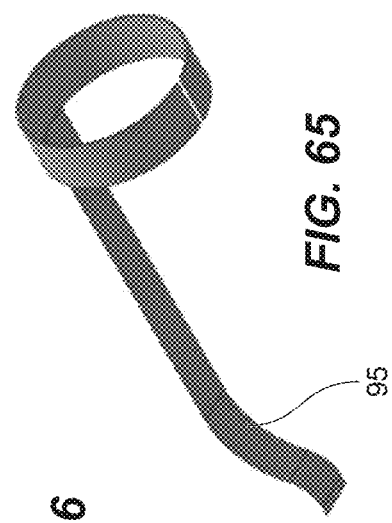
FIGS. 65-68 show various views of a battery connector for a sensor according to this disclosure.
Figure 66:
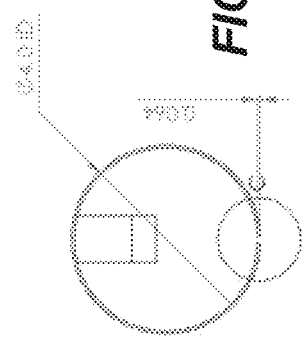
Figure 67:
Figure 68:
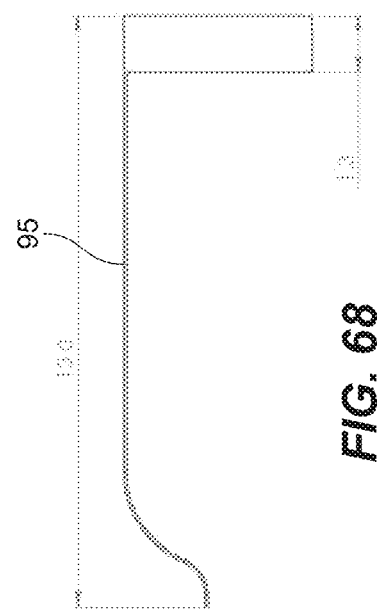

FIGS. 45-48 are views of a sensor 50. FIG. 49 shows silicone rubber extrusions that can be used as the outer sheath for sensor 50. FIGS. 50-51B show prototypes of sensors according to this disclosure showing the spine 72, flexible circuit board 71, and electronics 70 positioned in a tube 56. FIGS. 52-53 show a spine 72. FIG. 57 is a partial image of a spine 71. FIG. 58 shows a positive terminal 95 of battery 94. FIG. 59 shows a negative terminal 97 of battery 94.

FIGS. 60-64 show a possible assembly process of a sensor 50. At FIG. 64 the electronics 70 are connected to the flexible circuit board 71. At FIG. 63 the spine 72 is connected, such as by welding, to flexible circuit board 71. At FIG. 62, battery 94 and positive lead 95 and negative lead 97 are connected. At FIG. 61, the assembled flexible circuit board and spine are inserted into outer sheath 56. At FIG. 60, end caps 74 and 76 are attached and cavity 78 is filled with silicone oil to a pressure greater than atmospheric.

Figure 70:
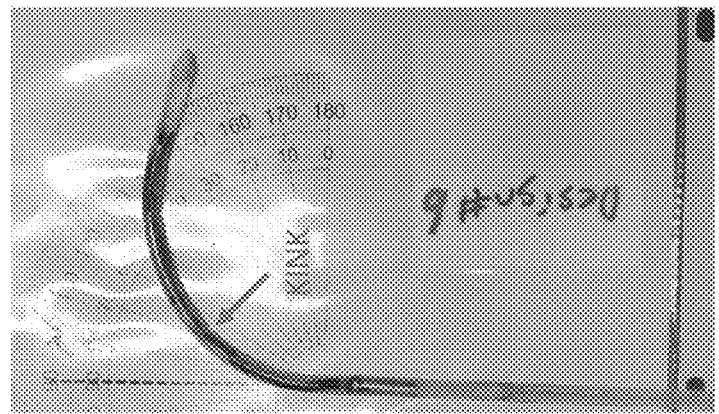
FIGS. 70-72 illustrates the flexibility of different sensor designs.
Figure 71:
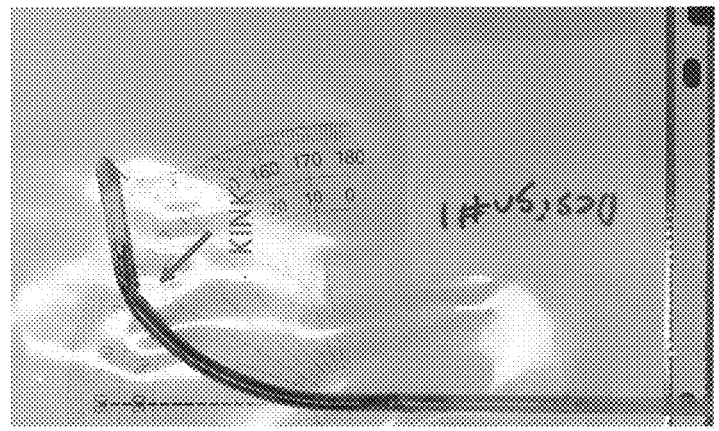
Figure 72:
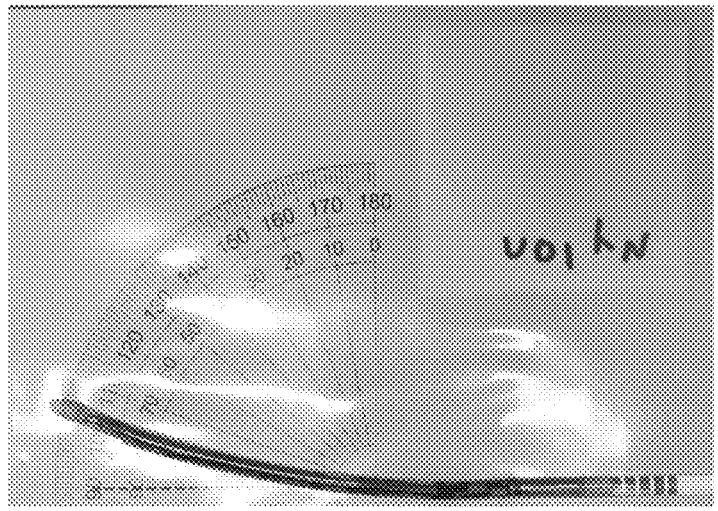
Figure 74:
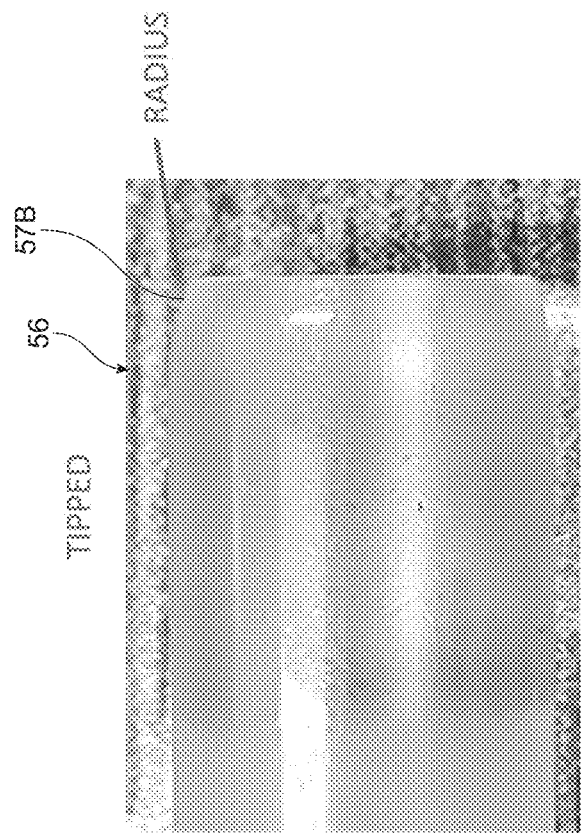
FIGS. 73-74 show partial, side views of a sensor tube with an end that is not tipped versus one that has a radiused tip for eliminating trauma.
Figure 73:
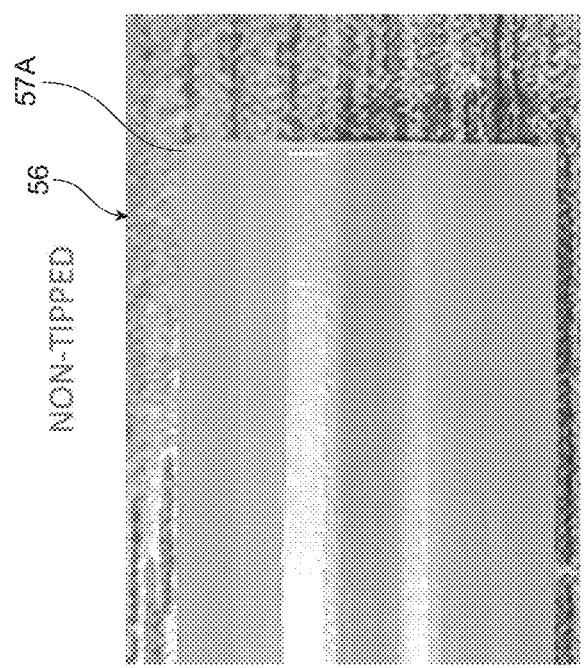
Figure 78:
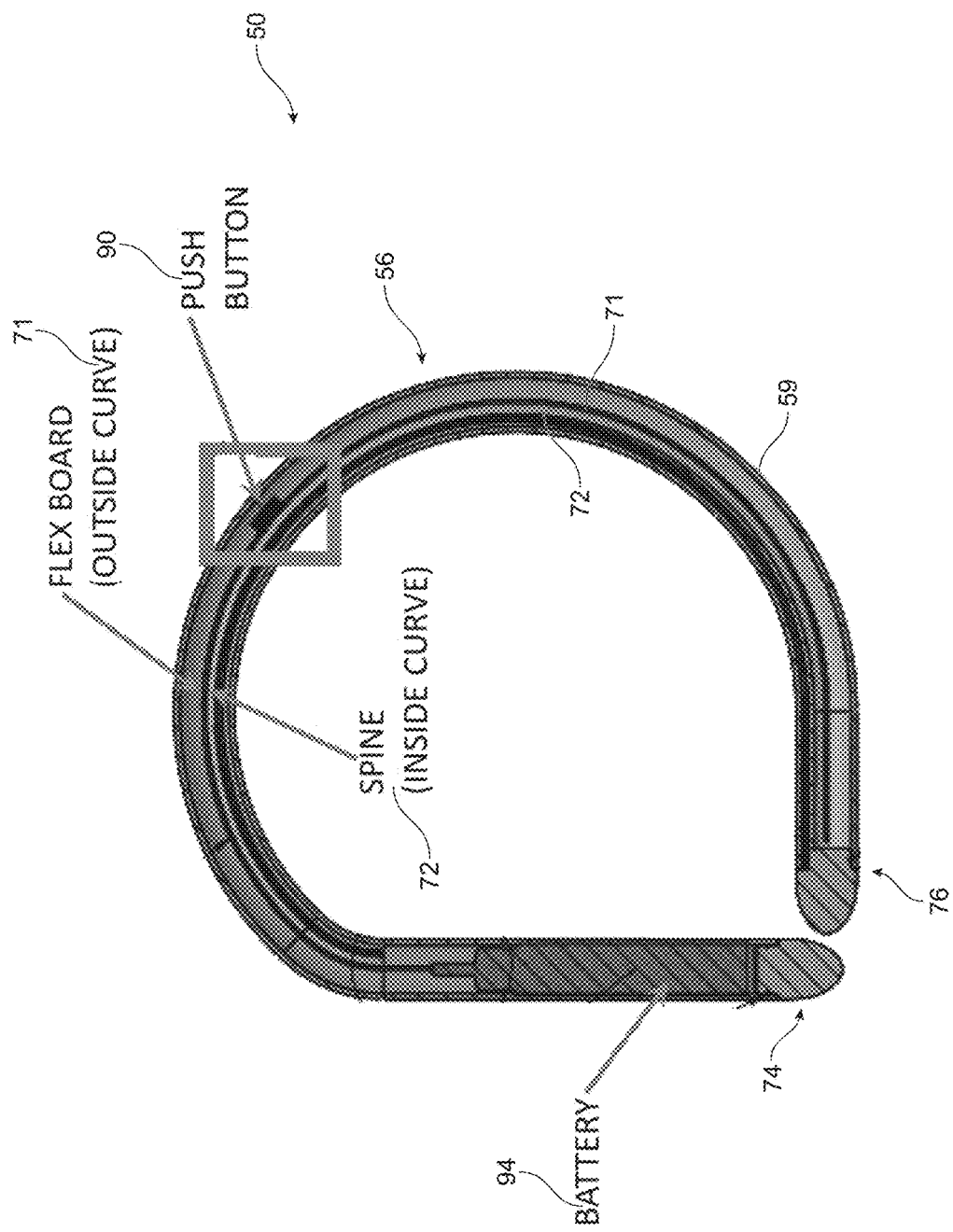
FIG. 78 shows a side view of a sensor according to this disclosure.
Figures 84, 85, 86:
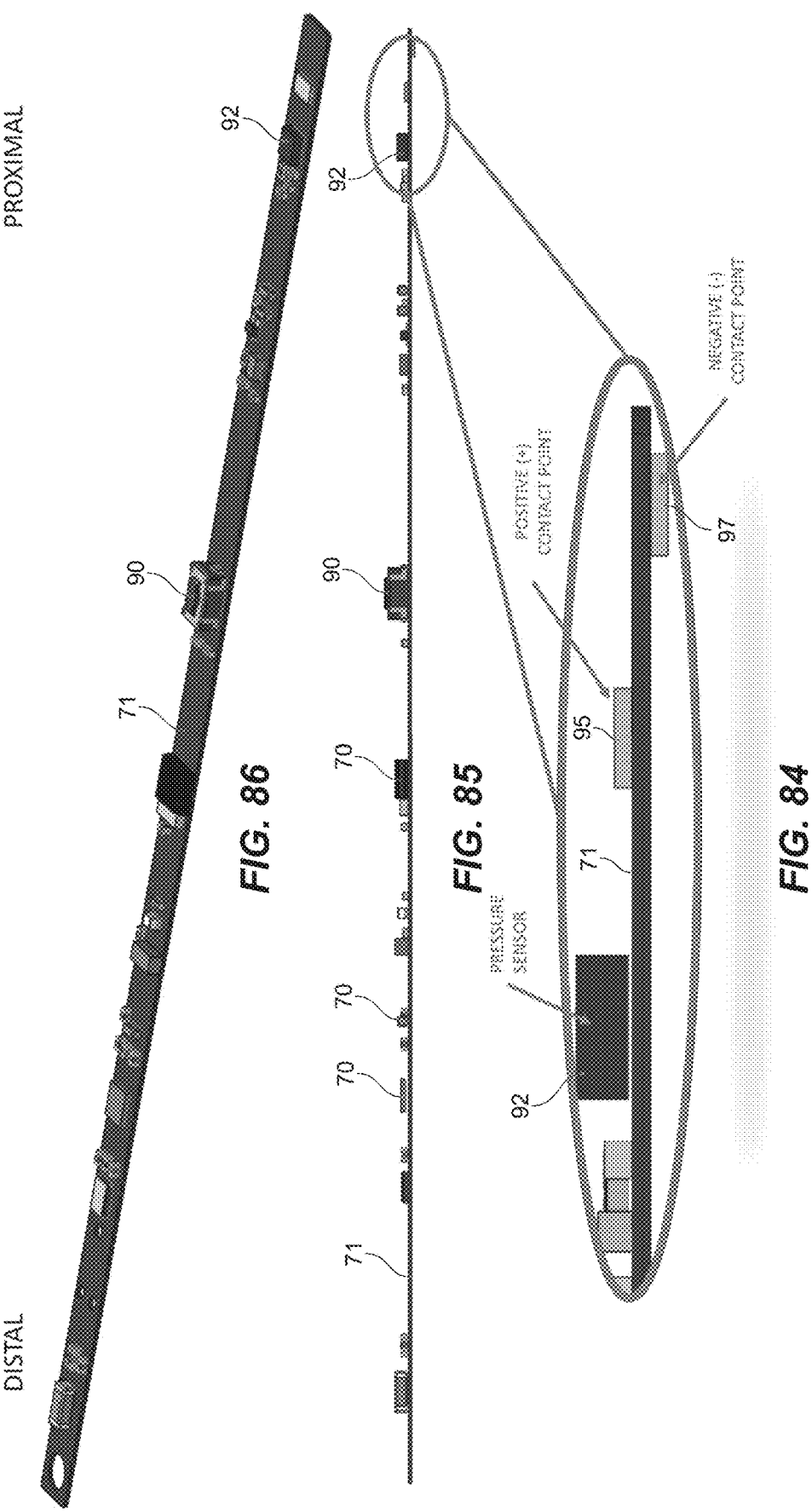
FIGS. 84-86 show side views, and a side perspective view of some internal components of a sensor according to this disclosure.

FIGS. 65-68 are of the positive contact for the battery. FIG. 69 shows leakage results for tests using different gauge needles. FIGS. 70-71 show the sensor flexibility of different sensor designs. FIGS. 73-74 show close up means of outer sheath ends that are non-radiused (57A) and radiused (57B).

FIGS. 75-78 are assembly drawings of forming the flexible circuit board 71 with electronic 70, the spine 72, and the battery 94. FIG. 77 is a top view of a sensor 50. FIGS. 79-82 show positive and negative contacts, 95 and 97, respectively, for battery 94. FIGS. 84-91 show various components of flexible circuit board 71.

Figure 93:
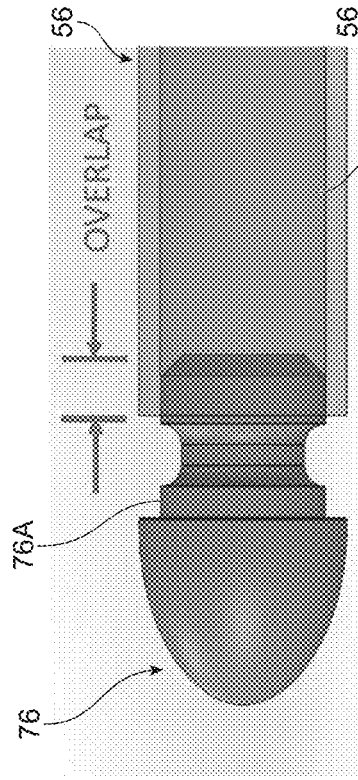
FIGS. 93-95 show side views of a distal end cap being connected to an outer tube of a sensor.
Figure 94:
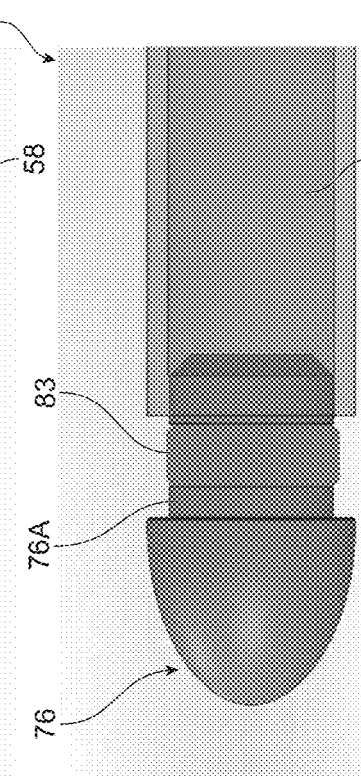
Figure 95:
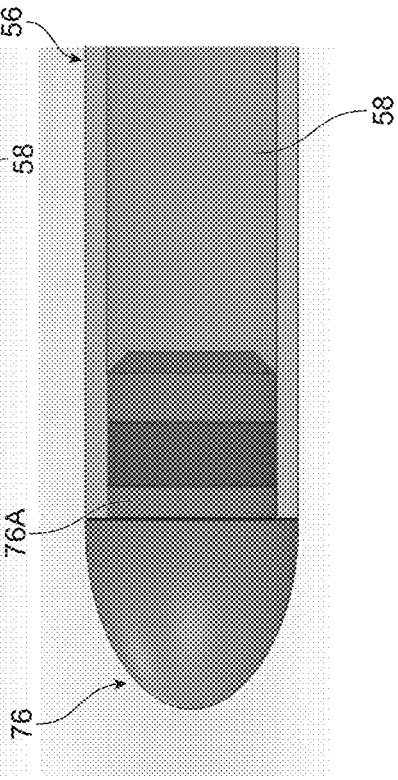
Figure 97:
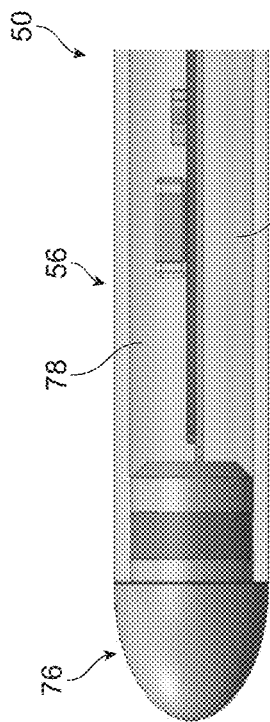
FIGS. 96-97 show partial side views of the distal end of a sensor illustrating needles for filling the sensor with silicone oil and for releasing air.
Figure 96:
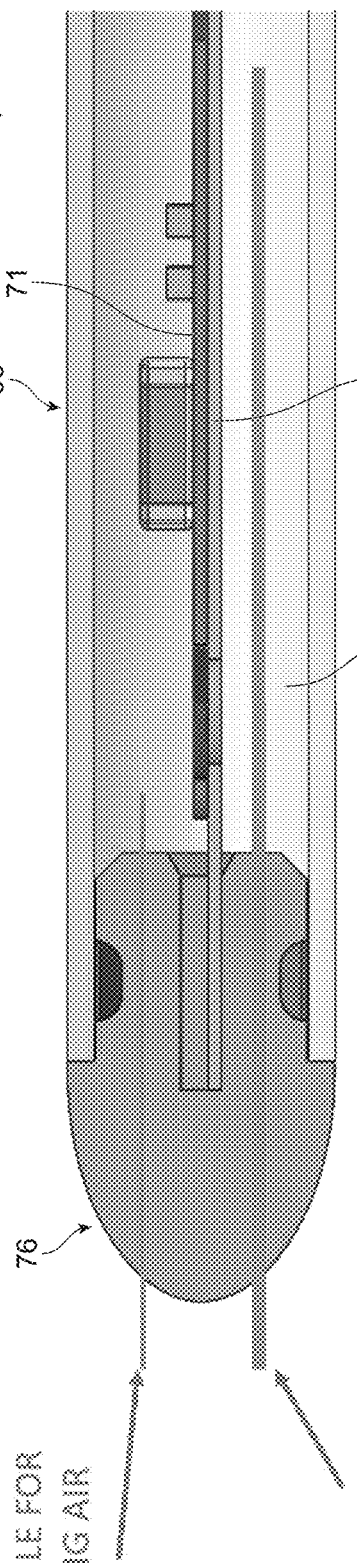

FIGS. 93-95 show the placement of the distal end cap onto outer sheath 56 by using silicone adhesive 83. FIGS. 96-97 illustrate filling the cavity of sensor 50 completely with silicone oil after applying the distal end cap 76.

Figure 99:
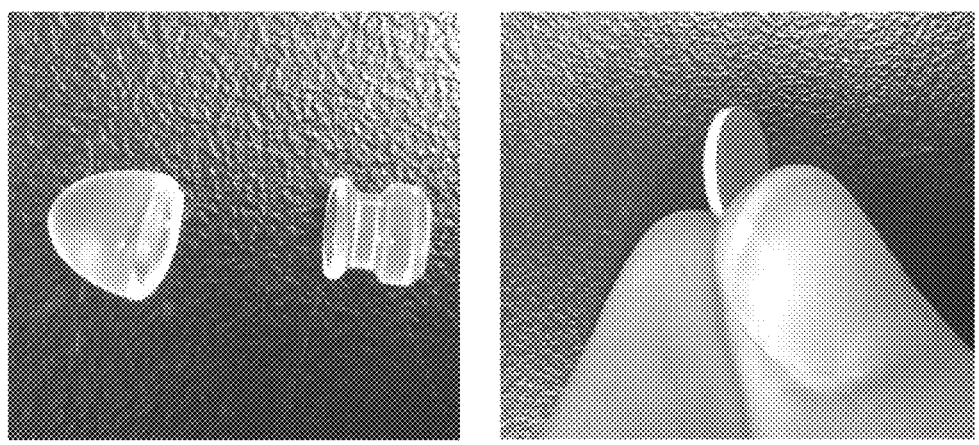
FIGS. 98-99 show views of an example distal end of a sensor according to this disclosure that has a septum.
Figure 98:
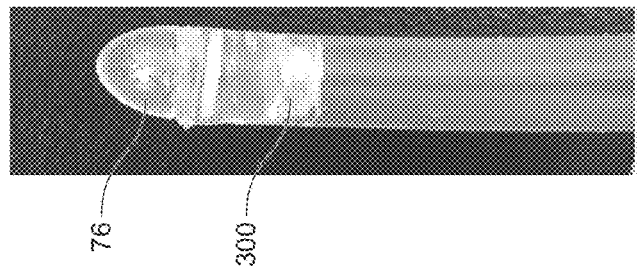

FIGS. 98-99 illustrate an experiment of adding a septum 300 to a distal end cap 76. FIGS. 100-101 are shown exemplary oils for testing purposes.

Figure 102:
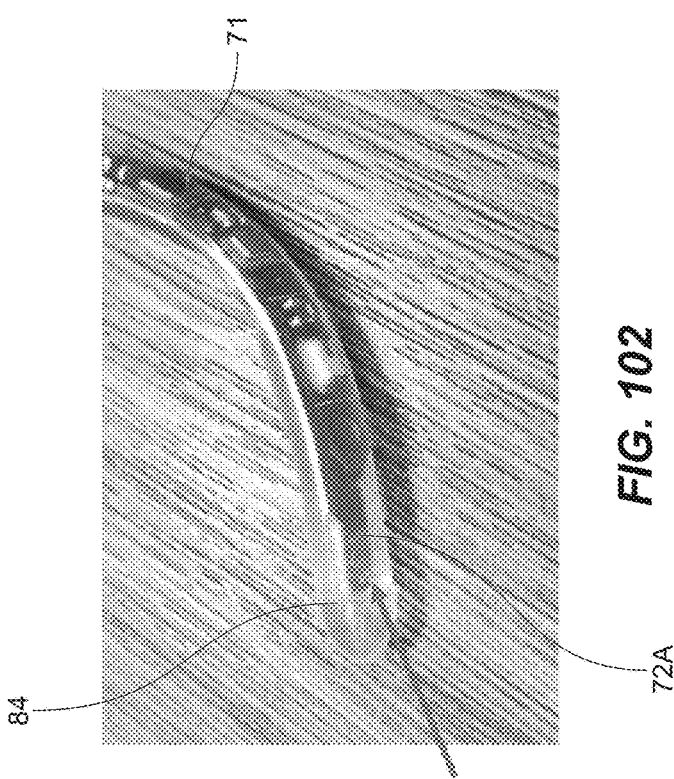
FIG. 102 is a partial, side perspective view of a sensor showing the interaction between the spine and the distal end cap and the end of the spine being encased in a plastic spacer.
Figure 108:
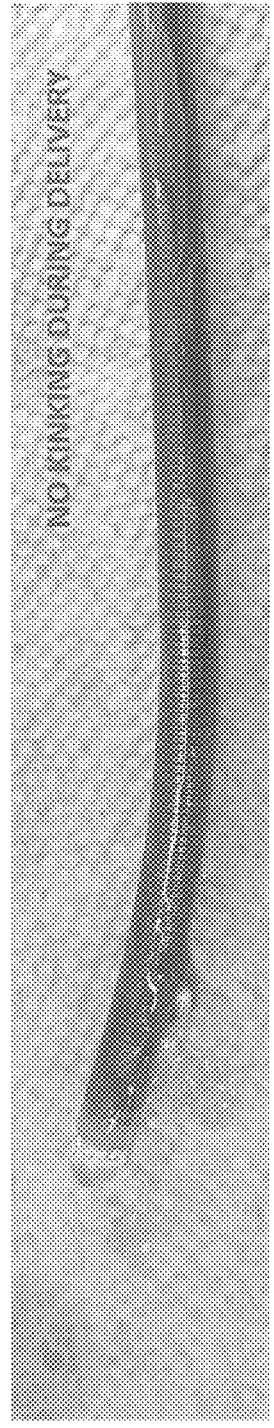
FIG. 108 illustrates the forces required to pull a sensor into an insertion tool and to push a sensor out of the insertion tube.
Figures 113, 114, 115, 116, 117:
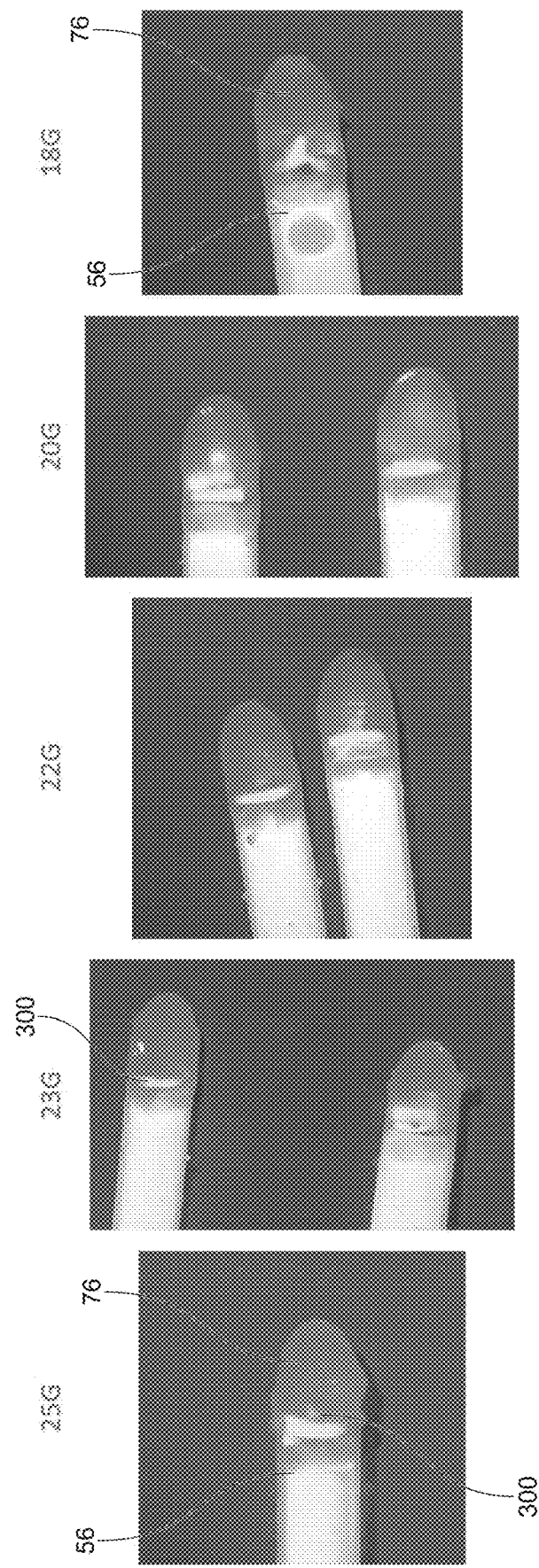
FIGS. 113-117 show partial side views of distal ends of sensors having septas and determining no leakage with an 18 G needle.

FIG. 102 shows an end 72A of spine 72 embedded in a spacer 84 of soft plastic to prevent end 72A from damaging tube 56. FIGS. 103-105 show a stem 504 of an insertion tool 500. Stem 504 has a plastic inner portion 504A surrounded by braided wire 504B. FIG. 105 shows a sensor inside of a stem 504 and shows the coude distal end cap 76 extending therefrom. FIGS. 106-107 are further examples of sensors 50 inside of a stem 504. FIG. 108 describes the process of pulling a sensor 50 into an insertion tool 500 and the forces required to move sensor 50.

FIGS. 109-112 depict the spine 72 flexion analysis. FIGS. 113-117 show that there was no leakage was found when using needles of 25 G, 23 G, 32 G, 20 G, and 18 G to completely fill a sensor cavity 58 with silicone oil when a septum 300 was used at the distal end cap 76 of sensor 50. FIG. 118 is a fill analysis using different gauge needles.

Figure 119:
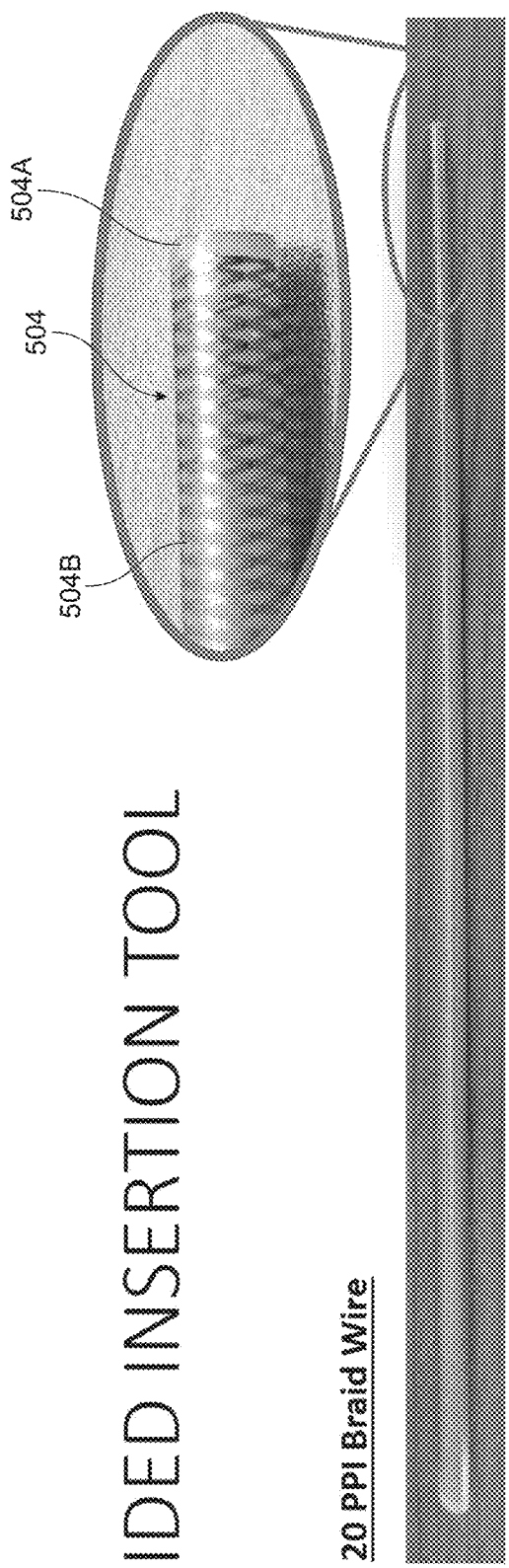
FIGS. 119-120 are side views of insertion tool stems with wire braid over an extruded plastic or silicone rubber tube.
Figure 120:
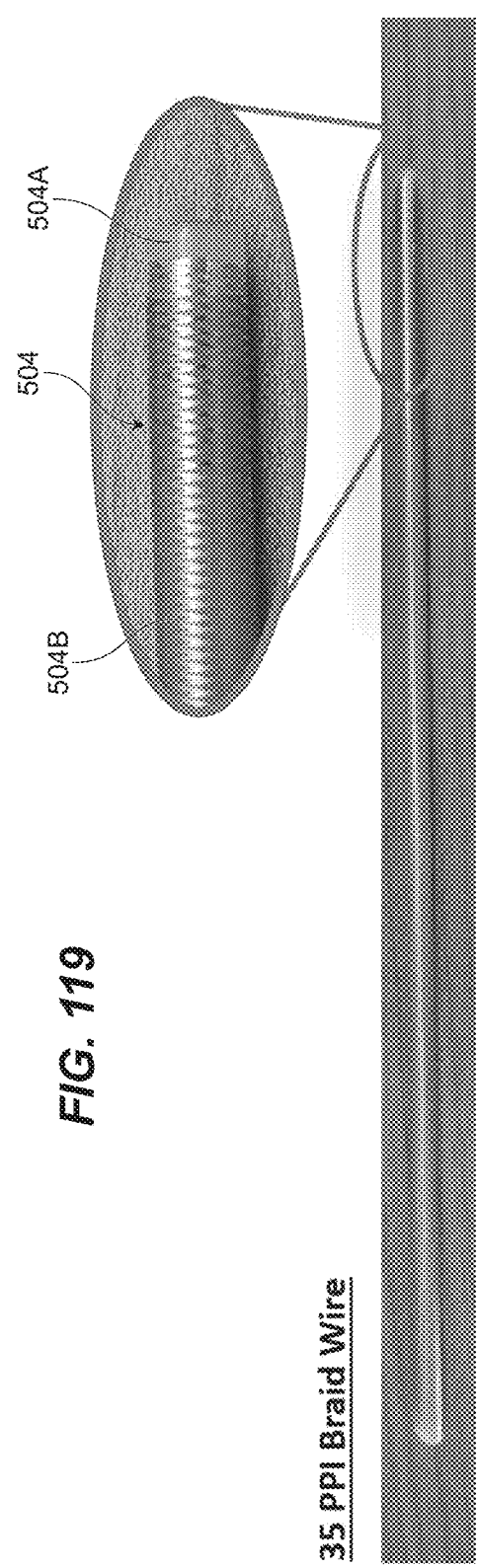
Figures 123, 123A:
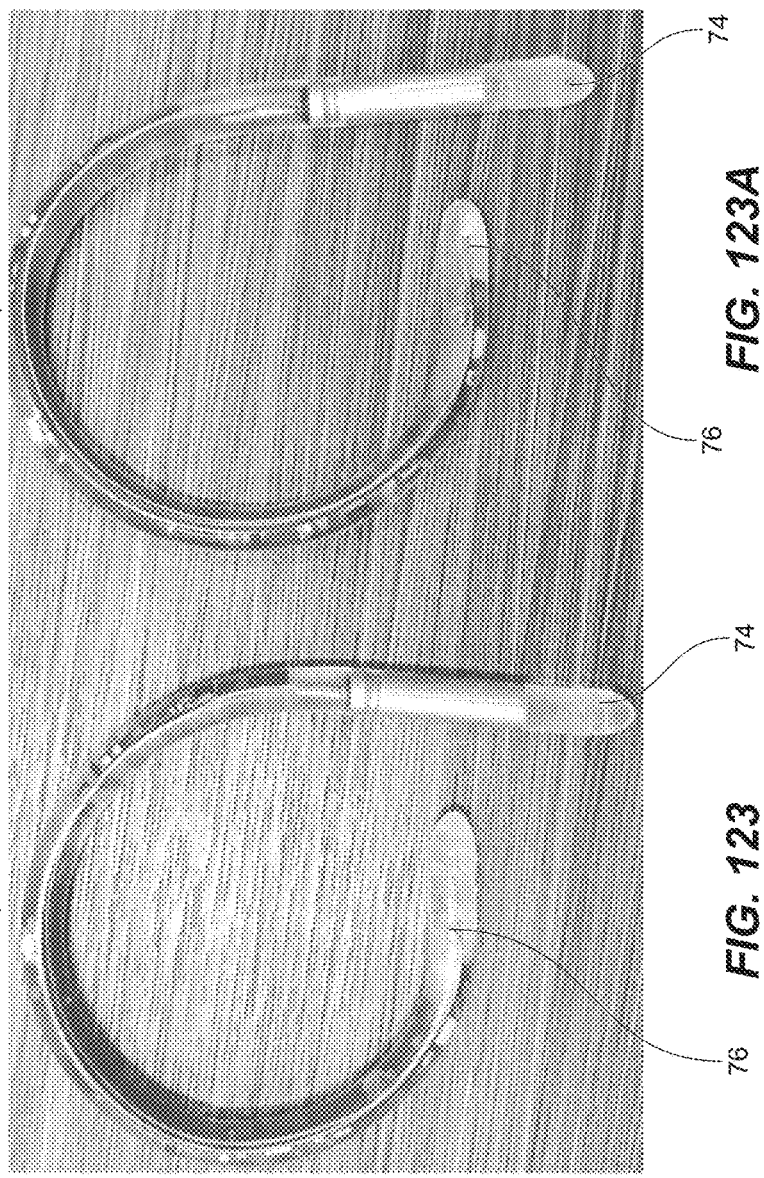
FIGS. 123 and 123A show side views of sensors that include an alternate spine that is a waterjet cut spine.

FIGS. 119-120 show additional examples of an insertion tool 500 stem 504 comprised of an inner plastic tube 504A surrounded by a wire braid 504B. FIGS. 122-123 show further examples of a sensor 50 positioned in a stem 504 of an insertion tool 500. FIGS. 123-123A are top views of sensors 50 illustrating that they returned to the correct shape after being flexed.

Figure 127:
FIGS. 127-128 include top views of a spine showing the change in diameter after flexion/extension cycles.
Figure 128:
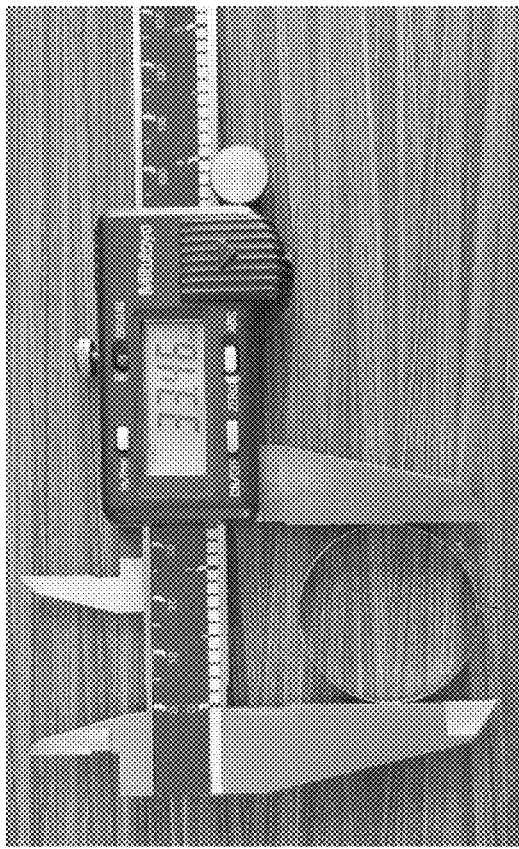
Figure 133:
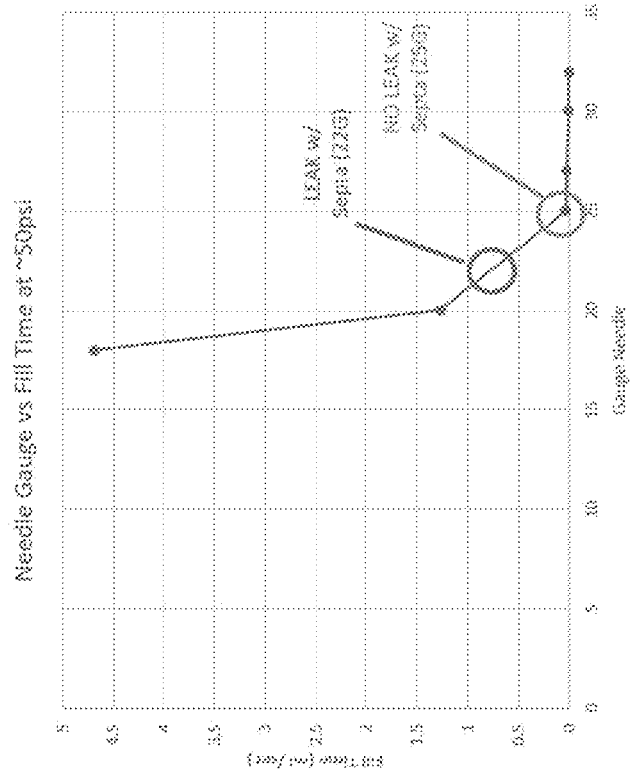
FIG. 133 shows leakage results for sensor distal ends with and without a septum using different gauge needles.

FIGS. 124-126 show a plastic spacer 84 covering end 72A of spine 72. FIGS. 127-128 show the difference in diameter of a spine 72 after 10 flexation cycles. FIG. 129 shows a material/oil testing chart. FIGS. 130-132 show leakage results when completely filling the cavity 78 of tube 56 using various needles with or without a septum FIG. 133 shows a chart of needle size analysis.

Figure 139:
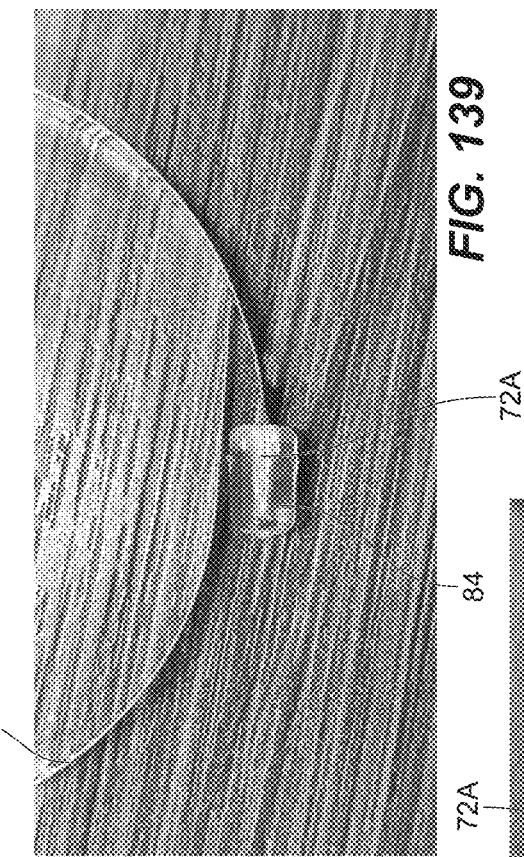
FIGS. 138-140 show top, perspective views of a distal end cap spacer attached to a spine of a sensor according to this disclosure.
Figure 138:
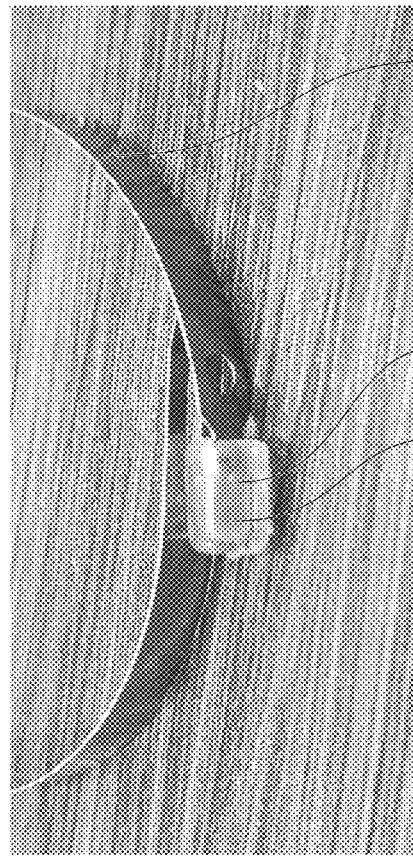
Figure 140:
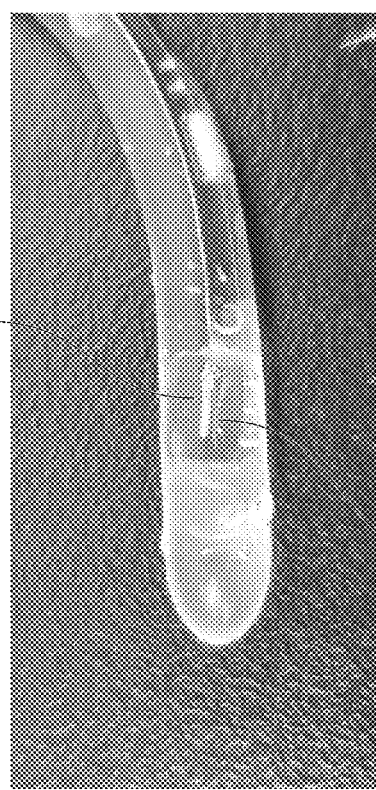
Figure 144:
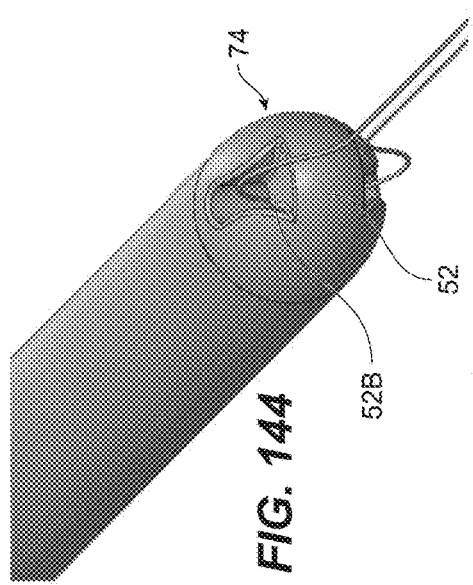
FIGS. 144-147 show a proximal tip that may be used with a sensor according to this disclosure.
Figure 145:
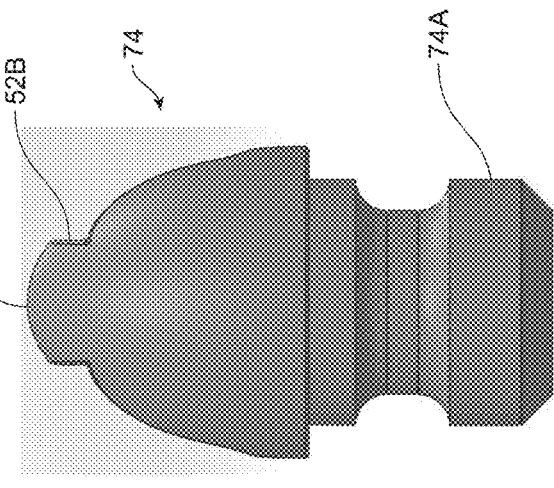
Figure 147:
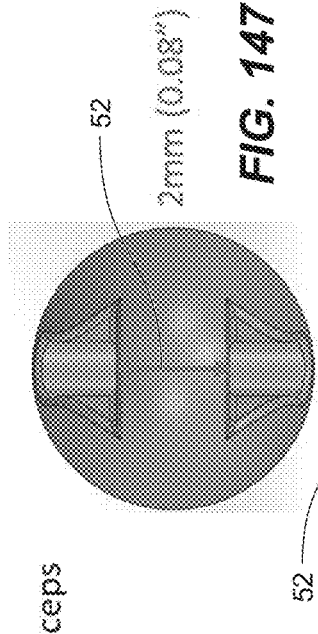
Figure 146:
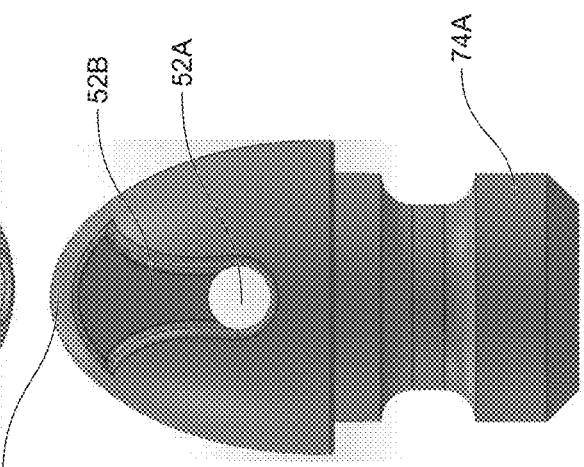

FIGS. 134-137 show a sensor 50 being pulled into an insertion tool 500 and then being pushed out by push rod 530. FIGS. 138-140 illustrate the distal spacer for end 72A of spine 72.

Figure 148:
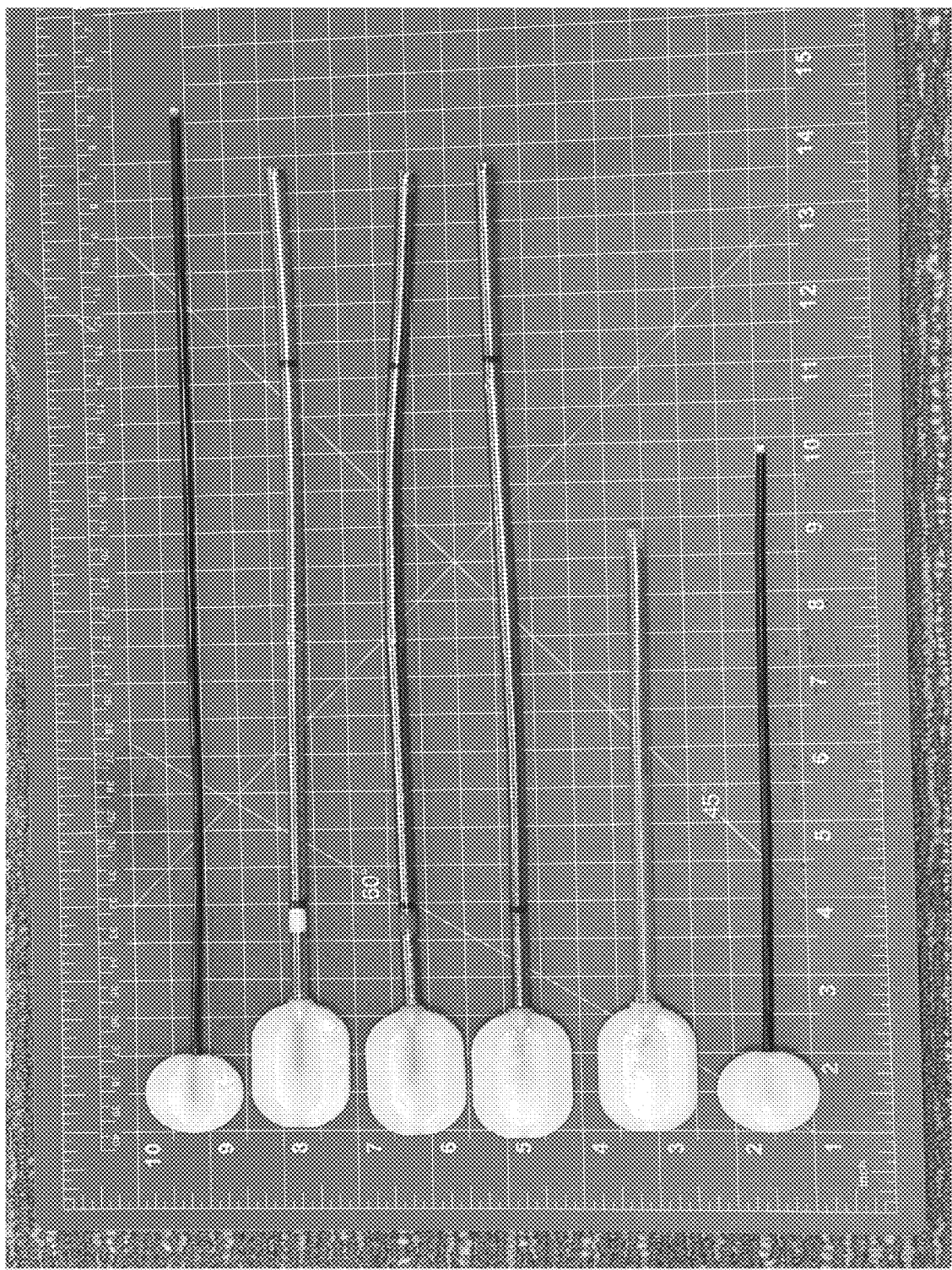
FIG. 148 shows different handles of this disclosure connected to different insertion tools of this disclosure, and push rods of this disclosure having different lengths for a male anatomy, which are longer, and a female anatomy, which are shorter.

FIGS. 141-142 show packaging for a sensor 50, an insertion tool 500 and a push rod 530. FIGS. 144-147 show a proximal cap end 74. FIG. 148 illustrates different insertion tools 500, wherein the top four are for use by males and the bottom two are for use by females.

Figure 149:
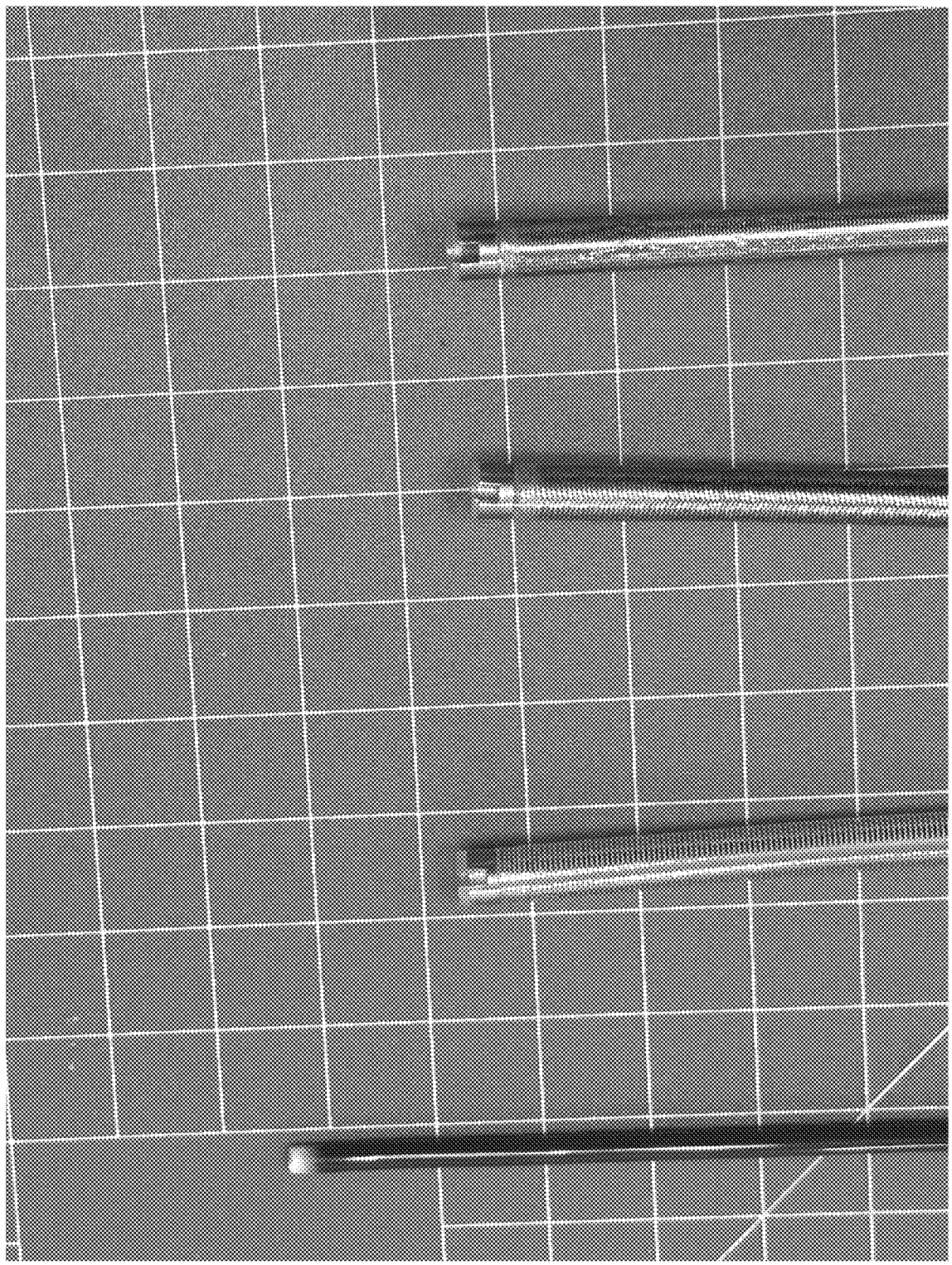
FIG. 149 shows distal ends of insertion tools of this disclosure having keyways configured to receive a key on a distal end of a sensor.
Figure 150:
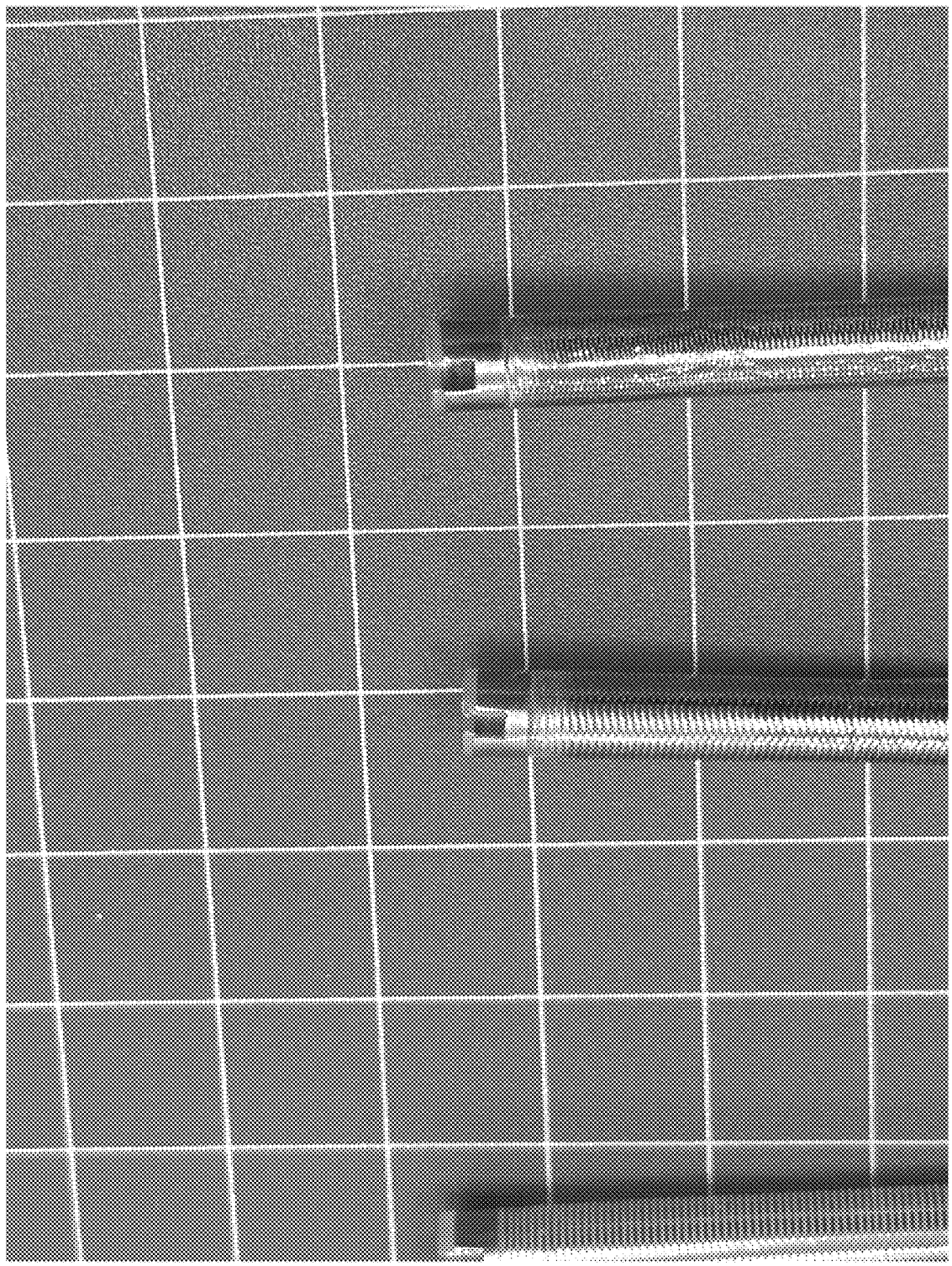
FIG. 150 shows distal ends of insertion tools of this disclosure having keyways configured to receive a key on a distal end of a sensor.

FIGS. 149-150 show the tips 516 of insertion tools and the keyways (or sheath tip inserts) 518.

The sensor distal end cap 76 is preferably a coude-shaped tip and has a key projection (or key) formed therein. The key is configured to be received in a keyway (or slot) at the distal end of the insertion tool sheath. Although any suitable method of manufacture may be used to make the distal tip of the sensor, it can be manufactured by injection molding the distal end cap 76 in 70A durometer silicone rubber to form the desired shape. The insertion tool 500 sheath at its distal end 516 may include a stainless steel ring with the keyway 518 which may be covered in a plastic applied using a reflow process. The keyway 518 in the sheath may, however, be formed in any suitable manner. Integration of the key of the distal end cap 76 with the keyway 518 is done by manually positioning the two structures adjacent to one another and the bend of the coude tip of end cap 76 biases the key into the keyway 518. This mates the key with the keyway 518 so the sensor 50 and insertion tool 500 rotate together, but also permits the sensor 50 to be pushed forward and out of the insertion tool 500 and into the bladder.

The sensor 50 also includes a proximal end (or proximal insert, or proximal endcap) 74 that is inside the lumen of the insertion tool 500 when the sensor 50 is moved into the lumen of the insertion tool 500 sheath 504. The proximal end cap 74 has a shape that engages with a geometric shape of the beginning of the second, proximal section 514 (also called a D-lock) of the insertion tool lumen, so that rotation of the insertion tool 500 translates rotational force to the sensor 50. This enables the proximal endcap 74 of the sensor 50 to provide rotational force to the sensor 50 when the handle 503 or sheath 504 of the insertion tool 500 is rotated. Thus, the sensor 50 can be rotated by a two-point connection with the insertion tool—one at the distal end of the sensor and one at the proximal end of the sensor, although only one connection need be used.

The distal end cap 76 and proximal end cap 74 of the sensor 50 may be attached to the sensor tube (or housing, or tube, or outer sheath, or sheath) 56 by over-molding, gluing, or otherwise attaching rigid or semi-rigid inserts (proximal end cap and distal end cap) 74, 76 into the lumen 78 of the sensor tube 50, or using an extrusion with a custom-shaped die or using reflow with a custom shaped mandrel. The durometer of the proximal endcaps 74, 76 of the sensor 50 is also 70A, although any suitable material, hardness, or shape may be used.

The insertion tool 500 may have a 18Fr OD and a 16 Fr ID in the first, distal section where the sensor 50 is positioned and have a smaller cross-sectional area in the second, proximal lumen between the sensor 50 and the handle 503. The smaller cross-sectional area is configured to be too small for the proximal end cap 74 of the sensor 50 to pass through.

The combination of both the proximal and distal endcaps 74, 76 in the sensor 50 and insertion tool 500 enable reliable translation of rotational force from the handle 503 (or outer sheath 504) of the insertion tool 500 to the distal end 76 of the sensor 50. The coude, distal tip 54 at the distal end cap 76 aids clinicians in moving the sensor 50 through the urethra and into the bladder. If the clinician is unable to properly orient the sensor 50 including its distal tip 54 by rotating it via rotation of the insertion tool 500, it could result in injury or trauma to the patient's anatomy when trying to deploy the sensor into the bladder, and also prevent the clinician from successful insertion of the sensor into the bladder. This is helpful for both male and female anatomies. The insertion tool 500 may be shorter and stiffer for females due to the differences in anatomy.

The sensor 50 may incorporate a rigid or semi-rigid material such as stainless steel to enable reliable shape memory via a spring 72. This may be a variety of symmetric or asymmetric shape(s) in order to provide the proper spring rate for the application. In some embodiments the spring 72 may be heat treated and/or rolled to create the spring/return rates desired. The spring (or spine) 72 may also be integrated into the circuit board 71 and be welded to the battery 94. At the opposite end the spine 72 may be attached to a plastic spacer 84 to prevent any potential for the spine 72 to puncture the housing 56 of the sensor 50 and maintain patient safety. In this embodiment, linear force can be translated from the proximal end cap 74 of the sensor 50 to the distal end cap 76 of the sensor 50 by using the battery 94, spine 72, and plastic spacer 84.

The design of the sensor materials and components provide reliable integration with the insertion tool. For example, the sensor spine 72 and housing 56 utilize material with properties to enable repeated and reliable memory to maintain the desired shape when in the first position in the bladder so the sensor 50 does not migrate out of the bladder once positioned therein.

The sensor spine 72 is preferably made of 301 stainless steel (SS) and formed using a rolling process, although any suitable material and process may be utilized The hardness and material of the sensor 50, and of the sensor spine 72 must be such that it rebounds to the desired first, curved or circular shape and does not lose its shape memory after straightening. If the sensor 50 does not maintain the proper shape and orientation, then it may lead to undesirable outcomes such as migration out of the bladder and/or injury to the lower urinary tract.

The sensor 50 uses materials and an assembly process that also provide reliable translation of force linearly when the sensor 50 is straightened. To assemble the sensor 50, a metal contact is laser welded (although any suitable method may be used) to the battery 94 and soldered (although any suitable method may be used) to a flexible electronic circuit board 71. The sensor spine 72 is laser welded (although any suitable method may be used) to the battery contact. The flexible electronic circuit 71 is then attached to the spine 72 for rigidity and support. At the distal end cap 76 of the sensor 50, the sensor spine 72 is attached to a small plastic spacer 84 so the spine 72 will not push through or tear the sensor outer wall (or housing) 56. The distal sensor endcap 76 is preferably attached to the plastic spacer 84 and to the sensor housing 56 such that there is linear translation of force using rigid or semi-rigid components from the proximal endcap 74 to the distal endcap 76.

The materials and processes are selected in order to achieve a desired range of rebound (or memory) and strength of the sensor spine with the strength and rigidity of the insertion tool sheath such that there is a desired level of curvature before the sensor is inserted in the sheath. These structures offer a combination of flexibility and pushability for the clinician to insert the sensor safely and reliably in the bladder.

The insertion tool 500 and sensor 50 may be constructed in a manner to allow for insertion without a pushrod 530. In this embodiment, the mechanical properties of the sheath 56 and sensor 50 may be optimized such that it offers characteristics for insertion through the urethra and into the bladder. This may allow for more ergonomic insertion and safe handling of the device for clinicians because the tool is shorter and has one less component to handle during the insertion process.

In some embodiments the insertion tool 500 sheath 504 may utilize multiple durometers of material (e.g., stiffer at the proximal end and softer at the distal end) as well as reinforcement from braiding or coiling the exterior wall of the insertion tool sheath with different: materials, such as steel, thicknesses, and patterns.

The proximal endcap 74 may also be shaped in a manner that enables quick and easy retrieval of the sensor 50 using standard cystoscopic tools including flexible graspers or forceps. These can be utilized in the event that the removal string 58 connected to the proximal end cap 74 of the sensor fails. Due to the size of the forceps able to be utilized during cystoscopy, a specially designed shelf or rim 52B with reduced thickness can be implemented on the sensor outer sheath 56 or the proximal endcap 74 in some embodiments to enable quick and easy removal of the sensor by any trained urologist using commonly available tools. The design of such an endcap 74 enables quick and reliable retrieval using standard flexible cystoscopes and commonly available tools.

Packaging 700 for the sensor 50 and insertion tool 500 may be designed in a manner to facilitate efficient and safe clinical workflow. This may enable the clinician to insert the sensor into the patient's bladder without touching the sensor body. This requires the packaging 700 to be protective but flexible to enable the push of the sensor button through a packaging barrier in order to activate the sensor. This also requires support for the sensor 50 and the insertion tool 500 so that the string 58 can be preloaded in a reliable and effective manner such that the coude tip 54 of distal end cap 76 is properly aligned in the distal end of the insertion tool 500 for insertion into the bladder. This helps to minimize any potential contamination of the sensor, which may reduce complications such as urinary tract infections and bacterial inoculation of the bladder. The packaging 700 can be designed in a manner to support both the female and male insertion tools with the same shell/tray.

Each key/keyhole feature may be constructed of common materials (silicone, plastic) and also reinforced by rigid or semi-rigid materials (e.g., metal such as stainless steel) to improve the strength of the engagement between the over sheath and sensor. This material can be incorporated into the design such that any metal is covered by soft/flexible plastic such as TPE/TPU to minimize or eliminate any potential trauma to the urethra and bladder during insertion and deployment into the bladder.

In some embodiments, there may be a different insertion tool 500 design for female and male anatomies. In this instance the female tool may be shorter than the male tool 500 in order to accommodate the shorter urethral length and improve ease of insertion.

If a coude or asymmetric sensor tip 54 on end cap 76 is utilized then the sheath handle 503 may have a visual and/or tactile indicator 508 to provide reliable confirmation of the sensor end cap 76 orientation for the clinician to properly insert the sensor 50 into the male or female anatomies.

In both the female and male insertion tools 500 the design of mechanical components may take into account the mechanical properties of the sheath to enable safe and reliable delivery of the sensor 50 into the bladder through the urethra. This includes the materials and properties of the sensor housing 56 (durometer and material), the sensor spine 72 (material and spring rate) when considered with the sheath 504 (material), and sheath construction methods (braiding and/or coiling). In some embodiments the sheath 504 may include braiding and coiling patterns that differ at different sections. This may offer the clinician more or less stiffness/flexibility to provide the proper characteristics for insertion.

Loading the Sensor into the Insertion Tool

As explained above, the sensor is preferably loaded into the insertion tool by pulling it into the insertion tool lumen using the removal string attached to the proximal end of the sensor. Pulling the removal string pulls the sensor into the first, distal section of the insertion tool lumen. As mentioned previously, the proximal end of the sensor cannot fit through the second, proximal section of the insertion tool lumen so it cannot advance past that point. When fully positioned in the insertion tool, the removal string is outside of the proximal end of the insertion tool sheath, the proximal tip (i.e., the most proximal part of the proximal end) of the sensor is positioned inside the beginning of the second, proximal lumen of the insertion tool, and the distal end of the sensor is positioned outside of the distal end of the insertion tool sheath. The key (if utilized) on the distal end of the sensor is positioned in the keyway of the distal end of the insertion tool, and the geometric structure (preferably rectangular) of the proximal tip of the proximal end of the sensor is received in and engages a mating structure (preferably a rectangular opening) at the beginning of the second, proximal section of the insertion tool lumen.

Advancing (or Push) Rod

The advancing rod 530 is described above and is designed to provide a combination of flexibility and pushability enabling reliable sensor deployment. It is a flexible tube with a handle that has a lumen in the middle enabling urine to flow through the tube. This aids clinicians in confirmation that the device has been deployed in the bladder successfully. The pushrod 530 may also contain a lumen running the length of the rod and through the handle. This feature is useful to enable urine to flow through the pushrod and out of the pushrod handle which enables clinicians to confirm placement of the sensor into the bladder.

Sensor Performance and Cavity Fill

The sensor uses a combination of silicone rubber for the outer wall (or housing, or tube), adhesive, and silicone oil in the sensor cavity. The silicone oil has properties that minimize the transfer of fluid into and through the silicone outer wall and adhesive. Silicone rubber is a porous material so it absorbs certain materials and allows for transfer of fluid (as used herein, fluid refers to liquid) and gas through the silicone rubber membrane. In order to enable reliable pressure sensing for the bladder sensor, the volume of mass/fluid in the sensor housing (or cavity defined by the silicone rubber tube) should be at a preset amount or else the pressure readings could be affected by the external environment and may cause sensor drift and reduced precision. This volume should be such that when combined with the other components of the sensor there is a pressure achieved in the sensor cavity that is higher than atmospheric pressure with a minimal amount of, or no, air or gas remaining inside the sensor cavity. In this event, the higher pressure of oil inside the sensor cavity will work to push air or gas outside of the sensor cavity in an attempt to reach equilibrium with the external environment (atmospheric pressure). This is desirable as reduction of compressible gas in the sensor cavity will provide a sensor with higher frequency response than otherwise.

Filling the sensor with fluid (most preferably silicone oil, and most preferably flurosilicone oil that contains hydrophobic properties and molecules that are larger than that of the silicone rubber tube) to a pressure that is below atmospheric (e.g., less than one Bar) will permit air to move into the sensor cavity (or housing) from the outside environment through the porous silicone tube before the sensor is positioned in the bladder. In that case, air will enter the sensor cavity until the cavity eventually reaches an equilibrium pressure (e.g., atmospheric) with the external environment. Thus, the storage of such a sensor before use allows air to enter the sensor housing, which may or may not be desirable because it could dampen pressure readings. This is undesirable in certain applications unless a damping effect is desired, such as for a low-pass filter.

Fluids (i.e., liquids) disposed in the sensor housing cause the sensor to be essentially incompressible whereas gasses such as air cause the sensor to be more readily compressed. So, if air is present in the sensor cavity (or housing), it may serve to dampen the signal from the external environment of the bladder and alter the pressure reading sensed by the internal pressure sensor (which is preferably on the circuit board) in the sensor housing. Air can be used to act as a damping mechanism and filter some aspect of the signal (low pass filter). This feature can be useful if the filtering is desired.

Filling the sensor cavity to a pressure greater than atmospheric level is usually beneficial for sensor performance and manufacturing. This enables simple assembly and reduced manufacturing time because the amount of fluid, such as silicone oil, can easily be measured by volume or mass using tools such as an electronic fluid dispenser and a scale. In this embodiment, the air dampens the signal received by the pressure sensor inside of the sensor housing and decreases the frequency response of the pressure sensor as compared to a similar system in which additional fluid (i.e., liquid) replaces the air. Ultimately, there is a range of pressure/volume that can be utilized in which the pressure sensor will sense pressure at a lower frequency response than a similar system with more fluid. In this range, more air in the sensor housing decreases the frequency response and more fluid in the sensor increases the frequency response. In all embodiments, a sensor with air in the sensor housing will have a decreased frequency response than a sensor at the same pressure with no air and only liquid in the cavity. During manufacturing including more fluid may be valuable because it can enable simple assembly and increase manufacturing yield because there is less precision required and also because there a two-step filling process may be used. In this embodiment, a portion of the sensor cavity may be filled and sealed before a second step to overpressurize the sensor cavity. This can be used to allow for the precise level of air to enter the cavity and enable a specified amount of damping to the system (low/high pass filtering).

Filling the sensor housing with a volume of fluid that is higher than atmospheric pressure (e.g., greater than one Bar) will cause air/gas bubbles to expel from the sensor outer wall (or tube) and the sensor housing will reach a point of pressure equilibrium that may be higher than atmospheric pressure, as long as (1) the mass/volume of fluid in the housing is not escaping through the porous silicone tube, and (2) the mass/volume of air/gas inside the sensor is small enough so that the volume of fluid in the sensor housing is greater than the volume of the sensor cavity. This is helpful in manufacturing to increase yield and reduce the precision required but does require additional components and methods of assembly to ensure a standardized volume of liquid in each sensor housing. In some embodiments improved frequency response is desired so air/gas inside of the sensor housing should be eliminated or minimized. To accomplish this the sensor is filled with a greater volume of fluid than the volume of the sensor cavity to create a pressure in the sensor housing that is higher than atmospheric pressure. In one embodiment the sensor may be manufactured so that the pressure after air/gas is expelled from the cavity is as high as 1250-1400 hPa. Sensors that are pressurized at or above this level will not allow air/gas to enter the sensor housing under normal circumstances, and this standardizes the frequency response characteristics of the internal pressure sensor, which provides reliable and predictable pressure sensor readings with little drift and high accuracy.

To accomplish adding a volume of fluid greater than the volume of the sensor cavity, an assembly process using a two-stage fluid fill may be used. First, a volume of fluid is inserted directly into the sensor housing that is less than the final desired volume. The sensor distal endcap is then attached to the sensor tube in any suitable manner, such as with adhesive, which is allowed to dry to seal the distal tip to the sensor tube. The sensor housing can then be filled further using a syringe with a needle to poke through the distal endcap to add additional fluid into the sensor housing. Silicone rubber has self-sealing properties that may support being punctured with a syringe and then sealing afterwards, but for extra reliability the addition of a septa (e.g., a rubber septum) may be used. The septum is typically compression-molded rubber or elastomer and can withstand multiple punctures from syringe needles and self-seal thereafter. This maintains a reliable barrier to prevent the transfer of fluid/gas through the septum and, hence, out of the sensor housing. Using the septum enables the sensor housing to be pressurized with additional fluid in the second stage of assembly to levels that otherwise may not be possible because puncturing silicone rubber with a needle may cause a permanent gap or opening that would allow fluid to escape. In some embodiments, the septum may be integrated with the sensor distal endcap. In some embodiments, the septum may be integrated with both the sensor distal endcap, and also with a plastic spacer. Alternatively, the septum may only be integrated with the plastic spacer or attached to the distal or proximal end of the sensor in any suitable manner.

The material properties of the septum may be selected for use with a specific needle size/shape for precision in filling. In this case, the amount of fluid volume in the sensor housing may not need to be measured because excess pressure will bleed off after reaching a target pressure because of leakage from the septa and/or silicone needle punctures. This may aid in manufacturing and offers a range (1250-1400 hPa) of values acceptable which increases yield and reduces time/precision required.

Septas are made by a compression molding technique that creates a "self-healing" feature such that needles may puncture the septa without creating holes that would jeopardize the mechanical integrity of the sensor cavity. In some embodiments a septa may be incorporated into the design for a spine spacer and include multiple filling holes for a syringe to fill the sensor cavity with fluid.

In other embodiments, the septa may be integrated into the sensor spacer and sealed prior to final attachment of the sensor endcap. This may offer improved reliability of sealing and reduce complexity of assembly by reducing the distance that the needle is required to travel through the silicone. In this embodiment, a larger needle size may be utilized to speed the flow of fluid into the sensor cavity.

If the sensor cavity is pressurized to a level that will still maintain a pressure greater than atmospheric level after elimination of any compressible fluids and there is little or no loss of molecules of the remaining fluid (such as silicone oil), then the sensor cavity pressure will remain stable thereby increasing the potential service life and/or shelf life of the sensor. This may be beneficial for any commercial activity and to enhance the supply chain and logistics for the sensor. This may also reduce or eliminate any need for calibration or recalibration of the sensor so that the pressure sensor (or pressure monitor) that is part of the sensor circuitry will produce accurate readings of the bladder pressure.

In one embodiment, the sensor may actively transmit the pressure of the sensor cavity to aid in manufacturing. In another embodiment, the method of filling the sensor with fluid may be automated such that a closed loop is created by software that receives a signal from the pressure sensor and fills the cavity with fluid until the sensor cavity reaches a pressure threshold that may slow or cease the fluid filling in the sensor cavity.

If desired, some embodiments of the sensor may incorporate the use of compressible fluids, such as air. This may be valuable to act as a low-pass filter and remove undesired artifact from signal from the sensor's internal pressure sensor. This damping effect is correlated to the amount of air in the sensor and pressure of the sensor cavity and will decrease the frequency response of the system Conversely, greater pressures in the sensor cavity may work to increase the frequency response of the system, which is desirable in certain situations.

The sensor can sense conditions inside of the bladder and electronically communicate the data, preferably by wireless communications, to a computing device having a processor and software configured to receive the data, analyze the data, compare the data to relevant data, display the data, and/or store the data.

Computer System

Figure 159:
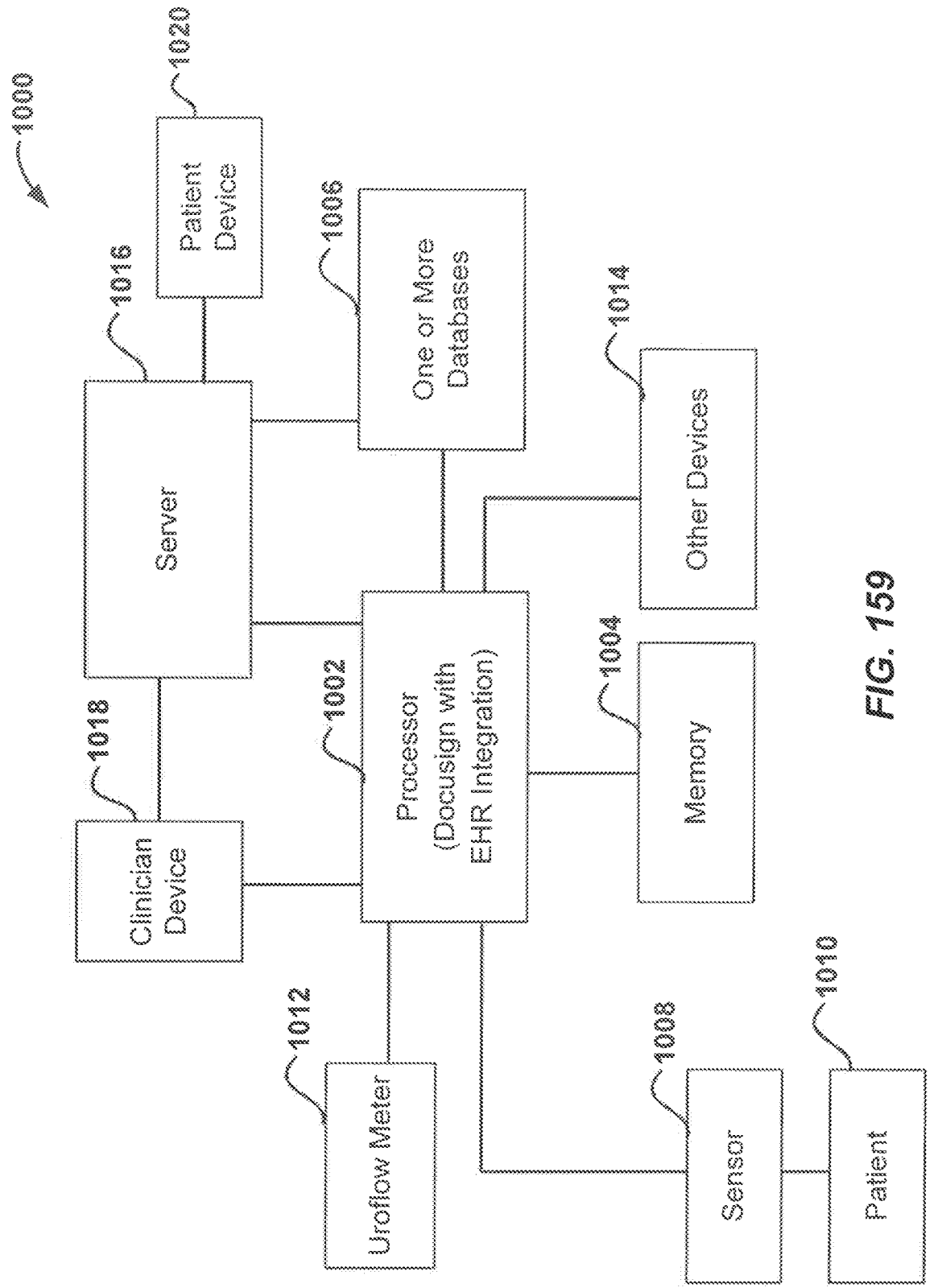
FIG. 159 is a block diagram of a computer system 1000 that may be utilized with aspects of this disclosure.
Figure 160:
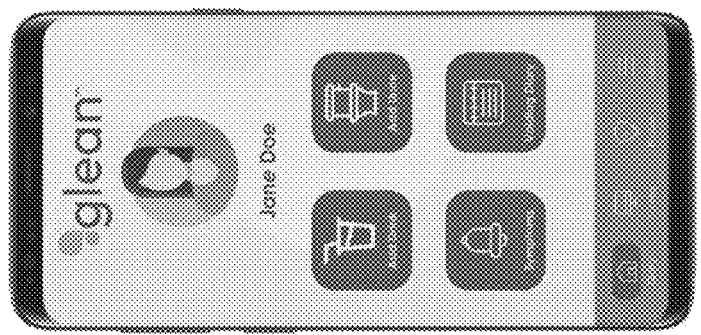
FIG. 160 shows an alternate screen shot generated by a computer system that may be utilized with aspects of this disclosure.
Figure 162:
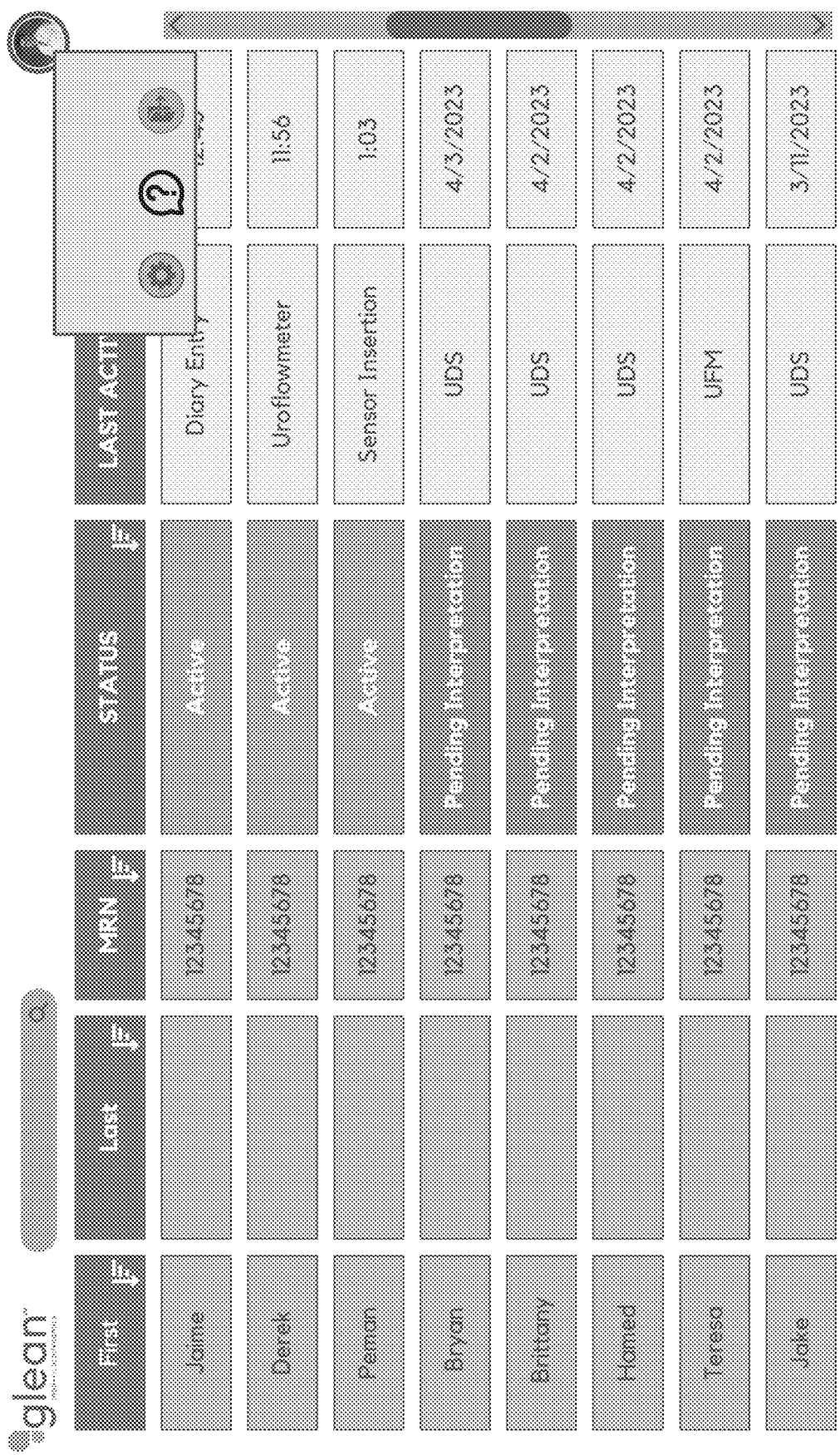
FIG. 162 shows an alternate screen shot generated by a computer system that may be utilized with aspects of this disclosure.
Figure 163:
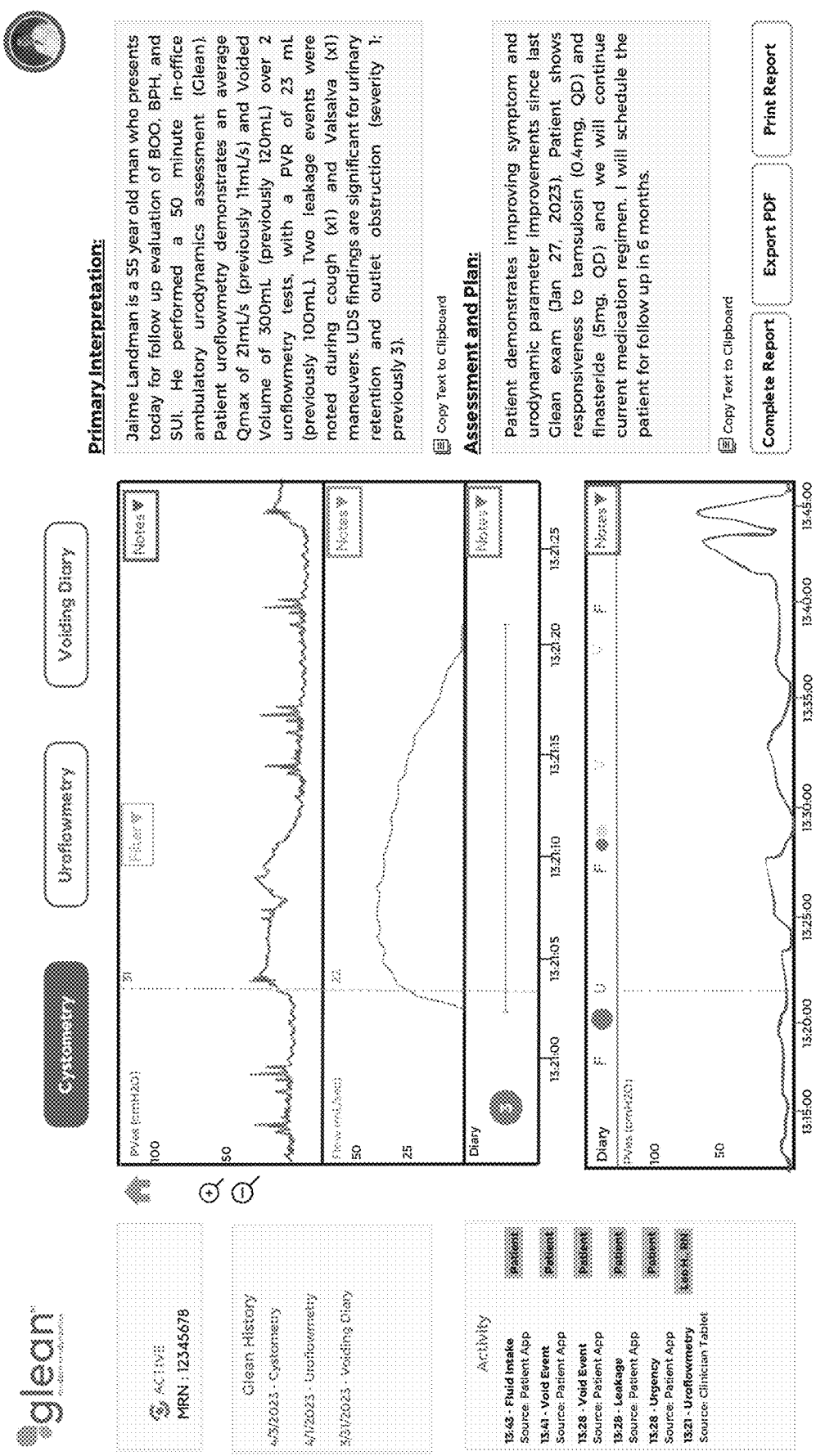
FIG. 163 shows an alternate screen shot generated by a computer system that may be utilized with aspects of this disclosure.
Figure 164:
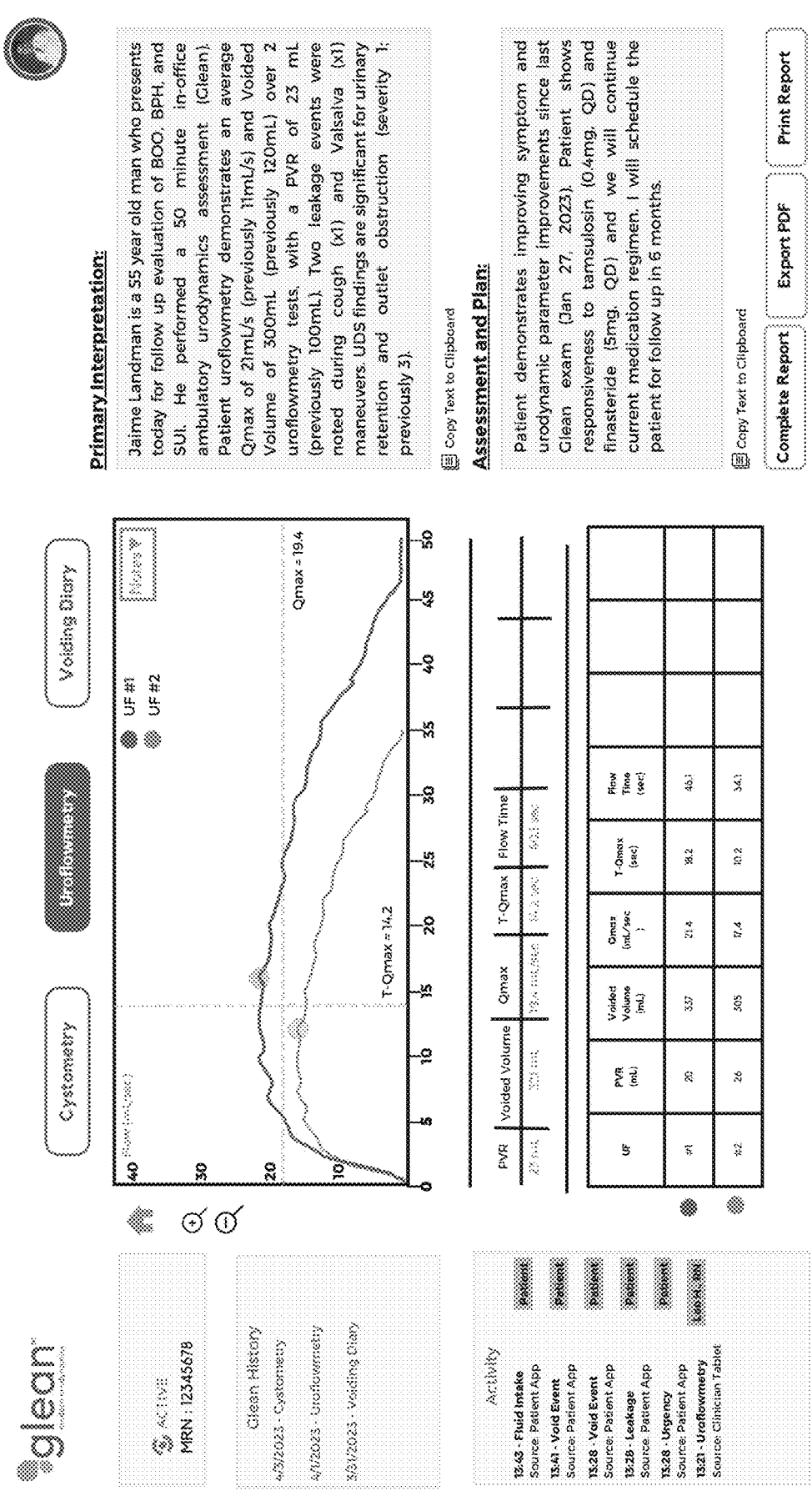
FIG. 164 shows an alternate screen shot generated by a computer system that may be utilized with aspects of this disclosure.
Figure 165:
FIG. 165 shows an alternate screen shot generated by a computer system that may be utilized with aspects of this disclosure.

FIG. 159 shows a computer system 1000 according to this disclosure. Computer system 1000 has a processor 1002 having a memory 1004, and in communication with one or more databases 1006. Databases 1006 can store any urological data for any number of patients. This data can be accessed by processor 1002 for comparison to data for patient 1010 for any purpose, such as to examine trends or determine if patient 1010's data is unusual or deviates from normal.

Processor 1002 is in communication with a sensor 1008, which is any sensor resident in the bladder of patient 1010, such as any of the sensors described in this disclosure. Sensor 1008 provides urological data regarding patient 1010 to processor 1002 for analysis. Processor 1002 may also be in communication with a uroflowmeter 1012, which either weighs or determines the volume of urine for a voiding episode. The data from uroflowmeter 1012 can be included with data from sensor 1008 or analyzed separately.

Data from sensor 1008 and/or uroflowmeter 1012 may be compared to and/or added to data from one or more databases 1006, and stored in memory 1004 and/or one or more databases 1006.

Other devices 1014 are one or more other devices that may provide information from processor 1002 or receive information from processor 1002.

A clinician device 1018 is any suitable computing device, such as a tablet, desk top computer, or cellular phone. Clinician device 1018 may communicate directly with processor 1002 or indirectly with processor 1002 through server 1016. Clinician device 1018 receives data from processor 1002 and displays it in any manner depicted herein such that the data is easily organized and simple to interpret. Clinician device 1018 is configured to pre-populate reports with the urological data of patient 1010, which leads to significant time savings. Using the clinician device 1018, a clinician can review a report and electronically sign or verify it using the docusign (or electronic signature) function of processor 1002 and the report can then be stored as an electronic health record (EHR) in either memory 1004 or one or more databases 1006.

A patient device 1020 is in indirect communication with processor 1002 and clinician device 1018 via server 1016. Patient device 1020 is any suitable device such as a computer or cellular phone. Patient device 1020 may receive urological information from clinician device 1018 or processor 1002 and present it to patient 1010 in any suitable manner, such as those shown in this disclosure.

Figure 151:
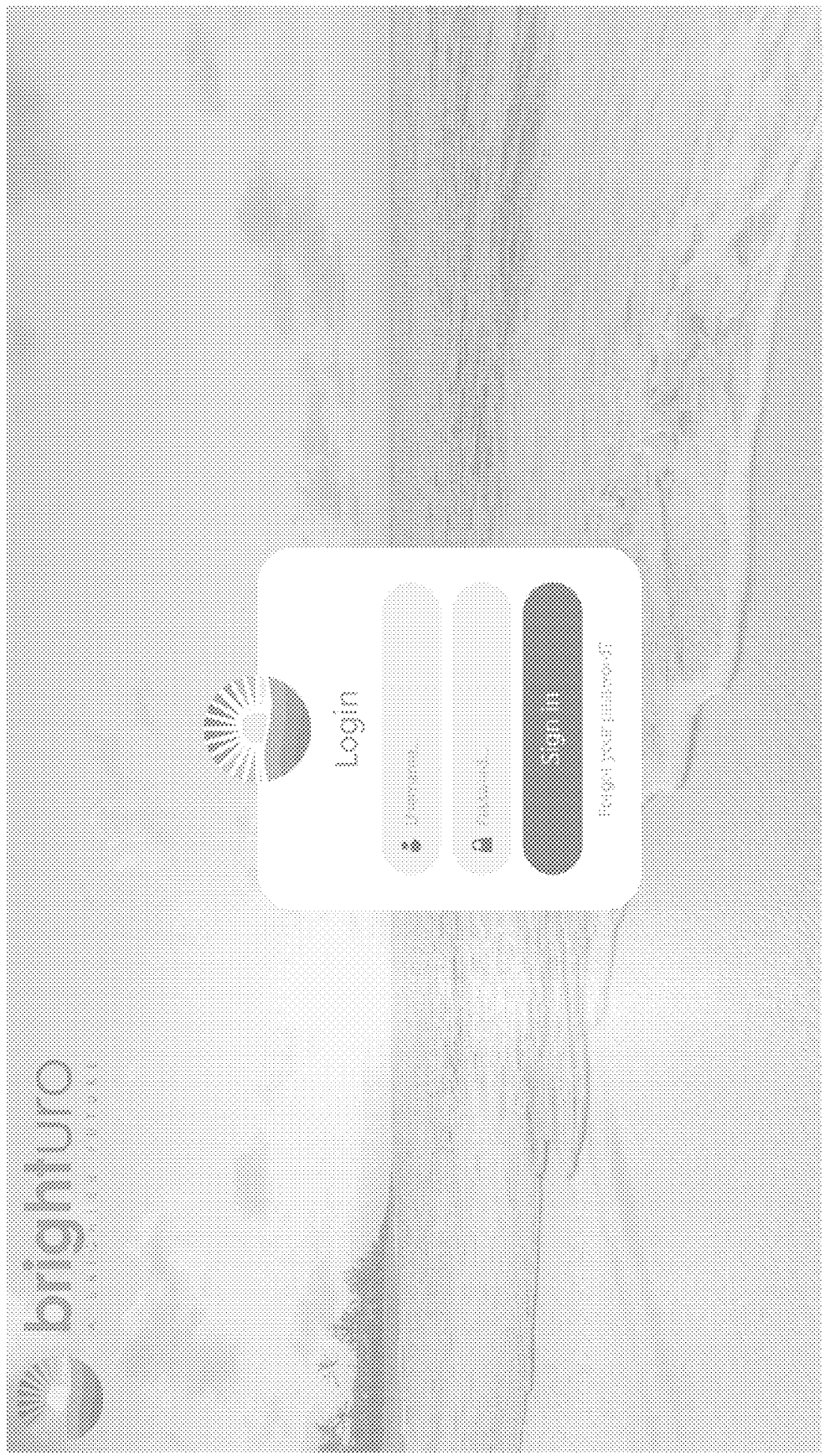
FIG. 151 shows a login screen generated by a computer system that may be utilized with aspects of this disclosure.
Figure 154:
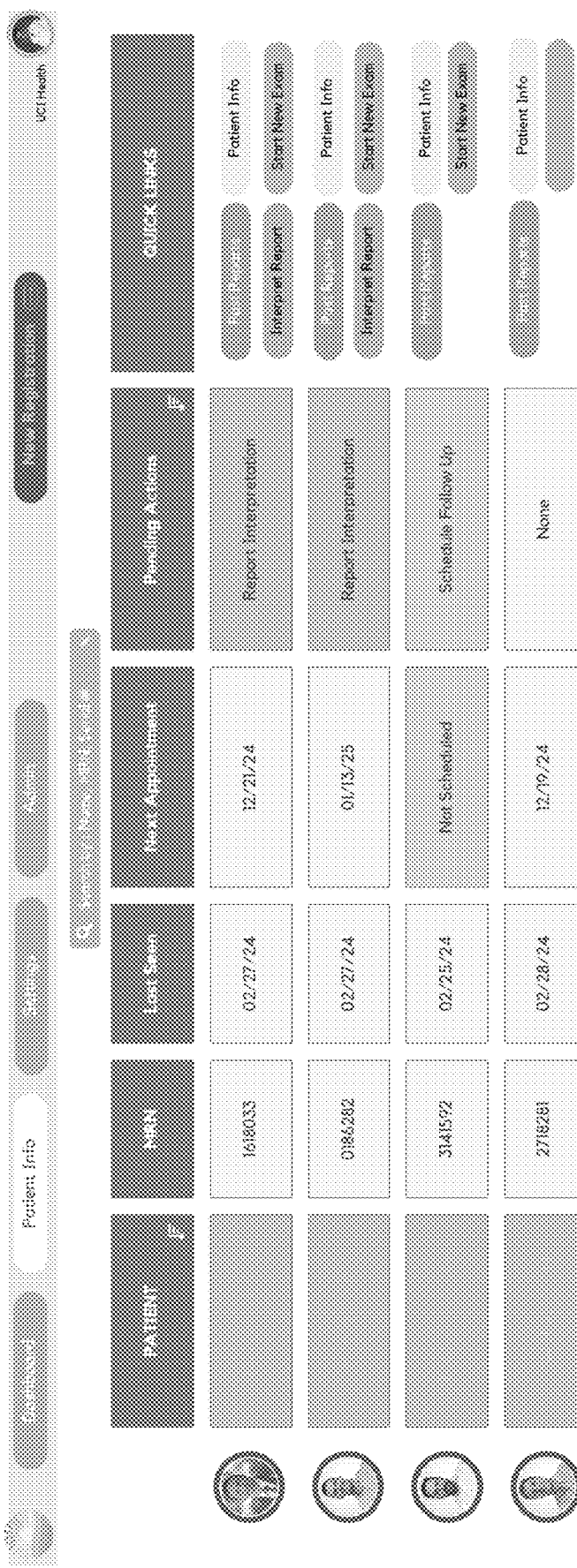
FIG. 154 shows an alternate screen shot generated by a computer system that may be utilized with aspects of this disclosure.
Figure 156:
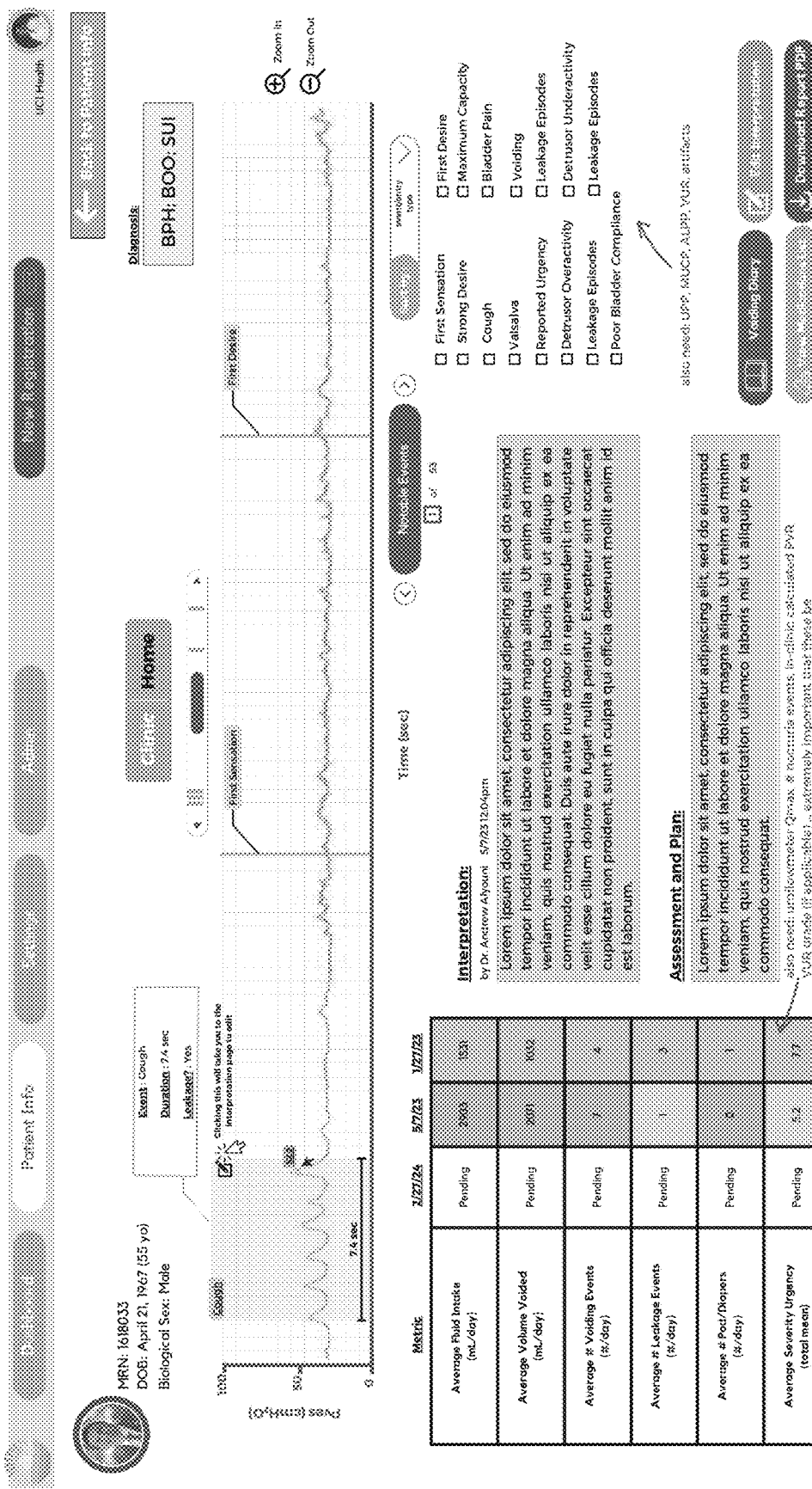
FIG. 156 shows an alternate screen shot generated by a computer system that may be utilized with aspects of this disclosure.
Figure 157:
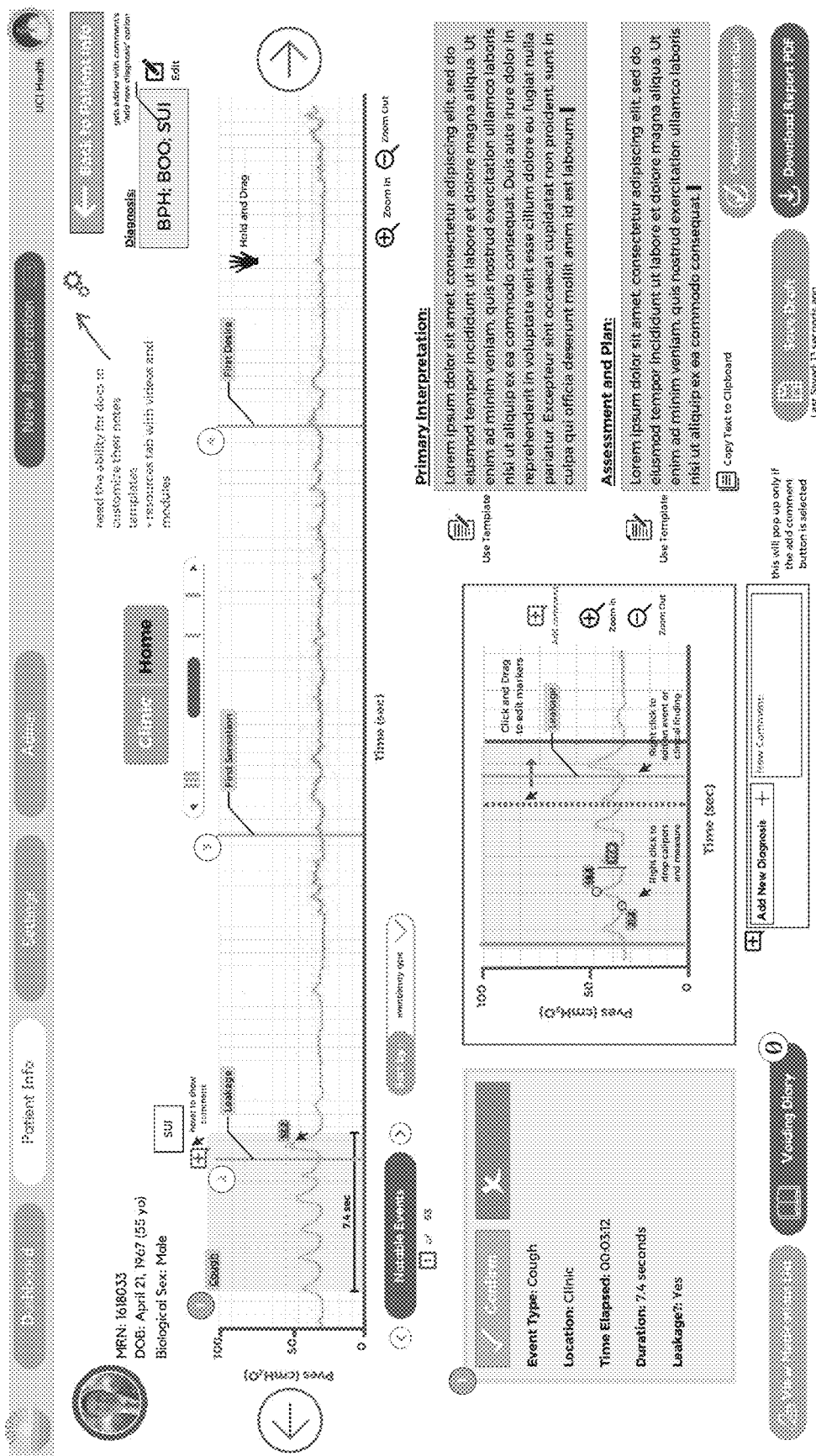
FIG. 157 shows an alternate screen shot generated by a computer system that may be utilized with aspects of this disclosure.
Figure 158:
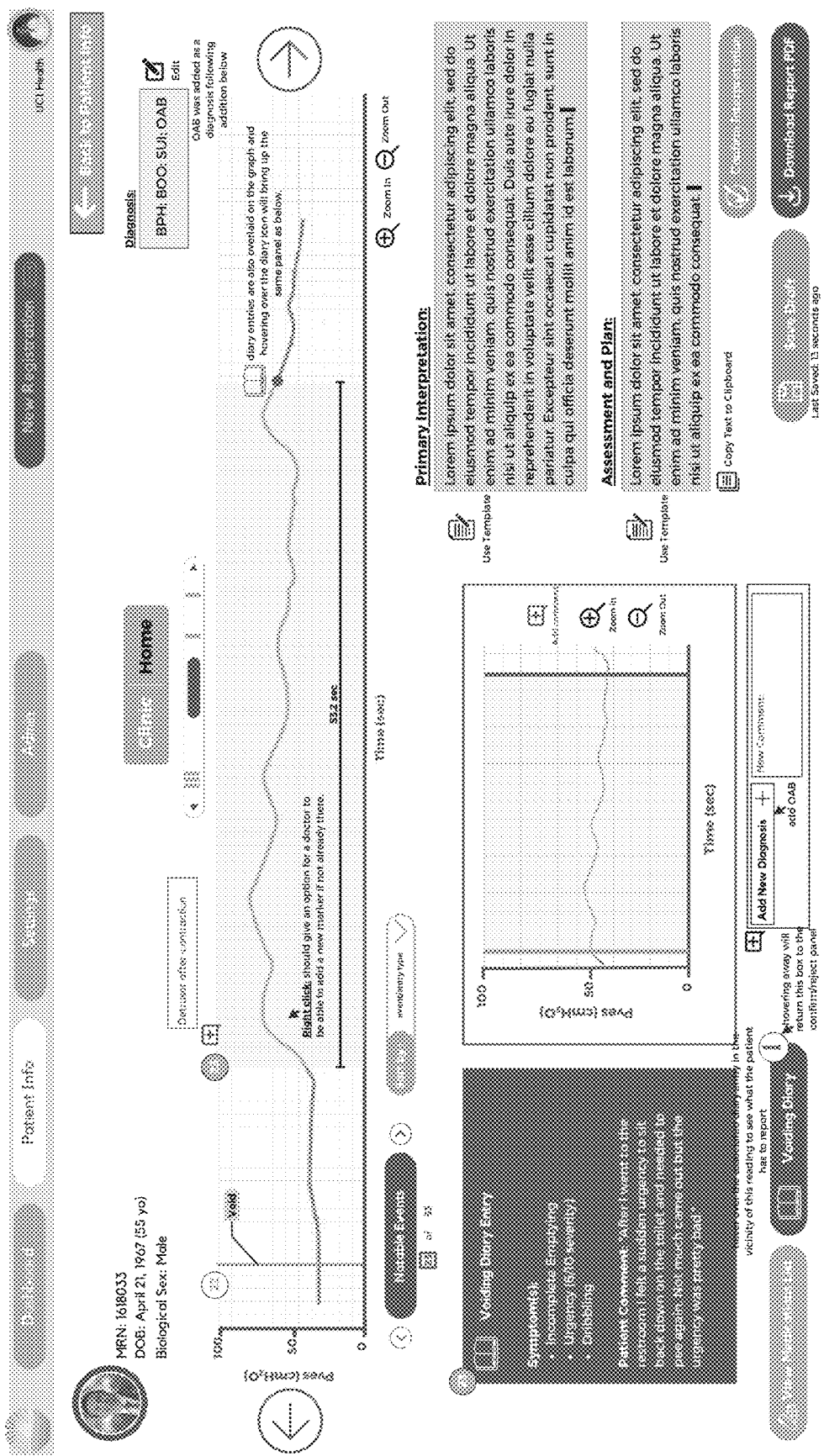
FIG. 158 shows an alternate screen shot generated by a computer system that may be utilized with aspects of this disclosure.

FIG. 151 shows a login screen to use a computer system according to this disclosure. FIGS. 152-158 and 160-165 illustrates screens of information that can be generated by a computer system according to this disclosure.

As used herein, the terms application and module and the like can refer to computer program instructions, encoded on computer storage medium for execution by, or to control the operation of, data processing apparatus. Alternatively or additionally, the program instructions can be encoded on an artificially-generated propagated signal, e.g., a machine-generated electrical, optical, or electromagnetic signal, which is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of the substrates and devices. Moreover, while a computer storage medium is not a propagated signal, a computer storage medium can be a source or destination of computer program instructions encoded in an artificially-generated propagated signal. The computer storage medium is non-transitory and can also be, or be included in, one or more separate physical components or media (e.g., solid-state memory that forms part of a device, disks, or other storage devices).

As used herein, "database" refers to any suitable database for storing information, electronic files or code to be utilized to practice embodiments of this disclosure. As used herein, "server" refers to any suitable server, computer or computing device for performing functions utilized to practice embodiments of this disclosure.

As used herein, "processor" refers to a data-processing apparatus configured to execute computer program instructions, encoded on computer storage medium, wherein the instructions control the operation of the engine. Alternatively or additionally, the program instructions can be encoded on an artificially-generated propagated signal, e.g., a machine-generated electrical, optical, or electromagnetic signal, which is generated to encode information for transmission to suitable receiver apparatus for execution by a data processing apparatus.

A "storage" or "memory" can be, or be included in, a computer-readable storage device, a computer-readable storage substrate, a random or serial access memory array or device, or a combination of one or more of the substrates and devices. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., solid-state memory that forms part of a device, disks, or other storage devices). In accordance with examples of the disclosure, a non-transient computer readable medium containing program can perform functions of one or more methods, modules, engines and/or other system components as described herein.

A computer system 1000 with software, such as a patient and/or clinician application designed to be used on any suitable computing device, such as a server, mobile device (tablet/phone) or computer. The software may operate on a processor that may or may not be resident on a server. The processor has or is in communication with a memory and one or more databases, wherein the processor is configured to store data and run software applications. Some aspects of the computer system 1000 include:

(1) The ability to integrate and synchronize data from the sensor, uroflowmeter, and software, specifically, the ability to align this information in time with high precision.

Devices connected to the server (which may be on a mobile device (tablet or phone) synchronize using any suitable wired connection (if the sensor is outside of the body) or wireless connection (such as Wi-Fi, cellular, or Bluetooth).

(2) Visual data handling techniques that help clinicians review and analyze data may include one or more of the following:

(a) An analyze function, which means the ability to view/analyze/note findings for any one filling/voiding cycle. Because the system/device standardizes reporting and reduces operator variability a repository may be used to develop algorithms to identify characteristics of the data presented to aid a clinician in diagnosis of the waveforms. The waveforms specifically depicting of wireless, catheter-free urodynamics data from a human or animal patient.

(b) An overlay function, which is the ability to overlay two or more filling/voiding cycles to help view/identify trends. This may include a global analysis within the patient to analyze key metrics such as average voids per day, number of leaks per day, and number of nocturia events. Artificial intelligence/machine learning (AI/ML), statistical, and/or mathematical algorithms can be used to highlight a variety of trends including detrusor underactivity (DU), detrusor overactivity (DO), detrusor/sphincter dyssynergia (DSD), leakage, incontinence, and other aspects of bladder filling/storage/voiding dysfunction.

(c) A compare function, which means the ability to directly compare two or more filling/voiding cycles to determine similarities and differences. This may also be used to generate a proprietary scoring mechanism to understand and quantify intra-patient variability across multiple voiding cycles.

(d) A patient versus repository comparison function, which means the ability to analyze a filling/voiding cycle from a patient that can be compared with the data repository to help categorize and identify if any specific forms of bladder dysfunction exist. This information may be provided as a suggestion to the clinician to aid in diagnosis of the patient and save time for the clinician. It may also help to standardize metrics by utilizing reporting from other patients, potentially including patients in other locales or other countries.

(e) An intra-patient comparison function, which is the ability to analyze two or more filling/voiding cycles from the same patient to determine the similarities and differences in the filling/voiding cycles. With multiple cycles this could prove valuable to confirm or deny potential diagnoses through extended monitoring and repeated measurements. The system of this disclosure has the ability to do this during one urodynamics evaluation, or from the same patient but at different times or periods of urodynamics evaluation.

An intra-clinic or intra-clinician comparison function, which is the ability to analyze the data from a clinic or clinician and compare the analysis with aggregated data in a data repository using algorithms to determine a variety of factors including: clinic proficiency, clinician proficiency, adherence to training and other metrics. This type of data could also identify trends through analysis to determine the prevalence of certain urological conditions within certain geographical regions, or types of individuals (such as by age, ethnicity, or lifestyle). When such data is overlayed with aggregated health records through electronic health records (EHR) integration this may support trend analysis for population health management and risk profiles for insurers. The systems, devices, and methods of this disclosure are not limited to the above functions and they can perform any suitable function or provide any suitable data.

Integration and generation of reports through the incorporation of data from a patient's medical records through EHR integration and also data from event detection algorithms from data collected during the urodynamics exam. Use of this information may aid in improving efficiency by pre-populating notes and assessment plans for clinicians. This may be accomplished using templates and advanced signal processing or data science (AI/ML) techniques or using generative AI functionality (such as Chat GPT).

The software (or "App" or "application") is resident on the processor (patient and/or clinician) that can directly or indirectly wirelessly communicate with a server to send/receive information, enable AI/ML, support algorithm development, and facilitate use of cloud-based software applications.

The server or processor can run software designed to integrate with various EHR platforms to streamline clinical workflow. In some embodiments, these algorithms may incorporate natural language processing (NLP) techniques to generate a report including suggested report notes for integration into EHR In other embodiments, this may also incorporate patient history through various means of analysis to include NLP.

The computer system 1000 can also enable distributed and/or remote patient monitoring by collecting data from patients, who may be at home or otherwise be remote to a hospital or health care provider. The data obtained can then be shared with clinicians who may or may not be collocated with the patient to support tele-health or remote care.

The sensor 50 is designed to communicate with the clinician and patient software application (or simply "software" or "App"), which is resident on a server or processor of a computing device. The software may be run on a processor of a computing device to allow clinicians and patients to use the system.

The clinician App allows the clinician to communicate with the sensor wirelessly and prepare it for insertion in the bladder. Once the sensor 50 is removed from the bladder, data can be wirelessly downloaded from the memory in the sensor or downloaded via a wired connection. Further, data may be transmitted by the sensor while it is in the bladder. One means of wireless communications is Bluetooth.

The clinician App also allows clinicians to manually input data such as voiding events, leakage events, urgency, and other patient reported symptoms or events, or any relevant information.

The clinician App allows the clinician to visually observe on a computing device screen and analyze data collected by the sensor, both the patient App and clinician app, and the uroflowmeter. This may be used in a manner that leverages methods of visualizing data including the use of artificial intelligence and machine learning (AI/ML).

The clinician App may also be used in conjunction with any specified clinical protocol to log data pertaining to the patient's behavior. The clinician App will enable the clinician to provide a window by entering the type of event as well as "start" and "stop". This creates a data entry that enables aggregation and analysis of events across patients and intra patient to help develop and train any ML models. These events may include urological events (such as leakage) or other physiological events (such as jumping, standing, coughing, climbing stairs). This enables refinement and enhancement of precision for ML models developed from the dataset.

The clinician App and Web App may also incorporate a feature to simplify the reporting and analysis of urological events. This may appear similar to other quick signing platforms such as Docusign where the report for clinicians is prepared and pre-populated with anticipated voiding events that are either confirmed, rejected, or modified by the clinician reading the report. In this manner, this input aids in "training" any ML models being utilized by the company generating the report.

The clinician App and Web App also incorporate inputs from multiple devices that are synchronized in the cloud which can be utilized to streamline workflow and improve clinic efficiency. This is accomplished visually through the depiction of relevant information and providing pre-populated input which may generate the impetus for a clinical response or intervention (such as a patient report awaiting interpretation). The ability to sort and filter these parameters will allow for some customization of the interface such that each clinician may be able to observe this data consistently.

This Web App may also incorporate direct connections to Electronic Health Records (EHR) systems to provide a comprehensive interface for the patient data. This may include past history, notes, exams, diagnostic labs, and messaging activity.

The clinician Apps may also enable automation and measurement of key urodynamic parameters including but not limited to # of voids per day, # of leakage events, and other events. This may be utilized in conjunction with other visual features, such as shading or coloring, to help simplify interpretation by clinicians.

If the clinician App is connected via EHR, the use of NLP techniques may aid in obtaining clinical insight from past patient notes and history to aid in comprehensive analysis using ML models.

The clinician App may automatically create a report for Clinicians urodynamic evaluation that can be outputted directly into EHR or logged as a PDF file or printed. In some embodiments the reporting feature may use AI and/or ML to generate text for reporting that may be copied and pasted into EHR or automatically populate the notes if enabled. Specifically, templates may be pre-populated using the metrics obtained from the EHR integration and also the algorithms for analysis of the current urodynamics exam or using a generative AI platform with LLMs such as Chat GPT.

The clinician App may also integrate valuable communications methods to enable the clinician to communicate with the patient by conducting a voice call, video call, text message, email, or other method of secure communication.

The patient App enables patients to log any fluid inputs and symptoms the patient experiences and is similar to a digital voiding diary. Other urodynamic parameters may be cataloged by the patient using the App.

Both Apps can communicate with the sensor and with the uroflowmeter using Bluetooth or other wireless protocol and send data to a server for storage, analysis, display, and/or other purposes using any appropriate wireless communications methods such as Bluetooth, Wi-Fi, or cellular.

The clinician web App will enable clinicians to observe and analyze patient data from the examination through the use of a cloud-based server housing data. This enables simple and reliable access for clinicians via any web browser to streamline reporting and ease of use for the clinician to generate the report from any urodynamics evaluation. This App may also incorporate various features to aid in clinical decision making including AI/ML, statistical, and/or mathematical algorithms.

Uroflowmeter

The uroflowmeter 600 is designed to measure the volume of urine voided and changes to the volume voided (i.e., flow).

This data may be stored locally on the device for some period and can also be transmitted wirelessly to the device(s) Apps for analysis, review, display, and/or storage. Once the data is received by one or more Apps it may be sent wirelessly to a server or processor for storage, analysis, display, and/or for other purposes. In some embodiments, the uroflowmeter and sensor may possess a cellular, Wi-Fi, or other antenna that enables direct communication and upload of data to a device, such as a server without the requirement for the clinician App or patient App. The uroflowmeter may use any relevant means of wireless communications including Bluetooth, Wi-Fi, and or cellular.

Wireless Telemetry

The sensor 50 may be designed to wirelessly transmit data in real-time through the body while the sensor is in the bladder. This could be accomplished using a variety of suitable wireless communications and done either continuously, intermittently, or in response to a command. In some embodiments, this may be done by the sensor communicating directly with a smartphone, computer, or similar device. In other embodiments, this may be done using a wireless relay to receive the signal from the sensor in the body and then transmit this signal to another device, such as one that includes the clinician App or patient App.

Volume Sensing

Other methods of volume sensing modalities for the sensor 50 include the following:

Impedance, which uses electrodes to measure conductance of the fluid in the bladder.

Vibration, which uses a shockwave or pressure pulse to be sent from the sensor into the fluid in the bladder and then the volume is sensed using the same or a different sensor.

Optical methods, wherein various light waves are sent from the sensor in the bladder into the bladder and received by sensors on the circuit of the sensor. The light waves could utilize infrared (IR) or visible light.

Lasers, wherein a laser beam would detect the level of fluid and the volume of the bladder and based on that information, the volume of fluid in the bladder is calculated.

Acoustic (audio), which is similar to or the same as sonar and can map the bladder structure and volume of fluid.

Ultrasound, wherein its method of operation is known to those skilled in the art.

Pressure, wherein the pressure sensing signal is processed and input features are identified to incorporate into a ML/AI algorithm to predict volume of fluid.

Each of these modalities may be used in isolation or in combination with other modalities to accomplish the goal of providing reliable fluid volume estimation of the bladder.

Use of AI/ML, statistical, and/or mathematical algorithms to enable volume measurement by evaluating the measurement of area under the curve of a urodynamics trace, derivative of urodynamics pressure waveform, and other aspects of the waveform to enable volume estimation from pressure measurement in the bladder and volume/flow from external uroflowmeter. These algorithms may be developed to utilize one or more of the any combination of the signals from sensing modalities listed above, in conjunction with, or totally separate from, pressure measurements.

Thus, disclosed is the use of a single sensor in the bladder and advanced signal processing techniques to identify and characterize the intra-abdominal pressure waveform. This can then enable the removal of intra-abdominal pressure from the vesical pressure to provide the detrusor pressure. This method can then be used to reconstruct the intra-abdominal pressure waveform with high levels of accuracy. This eliminates the need for the use of a rectal or vaginal catheter to measure intra-abdominal pressure.

Use of the sensor to measure forces exerted on the sensor from the bladder walls can be used to estimate the volume of urine in the bladder. This can be used to estimate post-void residual volume and also time to fill the bladder. This signal may also be utilized with or without advanced signal processing techniques to estimate or derive specific and well validated urodynamic parameters including but not limited to Bladder Contractility Index (BCI), Bladder Wall Thickness (BWT), Detrusor Contraction Index, and other parameters.

The geometric shape and diameter of the sensor may be sized to function at different volumes of urine in the bladder such that the forces of the bladder walls may allow for volume estimation regardless of the volume. One example is that a smaller diameter and/or longer length sensor could enable higher resolution in a smaller bladder whereas a larger diameter and/or longer length sensor would be ideal for measurement of a larger bladder.

The use of a software application and signal processing techniques may be used to identify the offset of a pressure sensor and automatically calibrate the results to accommodate this from one or more filling/voiding cycles. This would streamline the interpretation process for clinicians and improve reliability of analysis.

Some non-limiting examples of the invention are presented below:

Example 1: A tool for inserting a sensor into a bladder, the tool comprising:
an over sheath having a first lumen; and
a push rod used to deploy the sensor.

Example 2: The tool of example 1 further comprising a handle on a first end of the over sheath.

Example 3: The tool of any one of examples 1-3 that further includes a sensor positioned in the first lumen of the over sheath.

Example 4: The tool of any one of examples 1-4, wherein the over sheath is comprised of TPU.

Example 5: The tool of any one of examples 1-4, wherein the push rod includes a handle.

Example 6: The tool of any one of examples 1-7, wherein an outer surface of the over sheath includes depth markings configured to indicate the proper positioning of the tool for insertion of the sensor in the bladder.

Example 7: The tool of any one of examples 1-8, wherein the over sheath further comprises a second lumen configured to permit urine to flow therethrough once the tool has reached the bladder.

Example 8: The tool of example 10, wherein the second lumen includes a removable structure configured to prevent the second lumen from being blocked by lubricant while positioning the tool in the bladder and configured to be removed when a user believes the tool to be in the bladder so as to permit the flow of urine through the second lumen.

Example 9: The tool of any one of examples 1-8, wherein the push rod includes a channel configured so that a string on the sensor can be positioned in the channel.

Some additional non-limiting examples of the sensor are presented below:

Example 1: A sensor configured to detect conditions inside of a bladder, wherein the sensor comprises:
a flexible outer cover having a lumen;
flexible circuitry inside of the flexible outer cover;
a power source inside of the flexible outer cover and in communication with the flexible circuitry; and
one or more parameter sensors inside of the flexible outer cover and in communication with the flexible circuitry, wherein the one or more parameter sensors are configured to measure at least one of (i) a volume of liquid in the bladder, (ii) a rate of liquid discharge from the bladder, (iii) pressure in the bladder, (iv) the volume of the bladder, (v) anomalies in the bladder, and (vi) chemistry of urine in the bladder.
wherein the sensor is configured to move from a first position in which it is configured to be retained in the bladder and not be accidentally discharged, to a second position in which the sensor is configured to be inserted into the bladder through the urethra.

Example 2: The sensor of example 1, wherein the flexible outer cover is comprised of silicone.

Example 3: The sensor of any one of examples 1-2, wherein at least one of the one or more parameter sensors is on the flexible circuitry.

Example 4: The sensor of any one of examples 1-3, wherein the power source is a battery.

Example 5: The sensor of any one of examples 1-4, wherein the power source is mechanically coupled to the electronic circuitry.

Example 6: The sensor of any one of examples 1-5 that includes a distal end having a string attached thereto, wherein the string is configured to remain outside of the body when the sensor is positioned in the bladder, and the string can be pulled by a user or clinician to remove the sensor from the bladder.

Example 7: The sensor of any one of examples 1-6 that includes a distal end that is straight.

Example 8: The sensor of any one of examples 1-6 that includes a distal end that is coude.

Example 9: The sensor of any one of examples 1-8 that is pre-filled with incompressible fluid and configured to permit fluid to translate force to the electronic sensor.

Example 10: The sensor of any one of examples 1-9 that further includes an antenna.

Example 11: The sensor of any one of examples 1-10 that is configured to transmit wireless communications.

Example 12: The sensor of any one of examples 1-11 that is configured to receive wireless communications.

Example 13: The sensor of any one of examples 1-12 that further includes a processor and a memory configured to store measured parameters.

Example 14: The sensor of any one of examples 1-13 that further includes software configured to analyze measured parameters.

Example 15: The sensor of any one of examples 1-14 that further includes a shape memory spring positioned inside of the flexible outer cover.

Example 16: The sensor of example 15, wherein the shape memory spring is comprised of metal or plastic.

Example 17: The sensor of example 16, wherein the shape memory spring is comprised of metal or steel.

Example 18: The sensor of any one of examples 1-17, wherein the sensor is circular or curved when in the first position and the sensor is straight when in the second position.

Example 19: The sensor of any one of examples 1-18 that includes a semi-rigid endcap on the distal end of the sensor and a semi-rigid endcap on the proximal end of the sensor.

Example 20: The sensor of example 20, wherein each endcap is comprised of steel, plastic, or other material.

Example 21: The sensor of any one of examples 15 or 16, wherein the shape memory spring is flat (rectangular in cross section).

Example 22: The sensor of any one of examples 15-16, or 21 that further comprises a distal end and a semi-rigid endcap on the distal end and a semi-rigid endcap on the proximal end, wherein the shape memory spring mates with each of the endcaps.

Example 23: The sensor of any one of examples 15-16 or 21-22, wherein the shape memory spring is coated with an electric insulating material.

Example 24: The sensor of any one of examples 15-16 or 21-23, wherein the shape memory spring is coated with a material that is resistant to lubricating oils.

Example 25: The sensor of any one of examples 15-16 or 21-24, wherein the shape memory spring is coated with an adhesive.

Example 26: The sensor of any one of examples 1-25 designed to communicate with an external computing device with software operable on the processor, wherein the processor is configured by the software to view, analyze, store, and make note findings for one or more bladder filling and voiding cycles.

Example 27: The system of example 26, wherein the software configures the processor to overlay two or more filling/voiding cycles to help identify trends.

Example 28: The system of any one of examples 26-27, wherein the processor uses AI/ML algorithms to detect trends such as detrusor underactivity, detrusor overactivity, leakage incontinence, and/or other aspects of bladder filling/storage/voiding dysfunction.

Example 29: The system of any one of examples 26-28 that compares data obtained by the one or more parameter sensors to aggregated data in a data repository, wherein the software further configures the processor to determine one or more of (a) clinic proficiency, (b) clinician proficiency, (c) adherence to training, (d) the prevalence of certain urological conditions within (i) certain geographical regions, (ii) ACX, (iii) ethnicity, (iv) age, or (v) lifestyle.

Example 30: The sensor of any one of examples 1-29 that is configured to utilize one or more of the following to detect fluid volume and level in the bladder: (a) one or more shock waves or pressure pulses, (b) one or more light waves, (c) one or more lasers, (d) one or more acoustic signals, (e) ultrasound, (f) conductivity, and (g) pressure.

Some further non-limiting examples of this disclosure are presented below:

Example 1: A tool for inserting a sensor into a bladder, the tool comprising:
an over sheath having a first lumen;
a push rod positioned in the first lumen; and
a removable spacer positioned between the push rod and the over sheath.

Example 2: The tool of example 1 further comprising a handle on a first end of the over sheath.

Example 3: The tool of example 2, wherein the spacer is not positioned on the handle.

Example 4: The tool of any one of examples 1-3 that further includes a sensor positioned in the first lumen of the over sheath.

Example 5: The tool of any one of examples 1-4, wherein the over sheath is comprised of TPU.

Example 6: The tool of any one of examples 1-5, wherein the spacer has a predetermined length.

Example 7: The tool of any one of examples 1-6, wherein the push rod includes a handle.

Example 8: The tool of any one of examples 1-7, wherein the removable spacer is positioned between the over sheath handle and the push rod handle.

Example 9: The tool of any one of examples 1-8, wherein an outer surface of the over sheath includes depth markings configured to indicate the proper positioning of the tool for insertion of the sensor in the bladder.

Example 10: The tool of any one of examples 1-9, wherein the over sheath further comprises a second lumen configured to permit urine to flow therethrough once the tool has reached the bladder.

Example 11: The tool of example 10, wherein the second lumen includes a removable structure configured to prevent the second lumen from being blocked by lubricant while positioning the tool in the bladder and configured to be removed when a user believes the tool to be in the bladder so as to permit the flow of urine through the second lumen.

Example 12: The tool of any one of examples 1-11, wherein the push rod includes a channel configured so that a string on the sensor can be positioned in the channel.

Example 13: The tool of any one of examples 1-12, wherein the tool is configured such that the push rod cannot be advanced past the removable spacer when the removable spacer is positioned on the over sheath.

Example 14: The tool of any one of examples 1-13, wherein the tool is configured such that the push rod can push the sensor out of the over sheath only after the spacer is removed.

Some further non-limiting examples of this disclosure are shown below:

Example 1: A sensor configured to detect conditions inside of a bladder, wherein the sensor comprises:
- a flexible outer cover having a lumen;
- flexible circuitry inside of the flexible outer cover;
- a power source inside of the flexible outer cover and in communication with the flexible circuitry; and
- one or more parameter sensors inside of the flexible outer cover and in communication with the flexible circuitry, wherein the one or more parameter sensors are configured to measure at least one of (i) a volume of liquid in the bladder, (ii) a rate of liquid discharge from the bladder, (iii) pressure in the bladder, (iv) the volume of the bladder, (v) anomalies in the bladder, and (vi) chemistry of urine in the bladder.
- wherein the sensor is configured to move from a first position in which it is configured to be retained in the bladder and not be accidentally discharged, to a second position in which the sensor is configured to be inserted into the bladder through the urethra.

Example 2: The sensor of example 1, wherein the flexible outer cover is comprised of silicone.

Example 3: The sensor of any one of examples 1-2, wherein at least one of the one or more parameter sensors is on the flexible circuitry.

Example 4: The sensor of any one of examples 1-3, wherein the power source is a battery.

Example 5: The sensor of any one of examples 1-4, wherein the power source is mechanically coupled to the electronic circuitry.

Example 6: The sensor of any one of examples 1-5 that includes a distal end having a string attached thereto, wherein the string is configured to remain outside of the body when the sensor is positioned in the bladder, and the string can be pulled by a user or clinician to remove the sensor from the bladder.

Example 7: The sensor of any one of examples 1-6 that includes a distal end that is straight.

Example 8: The sensor of any one of examples 1-6 that includes a distal end that is coude.

Example 9: The sensor of any one of examples 1-8 that is pre-filled with incompressible fluid and configured to permit fluid to translate force to the electronic sensor.

Example 10: The sensor of any one of examples 1-9 that further includes an antenna.

Example 11: The sensor of any one of examples 1-10 that is configured to transmit wireless communications.

Example 12: The sensor of any one of examples 1-11 that is configured to receive wireless communications.

Example 13: The sensor of any one of examples 1-12 that further includes a processor and a memory configured to store measured parameters.

Example 14: The sensor of any one of examples 1-13 that further includes software configured to analyze measured parameters.

Example 15: The sensor of any one of examples 1-14 that further includes a shape memory spring positioned inside of the flexible outer cover.

Example 16: The sensor of example 15, wherein the shape memory spring is comprised of metal or plastic.

Example 17: The sensor of example 16, wherein the shape memory spring is comprised of metal or steel.

Example 18: The sensor of any one of examples 1-17, wherein the sensor is circular or curved when in the first position and the sensor is straight when in the second position.

Example 19: The sensor of any one of examples 1-18 that includes a semi-rigid endcap on the distal end of the sensor and a semi-rigid endcap on the proximal end of the sensor.

Example 20: The sensor of example 20, wherein each endcap is comprised of steel, plastic, or other material.

Example 21: The sensor of any one of examples 15 or 16, wherein the shape memory spring is flat.

Example 22: The sensor of any one of examples 15-16, or 21 that further comprises a distal end and a semi-rigid endcap on the distal end and a semi-rigid endcap on the proximal end, wherein the shape memory spring mates with each of the endcaps.

Example 23: The sensor of any one of examples 15-16 or 21-22, wherein the shape memory spring is coated with an electric insulating material.

Example 24: The sensor of any one of examples 15-16 or 21-23, wherein the shape memory spring is coated with a material that is resistant to lubricating oils.

Example 25: The sensor of any one of examples 15-16 or 21-24, wherein the shape memory spring is coated with an adhesive.

Example 26: The sensor of any one of examples 1-25 designed to communicate with an external computing device with software operable on the processor, wherein the processor is configured by the software to view, analyze, store, and make note findings for one or more bladder filling and voiding cycles.

Example 27: The system of example 26, wherein the software configures the processor to overlay two or more filling/voiding cycles to help identify trends.

Example 28: The system of any one of examples 26-27, wherein the processor uses AI/ML, statistical, and/or mathematical algorithms to detect trends such as detrusor underactivity, detrusor overactivity, leakage incontinence, and/or other aspects of bladder filling/storage/voiding dysfunction.

Example 29: The system of any one of examples 26-28 that compares data obtained by the one or more parameter sensors to aggregated data in a data repository, wherein the software further configures the processor to determine one or more of (a) clinic proficiency, (b) clinician proficiency, (c) adherence to training, (d) the prevalence of certain urological conditions within (i) certain geographical regions, (ii) ACX, (iii) ethnicity, (iv) age, or (v) lifestyle.

Example 30: The sensor of any one of examples 1-29 that is configured to utilize one or more of the following to detect fluid volume and level in the bladder: (a) one or more shock waves or pressure pulses, (b) one or more light waves, (c) one or more lasers, (d) one or more acoustic signals, (e) ultrasound, (f) conductivity, and (g) pressure.

Some further non-limiting examples of this disclosure are presented below:

Example 1: A sensor configured to detect conditions inside of a bladder, wherein the sensor comprises:
- a flexible outer cover having a lumen, a distal end and a proximal end, wherein
- the distal end has a key configured to be received in a keyway formed in the distal end of an insertion tool;
- flexible circuitry inside of the flexible outer cover;

a power source inside of the flexible outer cover and in communication with the flexible circuitry; and one or more parameter sensors inside of the flexible outer cover and in communication with the flexible circuitry, wherein the one or more parameter sensors are configured to measure at least one of (i) a volume of liquid in the bladder, (ii) a rate of liquid discharge from the bladder, (iii) pressure in the bladder, (iv) the volume of the bladder, (v) anomalies in the bladder, and (vi) chemistry of urine in the bladder.

wherein the sensor is configured to move from a first position in which it is configured to be retained in the bladder and not be accidentally discharged, to a second position in which the sensor is configured to be inserted into the bladder through the urethra.

Example 2: The sensor of example 1, wherein the flexible outer cover is comprised of silicone.

Example 3: The sensor of any one of examples 1-2, wherein at least one of the one or more parameter sensors is on the flexible circuitry.

Example 4: The sensor of any one of examples 1-3, wherein the power source is a battery.

Example 5: The sensor of any one of examples 1-4, wherein the power source is mechanically coupled to the electronic circuitry.

Example 6: The sensor of any one of examples 1-5 that includes a distal end having a string attached thereto, wherein the string is configured to remain outside of the body when the sensor is positioned in the bladder, and the string can be pulled by a user or clinician to remove the sensor from the bladder.

Example 7: The sensor of any one of examples 1-6 that includes a distal end that is straight.

Example 8: The sensor of any one of examples 1-6 that includes a distal end that is coude-shaped.

Example 9: The sensor of any one of examples 1-8 that is pre-filled with incompressible fluid and configured to permit fluid to translate force to the electronic sensor.

Example 10: The sensor of any one of examples 1-9 that further includes an antenna.

Example 11: The sensor of any one of examples 1-10 that is configured to transmit wireless communications.

Example 12: The sensor of any one of examples 1-11 that is configured to receive wireless communications.

Example 13: The sensor of any one of examples 1-12 that further includes a processor and a memory configured to store measured parameters.

Example 14: The sensor of any one of examples 1-13 that further includes software configured to analyze measured parameters.

Example 15: The sensor of any one of examples 1-14 that further includes a shape memory spring positioned inside of the flexible outer cover.

Example 16: The sensor of example 15, wherein the shape memory spring is comprised of metal or plastic.

Example 17: The sensor of example 16, wherein the shape memory spring is comprised of metal or steel.

Example 18: The sensor of any one of examples 1-17, wherein the sensor is circular or curved when in the first position and the sensor is straight when in the second position.

Example 19: The sensor of any one of examples 1-18 that includes a semi-rigid endcap on the distal end of the sensor and a semi-rigid endcap on the proximal end of the sensor.

Example 20: The sensor of example 20, wherein each endcap is comprised of steel, plastic, or other material.

Example 21: The sensor of any one of examples 15 or 16, wherein the shape memory spring is flat.

Example 22: The sensor of any one of examples 15-16, or 21 that further comprises a distal end and a semi-rigid endcap on the distal end and a semi-rigid endcap on the proximal end, wherein the shape memory spring mates with each of the endcaps.

Example 23: The sensor of any one of examples 15-16 or 21-22, wherein the shape memory spring is coated with an electric insulating material.

Example 24: The sensor of any one of examples 15-16 or 21-23, wherein the shape memory spring is coated with a material that is resistant to lubricating oils.

Example 25: The sensor of any one of examples 15-16 or 21-24, wherein the shape memory spring is coated with an adhesive.

Example 26: The sensor of any one of examples 1-25, wherein the sensor is configured to communicate with an external computing device with software operable on a processor, wherein the processor is configured by the software to view, analyze, store, and/or make note findings for one or more bladder filling and voiding cycles.

Example 27: The sensor of example 26, wherein the software configures the processor to overlay two or more filling/voiding cycles to help identify trends.

Example 28: The sensor of any one of examples 26-27, wherein the processor uses AI/ML algorithms to detect trends such as detrusor underactivity, detrusor overactivity, leakage incontinence, and/or other aspects of bladder filling/storage/voiding dysfunction.

Example 29: The sensor of any one of examples 26-28, wherein the processor is further configured to compare data obtained by the sensor to aggregated data in a data repository, wherein the software further configures the processor to determine one or more of (a) clinic proficiency, (b) clinician proficiency, (c) adherence to training, (d) the prevalence of certain urological conditions within (i) certain geographical regions, (ii) ACX, (iii) ethnicity, (iv) age, or (v) lifestyle.

Example 30: The sensor of any one of examples 1-29 that is configured to utilize one or more of the following to detect fluid volume and level in the bladder: (a) one or more shock waves or pressure pulses, (b) one or more light waves, (c) one or more lasers, (d) one or more acoustic signals, (e) ultrasound, (f) conductivity, and (g) pressure.

Example 31: The sensor of any one of examples 1-30 that further includes a proximal end configured to be connected to a removal string.

Example 32: The sensor of example 31 that further includes a removal string attached to the proximal end.

Example 33: The sensor of any one of examples 1-32, wherein the distal end is comprised of silicone rubber.

Example 34: The sensor of any one of examples 1-33, wherein the distal end has a durometer of 70 Shore A Example 35: The sensor of any one of examples 31-34, wherein the proximal end is comprised of silicone rubber.

Example 36: The sensor of any one of examples 31-35, wherein the proximal end has a durometer of 60-78 Shore A Example 37: The sensor of any one of examples 1-36, wherein the distal end is coude shaped.

Example 38: The sensor of example 37, wherein the distal tip has an upward bend of between 5° and 15° when positioned to be deployed in a bladder.

Example 39: The sensor of any one of examples 1-39, wherein the distal end is adhesively applied to the sensor flexible outer cover.

Example 40: The sensor of any one of examples 31-39, wherein the proximal end is adhesively applied to the sensor flexible outer cover.

Example 41: The sensor of any of examples 1-40, wherein the flexible outer cover comprises silicone rubber.

Example 42: The sensor of example 41, wherein the silicone rubber is extruded.

Example 43: The sensor of any one of examples 1-42, wherein the flexible outer cover has a durometer of 30-80 Shore A.

Example 44: The sensor of any one of examples 1-44, wherein the flexible outer cover has a wall thickness of 0.05"-0.20".

Example 45: The sensor of any one of examples 1-46, wherein the flexible outer cover further includes a metal braid positioned over a flexible tube.

Example 46: The sensor of example 45 that further includes a plastic or silicone rubber over molded onto the metal braid.

Example 47: The sensor of example 46, wherein the over mold is silicone rubber.

Example 48: The sensor any one of examples 45-47, wherein the metal braid is comprised of stainless steel.

Example 49: The sensor of any one of examples 31-48, wherein the proximal end has a tip and the tip is configured to engage a second, proximal lumen of an insertion tool into which the sensor is positioned.

Example 50: The sensor of example 50, wherein the tip of the proximal end has a rectangular shape and is configured to be received in a rectangular entry of the second, proximal lumen of the insertion tool.

Example 51: The sensor of any one of examples 1-50, wherein the inside of the flexible outer cover is defined as a cavity or housing and contains a fluid that is a liquid.

Example 52: The sensor of example 51, wherein the housing comprises fluid and air.

Example 53: The sensor of example 51, wherein the housing comprises fluid.

Example 54: The sensor of example 51 or example 52, wherein the fluid is silicone oil.

Example 55: The sensor of any one of examples 53-54, wherein the pressure in the housing is greater than atmospheric pressure.

Example 56: The sensor of any one of examples 52-55, wherein the fluid is a flourosilicone oil.

Example 57: The sensor of any one of examples 1-56, wherein none of the parameter sensors are exposed to an environment outside of the sensor housing.

Example 58: The sensor of any one of examples 1-57 that further includes a Septa.

Example 59: The sensor of example 58, wherein the Septa is positioned at the distal end of the sensor.

Example 60: The sensor of example 59, wherein the Septa is formed as part of the distal end of the sensor.

Example 61: The sensor of any one of examples 58-60, wherein the Septa is comprised of compression molded rubber or elastomer.

Example 62: The sensor of any one of examples 52-61, wherein the fluid is placed in the sensor housing to partially fill the housing, the second end is then attached to the flexible outer covering, and the housing is further filled with fluid by pressing a needle of a syringe through the distal end and injecting more fluid into the housing via the syringe.

Example 63: The sensor of any one of examples 52-62, wherein at least some air is removed from the sensor housing after the fluid has been placed in the housing.

Example 64: The sensor of example 63, wherein the air is removed using a syringe with a needle.

Example 65: The sensor of example 64, wherein the needle of the syringe is pressed through the distal end to remove the air.

Example 66: The sensor of any one of examples 62-65, wherein the housing volume is filled about 90% with fluid before attaching the second end.

Example 67: The sensor of any one of examples 53-66, wherein the pressure inside of the housing is from 1200-1400 hPa, or 1200-1300 hPa.

Example 68: A system including an insertion tool and any of the sensors of examples 1-67 positioned therein.

Example 69: The system of example 68, wherein the insertion tool has a distal end, a proximal end, and a lumen configured to receive the sensor.

Example 70: The system of example 69, wherein the insertion tool comprises a handle at its proximal end.

Example 71: The system of example 68 or example 70, wherein the lumen has a first, distal section having a first cross-sectional area, and a second, proximal section having a second cross-sectional area that is less than the first cross-sectional area.

Example 72: The system of example 71, wherein the second cross-sectional area is too small to permit passage of the proximal end of the sensor therethrough.

Example 73: The system of any one of examples 71-72, wherein the first cross-sectional area is circular.

Example 74: The system of any one of examples 71-73, wherein the second cross-sectional area is rectangular or rectangular with rounded edges.

Example 75: The system of any one of examples 71-74, wherein the proximal end of the sensor has a tip that is configured to be received in the second, proximal section of the lumen of the insertion tool.

Example 76: The system of any one of examples 69-75, wherein the proximal end of the insertion tool comprises a keyway that receives a key on the distal end of the sensor.

Example 77: The system of any one of examples 68-76 that further includes a push rod configured to push the sensor out of the insertion tool.

Example 78: An insertion tool having a lumen configured to at least partially receive any of the sensors of claims 1-67.

Example 79: The insertion tool of example 78 that has a distal end, a proximal end, and a lumen configured to receive the sensor.

Example 80: The insertion tool of example 78 or example 79 that comprises a handle at its proximal end.

Example 81: The insertion tool of any one of examples 78-80, wherein the lumen has a first, distal section having a first cross-sectional area, and a second, proximal section having a second cross-sectional area that is less than the first cross-sectional area.

Example 82: The insertion tool of example 81, wherein the second cross-sectional area is too small to permit passage of the proximal end of the sensor therethrough.

Example 83: The insertion tool of any one of examples 81-82, wherein the first cross-sectional area is circular.

Example 84: The insertion tool of any one of examples 81-83, wherein the second cross-sectional area is rectangular or rectangular with rounded edges.

Example 85: The insertion tool of any one of examples 81-84, wherein the proximal end of the sensor has a tip that is configured to be received in the second, proximal section of the lumen of the insertion tool.

Example 86: The insertion tool of any one of examples 79-85, wherein the distal end of the insertion tool comprises a keyway configured to receive a key on the distal end of the sensor.

Further non-limiting examples of this disclosure are as follows:

Example 1: A casing for retaining a urology sensor kit prior to deployment, wherein the kit has a top, a bottom, and form in the bottom, wherein the form comprises:
  a first indentation configured to retain a sensor having a string at its proximal end and configured such that a proximal end of the sensor and the string are positioned in a lumen of an insertion tool;
  a second indentation connected to the first indentation and configured to retain the insert tool;
  a third indentation connected to the second indentation and configured to a handle of the insertion; and
  a fourth indentation not in connection with the first, the second, or the third, indentation and configured to retain a push rod.

Example 2: the casing of example 1 that further includes a sensor, an insert tool, a handle of the insert tool, and the push rod.

Example 3: the casing of example 1 or example 2, wherein the first indentation is curved and configured such that the sensor is in its first, curved position when in the first indentation.

Example 4: The casing of any of examples 1-3, wherein the form is comprised of a formed material.

Example 5: The casing of any of examples 1-4, wherein the casing comprises an outer shell that is harder than the form and that is comprised of metal or plastic.

The present invention has been described above with reference to a number of exemplary embodiments and examples. It should be appreciated that the particular embodiments shown and described herein are illustrative of the invention and its best mode and are not intended to limit in any way the scope of the invention as set forth in the claims. The features of the various embodiments may stand alone or be combined in any combination. Further, unless otherwise noted, various illustrated steps of a method can be performed sequentially or at the same time, and not necessarily be performed in the order illustrated. It will be recognized that changes and modifications may be made to the exemplary embodiments without departing from the scope of the present invention. These and other changes or modifications are intended to be included within the scope of the present invention, as expressed in the following claims.

What is claimed is:

1. A device for detecting conditions inside a bladder of a subject, the device configured to transition from a first state in which the device is insertable through a urethra of the subject and into the subject's bladder to a second state in which the device is configured to be retained inside the subject's bladder, the device being at least partially curved when in the second state, the device comprising:
  a tubular housing comprising a first end, a second end opposite the first end, a length extending between the first and second ends, and an interior cavity, wherein the tubular housing comprises a flexible material;
  a flexible circuit board positioned within the interior cavity and extending along a portion of the length of the tubular housing, the flexible circuit board comprising a first side and a second side opposite the first side;
  a pressure sensor positioned within the interior cavity and mounted to the first side of the flexible circuit board;
  a processor positioned within the interior cavity and mounted to the first side of the flexible circuit board;
  an antenna positioned within the interior cavity and mounted to the first side of the flexible circuit board, the antenna configured for wireless communication with an external computing device;
  a battery positioned within the interior cavity and proximate the first end of the tubular housing, the battery electrically connected to the flexible circuit board;
  a button positioned within the interior cavity and mounted to the first side of the flexible circuit board, the button spaced away from the pressure sensor and configured to initiate activation of the device;
  a spine positioned within the interior cavity and connected to the second side of the flexible circuit board, the spine configured to bias the device toward the second state in which the device is at least partially curved, the spine comprising a first spine end that is positioned proximate the battery and a second spine end that is positioned opposite the first spine end, wherein the spine comprises a material that is more rigid than the flexible material of the tubular housing;
  a spacer comprising a body configured to receive the second spine end and inhibit the second spine end from contacting the tubular housing;
  a first endcap connected to the first end of the tubular housing;
  a second endcap connected to the second end of the tubular housing, at least a portion of the second endcap comprising a coude shape configured to facilitate insertion of the device through the subject's urethra and into the subject's bladder;
  a string connected to the first endcap, the string configured to aid removal of the device from the subject's bladder;
  a septum positioned between at least a portion of the spacer and at least a portion of the second endcap; and
  an incompressible fluid disposed within the interior cavity such that a pressure inside the interior cavity is greater than atmospheric pressure, the incompressible fluid configured to transmit pressure from within the subject's bladder to the pressure sensor of the device;
  wherein the septum is configured to seal the incompressible fluid within the interior cavity at said pressure inside the interior cavity and inhibit external gases from entering the interior cavity.

2. The device of claim 1, wherein said pressure inside the interior cavity is at least 1250 hPa.

3. The device of claim 1, wherein the spine comprises stainless steel.

4. The device of claim 1, wherein the spine is at least partially covered with a non-conductive material.

5. The device of claim 1, wherein at least a portion of the second side of the flexible circuit board is not connected to the spine.

6. The device of claim 1, wherein the septum comprises rubber.

7. The device of claim 1, wherein the spacer comprises plastic.

8. A device for detecting conditions inside a bladder of a subject, the device configured to transition from a first state in which the device is insertable through a urethra of the subject and into the subject's bladder to a second state in which the device is configured to be retained inside the subject's bladder, the device comprising:
  a housing comprising a first end, a second end opposite the first end, and an interior cavity, wherein the housing comprises a flexible material;

a flexible circuit board positioned within the interior cavity, the flexible circuit board comprising a first side and a second side opposite the first side;

a pressure sensor mounted to the first side of the flexible circuit board;

a processor mounted to the first side of the flexible circuit board;

an antenna mounted to the first side of the flexible circuit board and configured for wireless communication with an external computing device;

a battery positioned proximate the first end of the housing and electrically connected to the flexible circuit board;

a spine positioned within the interior cavity and connected to the second side of the flexible circuit board, the spine configured to bias the device toward the second state, the spine comprising a first spine end that is positioned proximate the battery and a second spine end that is positioned opposite the first spine end, wherein the spine comprises a material that is more rigid than the flexible material of the housing;

a spacer comprising a body configured to receive the second spine end and inhibit the second spine end from contacting the housing;

a first endcap connected to the first end of the housing;

a second endcap connected to the second end of the housing;

a septum positioned between at least a portion of the spacer and at least a portion of the second endcap; and an incompressible fluid disposed within the interior cavity and configured to transmit pressure from within the subject's bladder to the pressure sensor of the device;

wherein the septum is configured to seal the incompressible fluid within the interior cavity and inhibit external gases from entering the interior cavity.

9. The device of claim 8, wherein the incompressible fluid is disposed within the interior cavity such that a pressure inside the interior cavity is greater than atmospheric pressure.

10. The device of claim 9, wherein said pressure inside the interior cavity is at least 1250 hPa.

11. The device of claim 8, wherein the spine comprises stainless steel.

12. The device of claim 8, wherein the spine is at least partially covered with a non-conductive material.

13. The device of claim 8, wherein at least a portion of the second side of the flexible circuit board is not connected to the spine.

14. The device of claim 8, wherein the septum comprises rubber.

15. The device of claim 8, wherein the spacer comprises plastic.

16. A device for detecting conditions inside a bladder of a subject, the device configured to transition from a first state in which the device is insertable through a urethra of the subject and into the subject's bladder to a second state in which the device is configured to be retained inside the subject's bladder, the device comprising:

a housing comprising a first end, a second end, and an interior cavity;

a flexible circuit board positioned within the interior cavity;

a pressure sensor mounted to the flexible circuit board;

a spine positioned within the interior cavity and connected to the flexible circuit board, the spine configured to bias the device toward the second state;

a spacer comprising a body configured to receive an end of the spine and inhibit the end of the spine from contacting the housing;

a first endcap connected to the first end of the housing;

a second endcap connected to the second end of the housing; and an incompressible fluid disposed within the interior cavity and configured to transmit pressure from within the subject's bladder to the pressure sensor of the device;

wherein the device further comprises a septum configured to seal the incompressible fluid within the interior cavity and inhibit external gases from entering the interior cavity.

\* \* \* \* \*